(12) United States Patent
Vlasik et al.

(10) Patent No.: US 10,633,431 B2
(45) Date of Patent: Apr. 28, 2020

(54) METHOD FOR NEUTRALIZING HEPATITIS C VIRUS, FULLY HUMAN MONOCLONAL ANTIBODY AGAINST HEPATITIS C VIRUS (VARIANTS), COMPOSITION OF FULLY HUMAN MONOCLONAL ANTIBODIES AGAINST HEPATITIS C VIRUS AND HYBRID MOUSE/HUMAN PRODUCER CELL LINE OF FULLY HUMAN MONOCLONAL ANTIBODIES AGAINST HEPATITIS C VIRUS (VARIANTS)

(71) Applicants: Tatiana Nikolaevna Vlasik, Moscow (RU); Armen Sergeevich Sadgyan, Moscow (RU); Igor Nikolaevich Rybalkin, Moscow (RU); Alexandr Yasenovich Shevelev, Moscow (RU)

(72) Inventors: Tatiana Nikolaevna Vlasik, Moscow (RU); Armen Sergeevich Sadgyan, Moscow (RU); Igor Nikolaevich Rybalkin, Moscow (RU); Alexandr Yasenovich Shevelev, Moscow (RU)

( * ) Notice: Subject to any disclaimer, the term of this patent is extended or adjusted under 35 U.S.C. 154(b) by 420 days.

(21) Appl. No.: 15/107,996

(22) PCT Filed: Aug. 29, 2014

(86) PCT No.: PCT/RU2014/000650
§ 371 (c)(1),
(2) Date: Jan. 3, 2017

(87) PCT Pub. No.: WO2015/099574
PCT Pub. Date: Jul. 2, 2015

(65) Prior Publication Data
US 2017/0121390 A1    May 4, 2017

(30) Foreign Application Priority Data

Dec. 27, 2013   (RU) .................................. 2013158739

(51) Int. Cl.
*A61K 39/42* (2006.01)
*C12N 5/07* (2010.01)
(Continued)

(52) U.S. Cl.
CPC ............ *C07K 16/08* (2013.01); *C07K 16/109* (2013.01); *A61K 2039/507* (2013.01);
(Continued)

(58) Field of Classification Search
None
See application file for complete search history.

(56) References Cited

U.S. PATENT DOCUMENTS

2010/0104555 A1* 4/2010 Law ................... A61K 31/7088
424/130.1
2011/0311550 A1   12/2011 Law et al.
2012/0039846 A1   2/2012 Foung et al.

FOREIGN PATENT DOCUMENTS

WO    WO-0121189 A1 *  3/2001 ........... C07K 14/005
WO    WO2004087760      10/2004
(Continued)

OTHER PUBLICATIONS

Sabo et al., "Neutralizing Monoclonal Antibodies against Hepatitis C Virus E2 Protein Bind Discontinuous Epitopes and Inhibit Infection at a Postattachment Step," Journal of Virology, vol. 85, No. 14: 7005-7019 (Year: 2011).*

(Continued)

Primary Examiner — M Franco G Salvoza
(74) Attorney, Agent, or Firm — Greer, Burns & Crain, Ltd.

(57) ABSTRACT

The invention relates to the field of biotechnology, and specifically to methods and techniques for neutralizing the hepatitis C virus, and specifically to antibodies against the hepatitis C virus, and can be used in medicine, the pharma- (Continued)

ceutical industry and related areas of science and technology. Proposed is the use of fully human monoclonal antibodies—RYB1, RYB2 and RYB3—and of a composition based thereon for the prevention and treatment of hepatitis C. Said antibodies are produced by cultivation using hybrid BIONA-RYB1, BIONA-RYB2 and BIONA-RYB3. The effectiveness of the antibodies is due to said antibodies binding epitopes, namely Ep1, Ep2 and Ep3 of E2 protein of the hepatitis C viral envelope, respectively. The present invention has demonstrated a neutralizing activity of the antibodies in a model system of infection of human cells in a culture. It has been shown that use of the claimed group of inventions provides for more reliable antibody binding of the hepatitis C virus.

16 Claims, 8 Drawing Sheets

Specification includes a Sequence Listing.

(51) Int. Cl.
 C07K 16/08 (2006.01)
 C07K 16/10 (2006.01)
 A61K 39/00 (2006.01)
(52) U.S. Cl.
 CPC ...... C07K 2317/21 (2013.01); C07K 2317/34 (2013.01); C07K 2317/56 (2013.01); C07K 2317/565 (2013.01); C07K 2317/76 (2013.01); C07K 2317/92 (2013.01)

(56) References Cited

FOREIGN PATENT DOCUMENTS

| WO | WO2006100449 | 9/2006 | | |
|---|---|---|---|---|
| WO | WO 2010035292 | 4/2010 | | |
| WO | WO-2010047829 A1 | * | 4/2010 | ........... C07K 14/005 |

OTHER PUBLICATIONS

Rudikoff et al., "Single amino acid substitution altering antigen-binding specificity," Proc Natl Acad Sci USA 79:1979-1983 (Year: 1982).*
Goel et al., "Plasticity within the Antigen-Combining Site May Manifest as Molecular Mimicry in the Humoral Immune Response," J. Immunol. 173: 7358-7367 (Year: 2004).*
Lloyd et al., "Modelling the human immune response: performance of a 1011 human antibody repertoire against a broad panel of therapeutically relevant antigens," Protein Engineering, Design & Selection, vol. 22, No. 3: 159-168 (Year: 2009).*
Edwards et al., "The Remarkable Flexibility of the Human Antibody Repertoire; Isolation of Over One Thousand Different Antibodies to a Single Protein, BLys," J. Mol. Biol. 334: 103-118 (Year: 2003).*
Smith et al., "Rapid generation of fully human monoclonal antibodies specific for a vaccinating antigen," Nat Protoc 4(3): 372-384 (Year: 2009).*
Hanafiah, K., "Global Epidemiology of Hepatitis C Virus Infection: New Estimates of Age-Specific Antibody to HCV Seroprevalence", Hepatology. 2013, 57(4):1333-1342.
Zoulim F, Clinical Consequences of Hepatitis C Virus Infection, Rev Med Virol. 2003, 13(1):57-68.
Chen, S.L., "The Natural History of Hepatitis C. Virus (HCV) Infection", International Journal of Medical Sciences, 2006, 3(2):47-52.
Aceijas, C., "Global estimates of prevalence of HCV infection among injecting drug users", The International Joural of Drug Policy. 2007, (5):352-358.

Kato, N., "Genome of Human Hepatitis C Virus (HCV): Gene Organization, Sequence Diversity, and Variation", Microbial & Comparative Genomics, 2000, 5(3): 129-151.
Niepmann M. "Hepatitis C Virus: From Molecular Virology to Antiviral Therapy", Current Topics in Microbiology and Immunology, 2013, 369:143-166.
Poenisch, M, Ph.D., "New Insights into Structure and Replication of the Hepatitis C Virus and Clinical Implications", Semin Liver Dis. 2010, 30(4):333-347.
Pineiro, C., "RNA Structrual Elements of Hepatitis C Virus Controlling Viral RNA Translation and the Implications for Viral Pathogenesis", Viruses. 2012, 4(10):2233-2250.
Kim, CW, "Hepatitis C virus: virology and life cycle", Clinical and Molecular Hepatology, 2013, 19(1):17-25.
Pawlotsky JM., "The Hepatitis C Virus Life Cycle as a Target for New Antiviral Therapies", Gastroenterology. 2007, 132(5); 1979-1998.
Doyle, JS., "The role of viral and host genetics in natural history and treatment of chronic HCV infection", Best Practice & Research Clinical Gastroenterology, 2012, 26(4):413-427.
Hara, K., "Important Factors in Reliable Determination of Hepatitis C. Virus Genotype by Use of the 5' Untranslated Region", Journal of Clinical Microbiology, 2013, 51(5):1485-1489.
Bukh, J., "Biology and genetic heterogeneity of hepatitis C virus", Clin Exp Rheumatol, 1995, 15(1):41-63.
Inokuchi, M., "Infection of B Cells With Hepatitis C Virus for the Development of Lymphoproliferative Disorders in Patients With Chronic Hepatitis C", Journal of Medical Virology, 2009, 82(12):619-627.
Morsica, G. Replication of Hepatitis C Virus in B Lymphocytes (CD19+), Blood. 1999, 94(3): 1138-1139.
Wong W, "Update on Chronic Hepatitis C", Clinical Gastroenterol. Hepatol. 2005, 3(6):507-520.
Escudero, A., "Pegylated a-interferon-2a plus ribavirin compared with pegylated a-interferon-2b plus ribavirin for initial treatment of chronic hepatitis C virus: Prospective, non-randomized study", Hepatology, 2008, 23(6):861-866.
Abe, H. "New Proposal for Response-Guided Peg-Interferon Plus-Ribavirin Combination Therapy for Chronic Hepatitis C Virus Genotype 2 Infection", Journal of Medical Virology, 2013, 85(9):1523-1533.
Kwo P., "Efficiency of boceprevir, an NS3 protease inhibitor, in combination with peginterferon alfa-2b and ribavirin in treatment-naive patients . . . ", Articles, 2010, 376(9742):705-716.
McHutinson, JG. MD, "Telaprevior for Previously Treated Chronic HCV Infection", The New England Journal of Medecine, 2010, 362 (14):1292-1303.
Janssen, H., "Treatment of HCV Infection by Targeting MicroRNA", The New England Journal of Medicine, 2013, 368(18):1685-1694.
Koberle, V. "Serum microRNA-1 and microRNA-122 are prognostic markers in patients with hepatocellular carcinoma" European Journal of Cancer, 2013, 49(16):3442-3449.
Sautto, G. "New Therapeutic Options for HCV Infection in the Monoclonal Antibody Era", New Microbiol. 2012, 35(4):387-397.
Haberstroh, A., "Neutralizing Host Responses in Hepatitis C Virus Infection Target Viral Entry at Postbinding Steps and Membrane Fusion", Gastroenterology. 2008, 135(5):1719-1728.
Piazza M., "Sexual transmission of the hepatitis C virus and efficacy of prophylaxis with intramuscular immune serum globulin. A randomized controlled trial", JAMA Internal Medicine, 1997, 157(14): 1537-1544.
Pestka JM., "Rapid induction of virus-neutralizing antibodies and viral clearance in a single-source outbreak of hepatitis C", Proc Nati Acad Sci USA. 2007, 104(14):6025-6030.
Di Lorenzo C., "Hepatitis C Virus Evasion Mechanisms from Neutralizing Antibodies", Viruses. 2011, 3(11):2280-2300.
Clementi N, "A Human Monoclonal Antibody with Neutralizing Activity Against Highly Divergent Influenza Subtypes" PLoS One. 2011, 6(12):e28001. dot: 10.1371.
Solforosi L., "A phage display vector optimized for the generation of human antibody combinatorial libraries and the molecular cloning of monoclonal antibody fragments", New Microbiologica, 2012, 35(3):289-294.

(56) References Cited

OTHER PUBLICATIONS

Burioni, R., "Perspectives for the utilization of neutralizing human monoclonal antibodies as anti-HCV drugs", Journal of Hepatology, 2008, 49(2):299-302.

Galun E, "Clinical Evaluation (Phase 1) of a Human Monoclonal Antibody Against Hepatitis C. Virus: Safety and Antiviral Activity", Journal of Hepatology, 2007, 46(1):37-44.

Schiano TD, Charlton M, Younossi Z, Galun E, Pruett T, Tur-Kaspa R, Eren R, Dagan S, Graham N, Williams PV, Andrews J. Liver Transpl. 2006, 12(9): 1381-1389.

Fafi-Kremer S, "Viral Entry and Escape from Antibody-Mediated Neutralizing Influence Hepatitis C Virus Reinfection in Liver Transplantation", J Exp Med. 2010 207(9):2019-2031.

Broering, TJ., "Identification and Characterization of Broadly Neutralizing Human Monoclonal Antibodies against the E2 Envelope Glycoprotein of Hepatitis C. Virus", Journal of Virology, 2009, 83(23): 12473-12482.

Morin, TJ, "Human Monoclonal Antibody HCV1 Effectively Prevents and Treats HCV Infection in Chimpanzees", PLOS Pathogens, 2012; 8(8):e1002895. doi: 10.1371.

Chung RT, "Human Monoclonal Antibody MBL-HCV1 Delays HCV Viral Rebound Following Liver Transplantation a Randomized Controlled Study", American J. of Transplantation and the American Society of Transplant Surgeons, 2013, 13(4): 1047-1054.

Karpas A, "A Human Myeloma Cell Line Suitable for the Generation of Human Monoclonal Antibodies", Proc Nati Acad Sci USA. 2001, 98(4): 1799-1804.

http://www.ncbi.nlm.nih.gov/nuccore, "Hepatitis C virus genotype 1, complete genome", NC_004102.1.

Cocquerel, L, "Coexpression of Hepatitis C Virus Envelope Proteins E1 and E2 in cis Improves the Stability of Membrane Insertion of E2", Journal of General Virology, 2001, 82(7):1629-1635.

Flint, M., "The C-terminal Region of Hepatitis C Virus E1 Glycoprotein Confers Localization Within the Endoplasmic Reticulum", Journal of General Virology, 1999, 80 (8): 1943-1947.

"Antibody Engineering: Methods and Protocols", edited by Benny K. C. Lo 2004, Humana Press Inc., p. 282.

Lafranc MP, "IMGT, the international ImMunoGeneTics database", Nucleic Acids Research, 1999, 27(1):209-212.

http://www.ncbi.nlm.nih.gov/protein, E2 protein [Hepatitis C virus], NP_751921.1.

Bich C, "Reactivity and Applications of New Amine Reactive Cross-Linkers for Mass Spectrometric Detection of Protein-Protein Complexes", American Chemical Society 2010 82(1): 172-179.

Bartosch B, "Infectious Hepatitis C Virus Pseudo-particles Containing Functional E1-E2 Envelope Protein Complexes", J Exp Med. 2003, 197(5):633-642.

\* cited by examiner

METHOD FOR NEUTRALIZING HEPATITIS C VIRUS, FULLY HUMAN MONOCLONAL ANTIBODY AGAINST HEPATITIS C VIRUS (VARIANTS), COMPOSITION OF FULLY HUMAN MONOCLONAL ANTIBODIES AGAINST HEPATITIS C VIRUS AND HYBRID MOUSE/HUMAN PRODUCER CELL LINE OF FULLY HUMAN MONOCLONAL ANTIBODIES AGAINST HEPATITIS C VIRUS (VARIANTS)

The invention relates to the field of biotechnology, specifically to methods and technologies for neutralizing the hepatitis C virus, specifically to antibodies against the hepatitis C virus, and can be used in medicine, the pharmaceutical industry and related fields in science and technology.

Hepatitis C is a widespread and dangerous viral disease. Statistical research has shown that more than 170 million people are affected by hepatitis C (HCV) globally, which is over five times higher than the number affected by the human immunodeficiency virus (HIV). HCV infection is the main cause of hepatocellular carcinoma, and is also the most common reason for liver transplants among adults in Western countries (Mohd Hanafiah K, Groeger J, Flaxman A D, Wiersma S T. Hepatology. 2013, 57(4):1333-1342). HCV infection often occurs without clinical manifestations, notwithstanding inflammation and fibrosis of the liver, which are persistent and progressive and ultimately lead to cirrhosis, liver failure or liver cancer (Zoulim F, Chevallier M, Maynard F, Trepo C. Rev Med Virol. 2003, 13 (1): 57-68). This problem is compounded by the fact that HCV virus often remains in the body permanently: up to 85% of infected people who have the virus suffer chronic infection. All of these reasons make the research for the diagnosis and treatment of hepatitis C highly relevant and practically important.

The hepatitis C Virus (HCV) was first Identified in 1989 (Chen S L, Morgan T R. Int J Med Sci. 2006, 3 (2): 47-52), however the scale of the problem that this infection poses for healthcare and the impact caused by this disease on healthcare has only been fully grasped in recent years with the advent of relatively reliable methods of diagnosis. It is now believed that this virus has spread over several decades or even longer, wherein recent instances of infection are often associated with intravenous drug use and other unidentified factors/methods for transmitting infection (Aceijas C, Rhodes T. Int J Drug Policy. 2007 (5). 352-358). HCV is a small (40-60 nm in diameter), enveloped, single-stranded RNA-containing virus of the *Hepacivirus* genus of the family Flaviviridae. Both the genome of the HCV virus and the proteins encoded by the genes are fully characterized (Kato N. Microb Comp Genomics 2000, 5 (3). 129-151). The positive RNA strand of the viral genome consists of a 5'-untranslated region, an open reading frame of approximately 9,000 nucleotides in length, and a short 3'-untranslated region (FIG. 1). The open reading frame encodes a polypeptide of a length of approximately 3010 amino acids, a so-called "polyprotein", which, during and after translation, is split at several points by host signal peptidases, as well as proteases encoded by HCV (Niepmann M. Curr Top Microbiol Immunol. 2013, 369: 143-166). This splitting results in formation of at least three structural proteins (Core, E1 and E2) and six non-structural (SN) proteins (NS2, NS3, NS4A, NS4B, NS5A H NS5B).

E1 and E2 are two highly glycosylated viral envelope proteins which can interact with plasma membranes of hepatocytes and other cells, mediating the attachment of the virus and its entry into the cell. The E1 and E2 proteins together form heteromeric complexes, but the question of whether these proteins have to associate with each other to bind to cell membranes, has not been solved. The glycoprotein E1 (amino acids 192-383 of the polyprotein) serves as a chaperone for proper folding of the E2 protein during its synthesis, facilitates the binding of E2 to cell surface receptors and is thought to be involved in viral fusion with the cell membrane (Poenisch M, Bartenschlager R. Semin Liver Dis. 2010, 30 (4): 333-347). The E2 glycoprotein (amino acids 384-746 of the polyprotein) contains a hypervariable region at the N-terminal end (amino acids 384-411). NS-proteins are enzymes or auxiliary factors that catalyze and regulate the replication the RNA genome of HCV. The Core protein interacts with the viral RNA and forms a nucleocapsid (Piceiro D, Martinez-Salas E. Viruses 2012, 4 (10): 2233-2250).

The HCV life-cycle model is discussed below (Kim C W, Chang K M. Clin Mol Hepatol. 2013, 19 (1):17-25; Pawlotsky J M, Chevaliez S, McHutchison J G Gastroenterology 2007, 132 (5): 1979-1998). Viral infection begins with the attachment to a cell through a specific interaction between molecules, located on the surface of the target cell, and the viral envelope proteins. HCV attachment to the cell surface is mediated by E2 glycoprotein binding to the receptor CD81 of the tetraspanin family which is expressed on hepatocytes and B-lymphocytes, after which then there is a more specific interaction with one or more "entry" receptors, of which the following are identified: low density lipoprotein receptor, scavenger receptor SR-BI, claudin-1 and occludin. In the next step, the virus enters the cell apparently through receptor-mediated endocytosis. The positive strand of RNA viral genome undergoes translation in the cytoplasm, and nascent polypetide is processed on the membrane of the endoplasmic reticulum.

That is where the replicase is assembled and directs the synthesis of the negative strand RNA, which is then used as a template for the synthesis of molecules of the positive strand RNA. The positive strand RNA is encapsulated by structural proteins and is wrapped by budding into the lumen of the endoplasmic reticulum. Ultimately, infectious virions are released by transport through the Golgi complex.

The HCV genome is characterized by high genetic variability due to the high frequency of replication and lack of editing function of viral replicase. HCV is divided into six major genotypes, the nucleotide sequences of which differ by approximately 30%; currently there are more than 30 subtypes of the virus in the world. The subtypes 1a and 1b are the most common in the United States and Europe, while the most prevalent in the majority of Asian countries is subtype 1b (Doyle J S, Hellard M E, Thompson A J. Best Pract Res Clin Gastroenterol. 2012, 26 (4): 413-427; Nara K, Rivera M M, Koh C, Sakiani S, Hoofnagle J H, Heller T. J Clin microbiol. 2013, 51(5): 1485-1489; Bukh J, Miller R H, Purcell R H. Semin Liver Dis. 1995, 15 (1): 41-63).

HCV virus mainly infects people through hepatocytes, but there is an evidence that HCV is also capable of infecting other organs and cells, particularly the cells of lymphoid organs. Such extrahepatic infection may contribute to the immune-mediated pathogenesis of chronic liver disease and/or the development of autoimmune diseases, including mixed cryoglobulinemia and glomerulonephritis (Inokuchi M, Ito T, Uchikoshi M, Shimozuma Y, Morikawa K, Nozawa H, Shimazaki T, Hiroishi K, Miyakawa Y, Imawari M. J Med Virol. 2009, 82(12):2064-2072; Morsica G, Tambussi G, Sitia G, Novati R, Lazzarin A, Lopalco L, Mukenge S. Blood. 1999, 94(3): 1138-1139).

Modern methods for treating HCV-infection are far from optimal. Interferon-alpha in combination with ribavirin, which are currently used to treat hepatitis C, only makes it possible to obtain the desirable response to treatment in 50% of treated patients; while a significant amount of patients cannot use these drugs because of their adverse effects (Wong W, Terrault N. Clin. Gastroenterol Hepatol. 2005, 3 (6): 507-520.). Furthermore, there is an urgent need for more effective means to prevent the recurrence of hepatitis C in patients who have undergone liver transplantation (recurrence of HCV-infection occurs in virtually 100% of cases in patients who have undergone liver transplantation for terminal liver failure caused by HCV-infection). It has been noted that patients who have undergone transplantation react poorly to treatment by interferon-alpha in combination with ribavirin. Moreover, interferon-alpha can, in some cases, exacerbate transplant rejection (Escudero A, Rodraguez F, Serra M A, Del Olmo J A, Montes F, Rodrigo J M. J Gastroenterol Hepatol. 2008, 23 (6): 861-866; Abe H, Aida Y, Ishiguro H, Yoshizawa K, Seki N, Miyazaki T, Itagaki M, Sutoh S, Ika M, Kato K, Shimada N, Tsubota A, Aizawa Y. J Med Virol. 2013, 85 (9): 1523-1533).

Although over the past several years complications and mortality associated with the hepatitis C have been significantly reduced due to the application of targeted anti-viral preparations, particularly protease inhibitors and reverse transcriptase, the development of new drugs against HCV is facing serious obstacles including the ability of the virus to achieve chronic persistence, genetic diversification which occurs during replication in the host organism, and the emergence of mutant drug resistant forms. Furthermore, it should be taken into account that antiviral drugs can cause adverse side effects.

Many biotechnological and pharmaceutical companies are currently searching for new methods to directly affect already known viral targets, developing preventative and/or therapeutic vaccines against HCV, as well as improving existing therapies based on interferon. Clinical development includes means of treating hepatitis C, which should be safer and more efficient; some of which are modified versions of interferon alpha. The inhibitors in Phase II of clinical development include agents that target the internal ribosome entry site (IRES) of the HCV, NS3 protease and NS5B polymerase. Clinical development of one of the possible NS3 protease inhibitors has been stopped because it had a toxic effect on the heart in mammals, indicating potential problems which could occur during the development of drugs of this type in the future.

Newly developed inhibitors of NS3 protease of the HCV virus (telaprevir and boceprevir) make it possible to increase the frequency of a sustained viral response, but they can be only used in patients infected with HCV genotype 1; in addition, the virus quickly becomes resistant to these drugs (Kwo P Y, Lawitz E J, McCone J, Schiff E R, Vierling J M, Pound D, Davis M N, Galati J S, Gordon S C, Ravendhran N, Rossaro L, Anderson F H, Jacobson I M, Rubin R, Koury K, Pedicone L D, Brass C A, Chaudhri E, Albrecht J K. Lancet. 2010, 376(9742):705-716; McHutchinson J. G., McHutchison J G, Manns M P, Muir A J, Terrault N A, Jacobson I M, Afdhal N H, Heathcote E J, Zeuzem S, Reesink H W, Garg J, Bsharat M, George S, Kauffman R S, Adda N, Di Bisceglie A M. N Engl J Med. 2010, 362(14): 1292-1303).

It is suggested that phosphorothioate-modified oligonucleotide (the preparation miravirsen) can be used to bind and inhibit liver micro-RNA miR-122 which is required for virus replcication (Janssen H L, Reesink H W, Lawitz E J, Zeuzem S, Rodriguez-Torres M, Patel K, van der Meer A J, Patick A K, Chen A, Zhou Y, Persson R, King B D, Kauppinen S, Levin A A, Hodges M R. N Engl J Med. 2013, 368(18): 1685-1694). The disadvantage of similar preparations aimed to reduce the level of miR-122 is the possibility of the formation and accelerated development of malignancies (Koberle V, Kronenberger B, Pleli T, Trojan J, Imelmann E, Peveling-Oberhag J, Welker M W, Elhendawy M, Zeuzem S, Piiper A, Waidmann O. Eur J Cancer. 2013, doi: 10.1016/j.ejca.2013.06.002).

Among the new and more effective treatment methods that have appeared in recent years the most promising is the immunotherapy based on therapeutic monoclonal antibodies specific to HCV proteins (Sautto G A, Diotti R A, Clementi M. New Microbiol. 2012, 35(4):387-397; Haberstroh A, Schnober E K, Zeisel M B, Carolla P, Barth H, Blum H E, Cosset F L, Koutsoudakis G, Bartenschlager R, Union A, Depla E, Owsianka A, Patel A H, Schuster C, Stoll-Keller F, Doffoel M, Dreux M, Baumert T F. Gastroenterology. 2008, 135(5):1719-1728). These developments are based on current reports that antibodies which target the virus are formed in the body of HCV-infected patients. These antibodies may belong to different classes (subclasses) of immunoglobulins and may have different antigen specificity. The functional effects of these antibodies vary from simple binding, with no effect on the virus, to the actual neutralization and elimination of the virus, or the prevention of its reproduction (Piazza M, Sagliocca L, Tosone G, Guadagnino V, Stazi M A, Orlando R, Borgia G, Rosa D, Abrignani S, Palumbo F, Manzin A, Clementi M. Arch Intern Med. 1997, 157(14): 1537-1544). Furthermore, the elimination of the virus is accompanied by a rapid (already in the early stages of infection) generation of broad spectrum neutralizing antibodies. In contrast, antibodies in patients, whose infection has progressed to the chronic phase, have only limited or non-neutralizing activity (Pestka J M, Zeisel M B, Blaser E, Schürmann P, Bartosch B, Cosset F L, Patel A H, Meisel H, Baumert J, Viazov S, Rispeter K, Blum H E, Roggendorf M, Baumert T F. Proc Natl Acad Sci USA. 2007, 104(14):6025-6030). It can be assumed that the ineffectiveness of an antibody response against HCV is caused by a general imbalance in humoral immune response (Di Lorenzo C, Angus A. G., Patel A. H. Viruses. 2011, 3(11):2280-2300).

The therapeutic potential of antibodies is largely dependent on their specific targets—viral protein epitopes with which they can react. Although antibodies against non-structural HCV proteins are reported in people with hepatitis C, these antibodies usually do not have a significant effect on the virus. On the other hand, antibodies directed against structural proteins, especially against E1 and E2 envelope proteins, may manifest neutralizing activity by blocking viral entry into the cells or triggering mechanisms of antibody-dependent cell-mediated cytotoxicity (ADCC) and complement-dependent lysis (CDL), leading to its destruction. Therefore, it can be expected that one of the most promising approaches to the generation of new drugs for hepatitis C treatment is the production and testing of human monoclonal antibodies against conservative regions of structural viral proteins based on natural antibodies developed in HCV-infected patients (Clementi N, De Marco D, Mancini N, Solforosi L, Moreno G J, Gubareva L V, Mishin V, Di Pietro A, Vicenzi E, Siccardi A G, Clementi M, Burioni R. PLoS One. 2011, 6(12):e28001. doi: 10.1371; Solforosi L, Mancini N, Canducci F, Clementi N, Sautto G A, Diotti R A, Clementi M, Burioni R. New Microbiol. 2012, 35(3):289-294). Thus it can be expected that monoclonal antibodies acting directly on the virus would reduce the virus level in blood and prevent reinfection of new liver cells (Burioni R, Perotti M, Mancini N, Clementi M. J. Hepatol. 2008, 49 (2): 299-300). Furthermore, the introduction of specific monoclonal antibodies or antibody cocktails against HCV may restore the balance in favor of the immune system and prevent the spread of the virus.

It is known that several drugs based on monoclonal antibodies against the E2 protein are currently undergoing Phase I or Phase II clinical trials. In particular, Phase I clinical trials of human monoclonal antibody XTL-002 showed that more than half of the 15 patients with hepatitis C who underwent single intravenous infusion of XTL-002, showed a significant decrease in viral load, from 2 to 100 times; while no serious side effects were observed. Two clinical studies for the prevention of HCV reinfection in patients with chronic infection during and after liver transplantation showed a moderate and short-term decrease in viremia after infusion of human antibody XTL68 against the E2 protein of HCV virus (Galun E, Terrault N A, Eren R, Zauberman A, Nussbaum Oh, Terkieltaub D, Zohar M, Buchnik R, Ackerman Z, Safadi R, Ashur Y, Misrachi S, Liberman Y, Rivkin L, Dagan S. J. Hepatol 2007, 46 (1): 37-44; Schiano T D, Charlton M., Younossi Z, Galun E, Pruett T, Tur-Kaspa R, Eren R, Dagan S, Graham N, Williams P V, Andrews J. Liver Transpl. 2006, 12 (9): 1381-1389). Another clinical trial was started in Strasbourg for the prevention of reinfection of a liver transplant using monoclonal antibodies (Fafi-Kremer S, Fofana I, Soulier E, Carolla P, Meuleman P, Leroux-Roels G, Patel A H, Cosset F L, Pessaux P, Doffoël M, Wolf P, Stoll-Keller F, Baumert T F. J Exp Med. 2010 207(9):2019-2031).

Transgenic mice were used in the development of the humanized monoclonal antibody MBL-HCV1, directed against the highly conserved linear epitope of HCV E2 envelope glycoprotein (amino acids 412-423) and capable of the in vitro neutralization of HCV of various genotypes (Broering T J, Garrity K A, Boatright N K, Sloan S E, Sandor F, Thomas W D Jr, Szabo G, Finberg R W, Ambrosino D M, Babcock G J. J. Virol. 2009, 83(23): 12473-12482). In a dose range selection study, which was carried out on chimpanzees, a single injection of this antibody in a dose of 250 mg/kg prevented an acute HCV-infection (Morin T J, Broering T J, Leav B A, Blair B M, Rowley K J, Boucher E N, Wang Y, Cheslock P S, Knauber M, Olsen D B, Ludmerer S W, Szabo G, Finberg R W, Purcell R H, Lanford R E, Ambrosino D M, Molrine D C, Babcock G J. PLoS Pathog. 2012; 8 (8):e1002895 doi: 10.1371).

A randomized trial was conducted to study the effect of repeated injections of MBL-HCV1 on the elimination of HCV in patients who have undergone liver transplantation. The Phase I study completed in 2009, which involved 31 healthy volunteers, showed that the antibody is well tolerated and does not cause serious side effects. Subjects infected with HCV genotype 1a virus received 11 infusions of the antibody in a dose of 50 mg/kg/day (up to 14 days after transplantation of the liver). The reduction in viral load from baseline was significantly greater in patients who received the antibody than in subjects who received a placebo. Furthermore, the period for recovering the viral load in the group with the antibody was considerably longer than in placebo group (18.7 days versus 2.4 days). However, as in the case of monotherapy with other medication for HCV infection, there were resistant variants of the virus found among patients receiving the antibody. This may be due to the fact that the epitope for this antibody is very close to the hypervariable region of HCV E2 protein (Chung R T, Gordon F D, Curry M P, Schiano T D, Emre S, Corey K, Markmann J F, Hertl M, Pomposellill, Pomfret E A, Florman S, Schilsky M, Broering T J, Finberg R W, Szabo G, Zamore P D, Khettry U, Babcock G J, Ambrosino D M, Ieav B, Leney M, Smith H L, Molrine D C. American J. of Transpl. 2013 13 (4): 1047-1054).

Crucell Ltd. has developed a program for combining various antibodies against the hepatitis C virus. Currently, it is assessing a large panel of fully human monoclonal antibodies against the hepatitis C virus with special attention to specific regions of the protein E2 of HCV.

Human monoclonal antibodies against HCV are most usually generated based on recombinant DNA technology using libraries of variable domains of light and heavy chains of human immunoglobulins or with the aid of hybrid cell cultures which are the result of the fusion of blood lymphocytes of an infected person and a suitable "partner" cell line (Karpas A, Dremucheva A, Czepulkowski H V Proc Natl Acad Sci USA. 2001, 98 (4): 1799-1804). An alternative approach may be "humanizing" mouse monoclonal antibodies against HCV.

However, analysis of the literature has shown that the existing development is not comprehensive enough and currently does not make it possible to obtain sufficiently reliable results for the diagnosis of HCV and treatment of the disease caused by HCV.

The group of inventions (US20120039846, 2012) is the closest in terms of essence and the effect to be obtained and includes compositions for preventing and treating HCV. The composition includes one or more human monoclonal antibodies directed against conformational epitopes of E2 protein of hepatitis C viral envelope, namely the monoclonal antibody HC-11 secreted by the hybridoma cell line stored in the ATCC collection under registration number PTA-9418, or a fragment thereof, which comprises a heavy chain CDR1 region comprising sequence GATFSSFI (SEQ ID NO: 37), a heavy chain CDR2 region comprising sequence IIPMFGTA (SEQ ID NO: 38), a heavy chain CDR3 region comprising sequence AMEVPGFCRGGSCSGYMDV (SEQ ID NO: 39), a light chain CDR1 region comprising sequence HSVSSSN (SEQ ID NO: 40), a light chain CDR2 region comprising sequence GAS (SEQ ID NO: 41) and a light chain CDR3 region comprising sequence QQYGSSPIT (SEQ ID NO: 42); the monoclonal antibody HC-1 secreted by the hybridoma cell line stored in a ATCC collection under registration number PTA-9416, or a fragment thereof, comprising a heavy chain CDR1 region comprising sequence GGTYNSEV (SEQ ID NO: 43), a heavy chain CDR2 region comprising sequence FIPMFGTA (SEQ ID NO: 44), a heavy chain CDR3 region comprising sequence AKVLQVGGN-LVVRPL (SEQ ID NO: 45), a light chain CDR1 region comprising sequence QTISSTH (SEQ ID NO: 46), a light chain CDR2 region comprising sequence GVS (SEQ ID NO: 47) and a light chain CDR3 region comprising sequence HQYGNSPQT (SEQ ID NO: 48); the monoclonal antibody HC-3 secreted by the hybridoma cell line stored in a ATCC collection under registration number PTA-9417, or a fragment thereof, which comprises a heavy chain CDR1 region comprising sequence GFSLSTTGVG (SEQ ID NO: 49), a heavy chain CDR2 region comprising sequence IYWDDDK (SEQ ID NO: 50), a heavy chain CDR3 region comprising sequence ALNSYRSGTILYRELELRGLFYI (SEQ ID NO: 51), a light chain CDR1 region comprising sequence QSISSW (SEQ ID NO: 52), a light chain CDR2 region comprising sequence ESS (SEQ ID NO: 53) and a light chain CDR3 region comprising sequence QQYESSSWT (SEQ ID NO: 54; and the monoclonal antibody CBH-23 secreted by the hybridoma cell line stored in a ATCC collection under registration number PTA-9419, or a fragment thereof, comprising a heavy chain CDR1 region comprising sequence GGTFSSYA (SEQ ID NO: 55), a heavy chain CDR2 region comprising sequence IVPMF-GTE (SEQ ID NO: 56), a heavy chain CDR3 region comprising sequence ARHENIYGTPFDY (SEQ ID NO: 57), a light chain CDR1 region comprising sequence HSI-TRY (SEQ ID NO: 58), a light chain CDR2 region comprising sequence AAS (SEQ ID NO: 59) and a light chain CDR3 region comprising sequence QQSYSTLLT (SEQ ID NO: 60).

In addition to antibodies, the prior art includes cell lines which produce same, as well as pharmaceutical compositions based thereon. The epitopes of these antibodies are conformational. The authors have shown that the epitope for the antibody HC-11 includes the amino acids Gly530 and Asp535 of the E2 protein, which contact the antibody; the epitope for the HC-1 antibody includes contacting amino acids Trp529, Gly530 and Asp535; the epitope for the HC-3 antibody includes contacting amino acids Arg657, Asp658, Phe679, Leu692, Ile696 and Asp698. (Hereinafter, the numbering of amino acids corresponds to the sequence of the polyprotein of the hepatitis C virus isolate H77 of genotype 1a—reference number NP_671491.1 in the international NCBI Protein database).

The disadvantage of this group of inventions is that the proposed compositions do not cover all the epitopes of the E2 protein which may induce the virus neutralizing antibodies, and therefore these can be expected to have insufficient effectiveness in blocking viral replication.

The problem to be solved by the claimed group of inventions is to increase effectiveness in neutralizing the hepatitis C virus. The solution to this problem is based on the fact that, to date, a series of E2 protein epitopes are characterized for human monoclonal antibodies having HCV neutralizing activity, namely linear epitopes with coordinates 412-423 (WO 2006100449, 2006); 480-494, and 613-621 (WO 2004087760, 2004); continuous conformational epitopes with coordinates 396-424, 412-424, 436-447 and 523-540 (US 20110311550, 2011); discontinuous conformational epitopes containing the amino acids Leu641, Thr648, Pro512, Leu580, Pro591 and Arg588 (WO2010035292, 2010), as well as the above mentioned epitopes presented in the invention (US20120039846, 2012). The analysis has shown that some regions of the amino acid sequence of the protein E2 do not contain the described epitopes. In particular, antibodies with epitopes on the regions 448-479, 494-511, 541-579, 592-612, and 622-640 are not known. It could be assumed that the antibodies to these epitopes could have new properties and may potentially be more effective for the prevention and treatment of hepatitis C.

The technical goal was to increase the range of antibodies that are suitable to affect the hepatitis C virus by generating human monoclonal antibodies to the E2 viral envelope protein, which have neutralizing activity and directed at new and not previously described epitopes, and improving the reliability in the binding of hepatitis C viruses. Furthermore, the term "epitope" in the text of the present invention refers to the portion of the polypeptide molecule of E2 protein that is recognized by any of the described monoclonal antibodies and comes into direct contact therewith. The epitope can be a continuous amino acid sequence, or may be discontinuous, i.e. composed of a series of amino acids that are far from each other in terms of serial number, but closely spaced in the 3-dimensional structure of the protein.

The linear and conformational epitopes also differ. In the linear epitopes, the recognition of the epitope by the antibody is determined only by the amino acid sequence of the epitope, and in the conformational epitopes, the recognition also depends on the conformational structure of the epitope in the composition of the protein molecule. The technical result was achieved by generating antibodies capable of binding to epitopes, hereinafter identified as epitopes Ep1 and/or Ep2 and/or Ep3, which include amino acid sequences of variable regions of the heavy ($V_H$) and light ($V_L$) chains thereof:

the sequence of the $V_H$ region of the antibody RYB1, SEQ ID NO: 5;
the sequence of the $V_L$ region of the antibody RYB1, SEQ ID NO: 9;
the sequence of the $V_H$ region of the antibody RYB2, SEQ ID NO: 13;
the sequence of the $V_L$ region of the antibody RYB2, SEQ ID NO: 17;
the sequence of the $V_H$ region of the antibody RYB3, SEQ ID NO: 21; and
the sequence of the $V_L$ region of the antibody RYB3, SEQ ID NO: 25.

Thus, the following composition is generally used to inhibit the virus: three antibodies designated as RYB1, RYB2 and RYB3, at ratios (% wt.) RYB1:RYB2:RYB3=20-40:20-40:20-40. Best results were achieved when the composition ratio of the ingredients was 1:1:1. Reducing the concentration of one of the ingredients to less than 20% is undesirable because of the increased likelihood of reduced effectiveness against the virus because of the variability of its genotype, although there is an effect, albeit less pronounced, when using the aforementioned antibodies at a lower concentration or even individually as one of the effect variants to keep the virus from spreading.

It has been established that the epitope for an antibody RYB1, which is referred to as epitope Ep1, constitutes a certain conformation of an amino acid sequence contained within the region HPEATYSRCG (589-598, SEQ ID NO: 30) and comprising amino acids Ser595 and Arg596. In addition, the central portion of this fragment of 6 amino acids is the most significant: EATYSR (591-596, SEQ ID NO: 31). This epitope is not described in the literature.

The epitope of the antibody RYB2, which is referred to as epitope Ep2, constitutes a certain conformation of an amino acid sequence contained within the region VCGPVYCF (502-509, SEQ ID NO: 32) and comprising the amino acid Tyr507. In addition, the central portion of this fragment of 6 amino acids is the most significant: CGPVYC (503-508, SEQ ID NO: 33). This epitope is not described in the literature.

The epitope of the antibody RYB3, which is referred to as epitope Ep3, constitutes a certain conformation of an amino acid sequence contained within the region HPEATYS-RCGSGPWITP (589-605, SEQ ID NO: 34) and comprising the amino acids Ser595, Arg596 and Ser599. In addition, one of the inner fragments of this region is the most significant: YSRCGS (594-599, SEQ ID NO: 35) or SRCGSG (595-600, SEQ ID NO: 36). This epitope is not described in the literature.

These antibodies were generated by creating hybrid cell lines (hybridoma) BIONA-RYB1, BIONA-RYB2 and BIONA-RYB3 which produce the above antibodies. The claimed hybridomas were deposited on 17 Jul. 2013 in the Russian National Collection of Industrial Microorganisms under the identifiers H-142, H-143 and H-144, and have the following characteristics.

Strain BIONA-RYB1 (registration number H-142)
Antibody title: RYB1.
Class/sub. class of antibody: human IgG1 (kappa).
The immunogen used to produce the antibody: the hepatitis C virus (natural infection).
Antibody specificity: E2 protein of the hepatitis C viral envelope.
Known cross-reaction: all genotypes of the hepatitis C virus.
Strain age: 12 months.
Place of origin: Moscow, BionA Pharma LLC, the strain does not have a predecessor and has not been previously deposited.
Partners for the hybridization of cells: mononuclear cells isolated from the spleen of a patient who died from hepatitis C, and is owned by BionA Pharma LLC, and a hybrid (mouse/human) myeloma cell line BIONA-X.
Cultural properties of the strain, marker signs: suspension culture of lymphocyte-like cells, the strain markers were not determined.
Recommended conditions for freezing: the strain cells were pelleted by centrifugation for 15 minutes at 200 g, re-suspended in fetal calf serum containing 10% dimethyl sulfoxide to a concentration of $3\times10^6$ cells/ml, dispensed into 2 ml plastic vials for cryopreservation (COSTAR-CORNING) and placed in a STRATAGENE container for slow freezing and pre-cooled to 4° C. The container is kept in a low temperature freezer at −70° C. for 24 hours, after which the vials with the cells are transferred into liquid nitrogen. Programmed freezing can be carried out by reducing the temperature by 1° C. per minute to −4° C. with the transfer into liquid nitrogen. Thawing quickly at 37° C. After thawing, the vial contents is transferred to a 10 ml serum-free medium DMEM, pelleted by centrifugation, re-suspended in a 5 ml culture medium and transferred to a culture flask. Cell viability, determined by trypan blue incorporation, is more than 80%.
Recommended culture conditions. DMEM culture medium with the addition of 10% fetal bovine serum, 4 mM L-glutamine, 1 mM Na-pyruvate, 100 IU/ml penicillin, 100 µg/ml streptomycin and a concentrate of amino acids and vitamins for Basal Eagle Medium. Standard tissue culture flasks are used for growing the strain. $1\times10^6$ cells are inoculated in 5 ml of medium in a 25 cm$^2$ area flask. Cultivation is carried out at 37° C. in an atmosphere of 5.6% $CO_2$. When the culture density reaches $1\times10^6$ cells/ml the passage 1:5 is to be performed by replacing 4 ml of cell suspension with 4 ml of fresh culture medium.
Contamination: no bacteria, fungi or *mycoplasma* were visually identified in the culture over a prolonged observation.
The obtained product: a fully human monoclonal antibody RYB1 of IgG1 (kappa) class, which is specific to the E2 protein of the hepatitis C viral envelope.
Field of application of the strain: the creation of a therapeutic agent for treating hepatitis C.
Activity (productivity) of the strain (indicating the culture conditions), as well as other performance indicators: while cultivated under standard conditions for 3 days, human IgG1 concentration in the culture medium reaches 20 µg/ml.
A method for determining the activity of the strain, indicating the process: measuring human IgG1 in the culture conditioned medium by enzyme-linked immunosorbent assay (ELISA) using appropriate ELISA kit (e.g., ELH-IGG1-001 Human IgG1 ELISA kit, Raybiotech, USA).

Strain BIONA-RYB2 (registration number H-143)
Antibody title: RYB2.
Class/sub. class of antibody: human IgG1 (kappa).
The immunogen used to produce the antibody: the hepatitis C virus (natural infection).
Antibody specificity: E2 protein of the hepatitis C viral envelope.
Known cross-reaction: all genotypes of the hepatitis C virus.
Strain age: 12 months.
Place of origin: Moscow, BionA Pharma LLC, the strain does not have a predecessor and has not been previously deposited.
Partners for the hybridization of cells: mononuclear cells isolated from the spleen of a patient who died from hepatitis C, and is owned by BionA Pharma LLC, and a hybrid (mouse/human) myeloma cell line BIONA-X.
Cultural properties of the strain, marker signs: suspension culture of lymphocyte-like cells, the strain markers were not determined.
Recommended conditions for freezing: the strain cells were pelleted by centrifugation for 15 minutes at 200 g, re-suspended in fetal calf serum containing 10% dimethyl sulfoxide to a concentration of $3\times10^6$ cells/ml, dispensed into 2 ml plastic vials for cryopreservation (COSTAR-CORNING) and placed in a STRATAGENE container for slow freezing and pre-cooled to 4° C. The container is kept in a low temperature freezer at −70° C. for 24 hours, after which the vials with the cells are transferred into liquid nitrogen. Programmed freezing can be carried out by reducing the temperature by 1° C. per minute to −4° C. with the transfer into liquid nitrogen. Thawing quickly at 37° C. After thawing, the vial contents is transferred to a 10 ml serum-free medium DMEM, pelleted by centrifugation, re-suspended in a 5 ml culture medium and transferred to a culture flask. Cell viability, determined by trypan blue incorporation, is more than 85%. Recommended culture conditions. DMEM culture medium with the addition of 10% fetal bovine serum, 4 mM L-glutamine, 1 mM Na-pyruvate, 100 IU/ml penicillin, 100 µg/ml streptomycin and a concentrate of amino acids and vitamins for Basal Eagle Medium. Standard tissue culture flasks are used for growing the strain. $1\times10^6$ cells are inoculated in 5 ml of medium in a 25 cm$^2$ area flask. Cultivation is carried out at 37° C. in an atmosphere of 5.6% $CO_2$. When the culture density reaches $1\times10^6$ cells/ml passage 1:5 is to be performed by replacing 4 ml of cell suspension with 4 ml of fresh culture medium.
Contamination: no bacteria, fungi or *mycoplasma* were visually identified in the culture over a prolonged observation.
The obtained product: a fully human monoclonal antibody RYB2 of IgG1 (kappa) class, which is specific to the E2 protein of the hepatitis C viral envelope.
Field of application of the strain: the creation of a therapeutic agent for treating hepatitis C.
Activity (productivity) of the strain (indicating the culture conditions), as well as other performance indicators: while cultivated under standard conditions for 3 days, human IgG1 concentration in the culture medium reaches 20 µg/ml.
A method for determining the activity of the strain indicating the process: measuring human IgG1 in the culture conditioned medium by enzyme-linked immunosorbent assay (ELISA) using appropriate ELIZA kit (e.g., ELH-IGG1-001 Human IgG1 ELISA kit, Raybiotech, USA).

Strain BIONA-RYB3 (registration number H-144)
Antibody title: RYB3.
Class/sub. class of antibody: human IgG1 (kappa).
The immunogen used to produce the antibody: the hepatitis C virus (natural infection).

Antibody specificity: E2 protein of the hepatitis C viral envelope.

Known cross-reaction: all genotypes of the hepatitis C virus.

Strain age: 12 months.

Place of origin: Moscow, BionA Pharma LLC, the strain does not have a predecessor and has not been previously deposited.

Partners for the hybridization of cells: mononuclear cells isolated from the spleen of a patient who died from hepatitis C, and is owned by BionA Pharma LLC, and a hybrid (mouse/human) myeloma cell line BIONA-X.

Cultural properties of the strain, marker signs: semi-suspension culture of lymphocyte-like cells, the strain markers were not determined.

Recommended conditions for freezing: the strain cells were pelleted by centrifugation for 15 minutes at 200 g, re-suspended in fetal calf serum containing 10% dimethyl sulfoxide to a concentration of $3\times10^6$ cells/ml, dispensed into 2 ml plastic vials for cryopreservation (COSTAR-CORNING) and placed in a STRATAGENE container for slow freezing and pre-cooled to 4° C. The container is kept in a low temperature freezer at −70° C. for 24 hours, after which the vials with the cells are transferred into liquid nitrogen. Programmed freezing can be carried out by reducing the temperature by 1° C. per minute to −4° C. with the transfer into liquid nitrogen. Thawing quickly at 37° C. After thawing, the vial contents is transferred to a 10 ml serum-free medium DMEM, pelleted by centrifugation, re-suspended in a 5 ml culture medium and transferred to a culture flask. Cell viability, determined by trypan blue incorporation, is more than 70%.

Recommended culture conditions. DMEM culture medium with the addition of 10% fetal bovine serum, 4 mM L-glutamine, 1 mM Na-pyruvate, 100 IU/ml penicillin, 100 μg/ml streptomycin and a concentrate of amino acids and vitamins for Basal Eagle Medium. Standard tissue culture flasks are used for growing the strain. $1\times10^6$ cells are inoculated in 5 ml of medium in a 25 cm² area flask. Cultivation is carried out at 37° C. in an atmosphere of 5.6% $CO_2$. When the culture density reaches $1\times10^6$ cells/ml the passage 1:5 is to be performed by transferring the medium with floating cells into a sterile tube, removing the attached cells using trypsin, combining with the floating cells and removing one fifth of the combined cell suspension for a new inoculation.

Contamination: no bacteria, fungi or *mycoplasma* were visually identified in the culture over a prolonged observation.

The obtained product: a fully human monoclonal antibody RYB3 of IgG1 (kappa) class, which is specific to the E2 protein of a hepatitis C viral envelope.

Field of application of the strain: the creation of a therapeutic agent for treating hepatitis C.

Activity (productivity) of the strain (indicating the culture conditions), as well as other performance indicators: while cultivated under standard conditions for 3 days, human IgG1 concentration in the culture medium reaches 30 μg/ml.

A method for determining the activity of the strain indicating the process: measuring human IgG1 in the culture conditioned medium by enzyme-linked immunosorbent assay (ELISA) using appropriate ELISA kit (e.g., ELH-IGG1-001 Human IgG1 ELISA kit, Raybiotech, USA).

The essence of the claimed inventions is illustrated by the following graphic materials:

FIG. 1 shows the structure of the genome of the hepatitis C virus. A rectangular frame contains the region which encodes the polyprotein. The hairpin regions correspond to the 5'- and 3'-untranslated regions, which include an internal ribosome entry site (IRES). Genomic regions which encode the protein products formed during splitting the polyprotein by cellular and viral peptidases are marked. The known functions of each protein product are indicated. The coordinates of the viral genome coding for regions of the virus isolate H77 (genotype 1a) are: nucleotides 342-914—Core structural protein, nucleotides 342-828-gp2 protein (formed as a result of a translational frameshift), nucleotides 915-1490—structural protein E1, nucleotides 1491-2579—structural protein E2, nucleotides 2580-2768—p7 protein (localized on the membrane), nucleotides 2769-3419—NS2 protein (membrane protein, inhibitor of CIDE-B induced apoptosis), nucleotides 3420-5312—NS3 protein (protease/helicase), nucleotides 5313-5474—NS4A protein (cofactor for NS3 protease), nucleotides 5475-6257—NS4B protein (membrane protein regulator of replication complex NS3-NS5B), nucleotides 6258-7601—NS5A protein (capable of phosphorylation, likely mediates sensitivity to interferon), and nucleotides 7602-9374—NS5B protein (RNA-dependent RNA polymerase). The genome regions 1-341 and 9378-9646 are, respectively, 5- and 3-non-coding.

Figure 4:
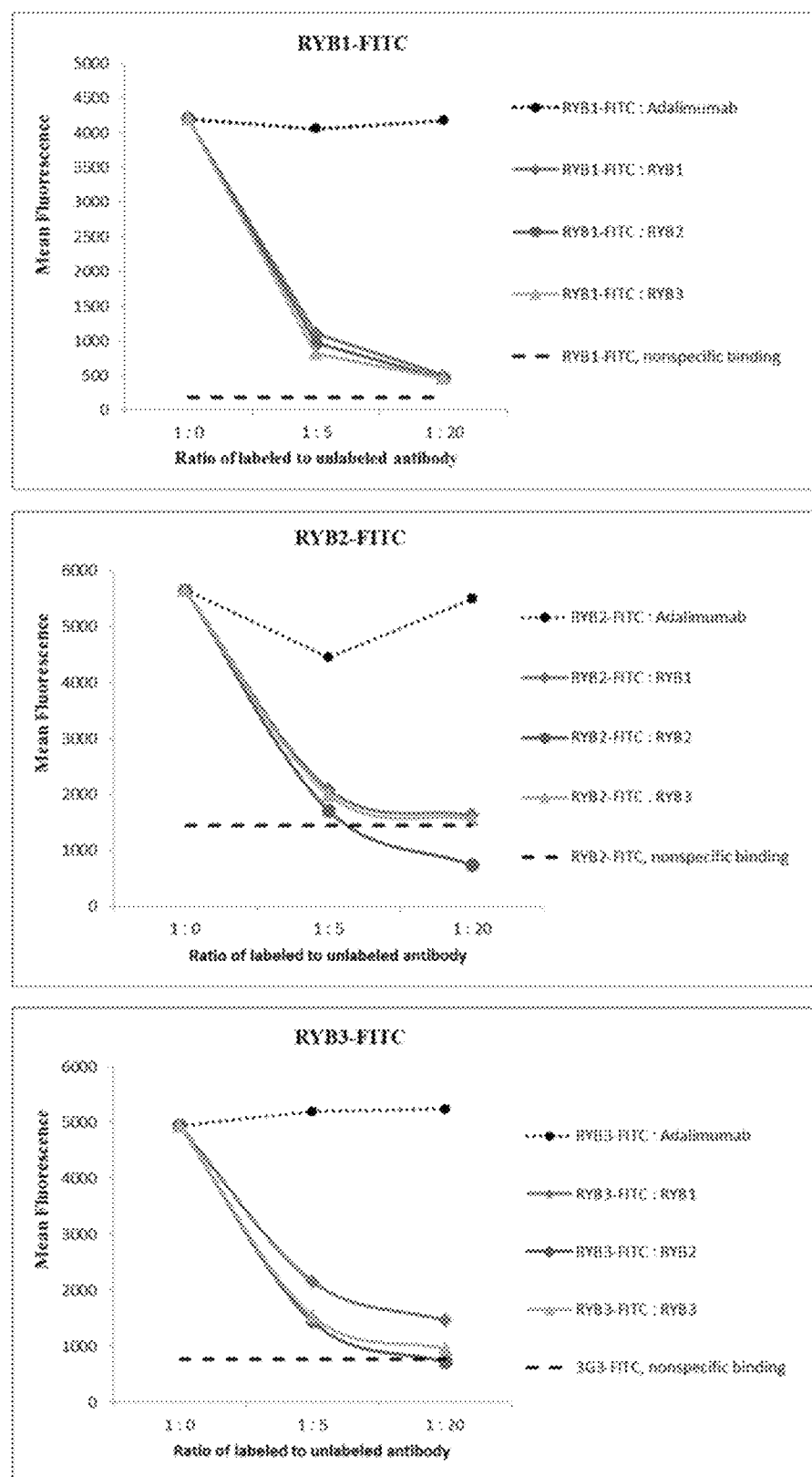

FIG. 4 shows the mutual competition of the antibodies RYB1, RYB2 and RYB3 for binding to HEK-E1E2 cells expressing the E1-E2 of HCV protein complex. The graphs show the average fluorescence values for the cells after the binding reaction with mixtures with FITC-labelled and unlabeled antibodies at the indicated ratios. Nonspecific binding was measured using HEK293 cells.

Figure 5:
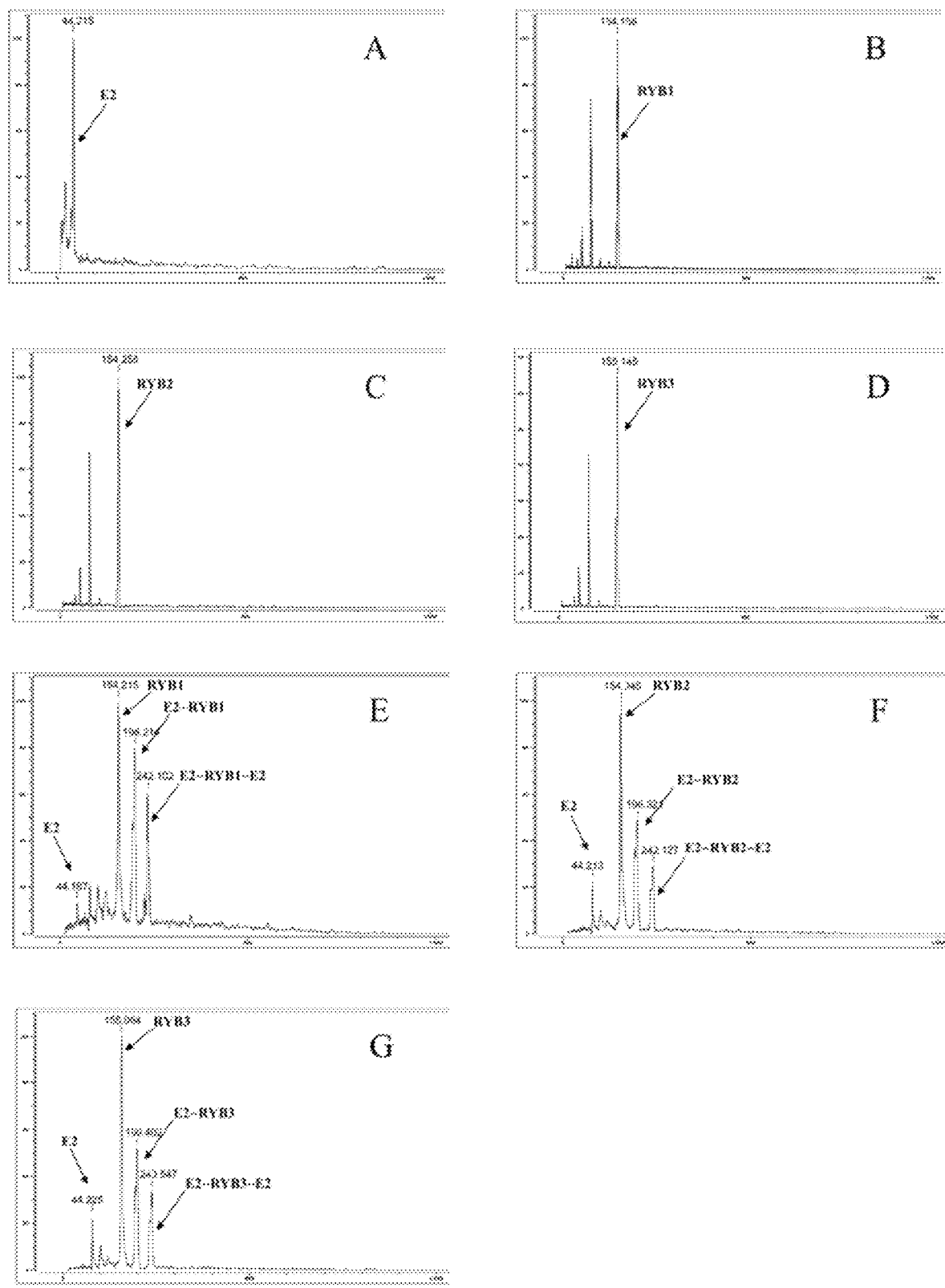

FIG. 5 shows the mass spectra of E2 recombinant protein complexes with antibodies RYB1, RYB2 and RYB3, where A: pure E2 protein; B-D: preparations of the corresponding antibodies RYB1, RYB2 and RYB3; and E-G: complexes of antibodies with E2 protein.

Figure 6:
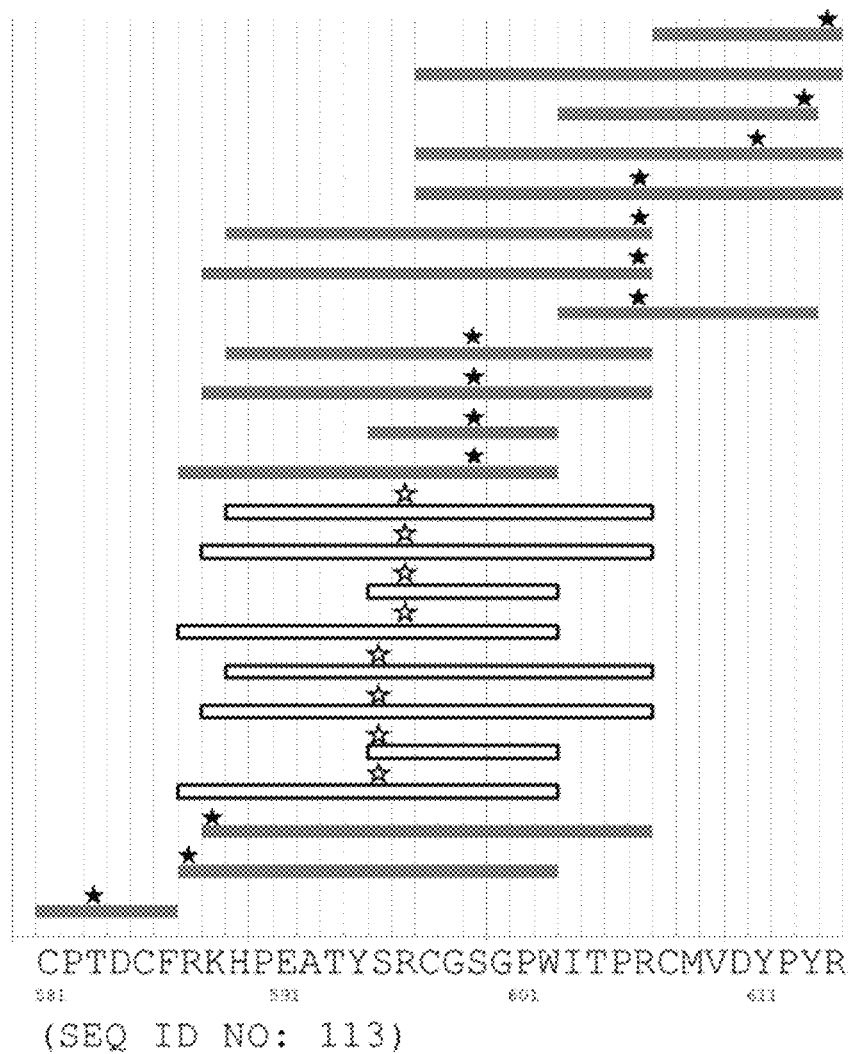

FIG. 6 demonstrates the arrangement of crosslinking reagent molecules on the peptide products of the E2 protein proteolysis in the vicinity of the epitope for the antibody RYB1 before and after the formation of complexes with the antibody. The dark rectangles correspond to peptides present among the proteolysis products of both pure E2 protein and its complexes with antibody RYB1. Amino acids associated with the crosslinking reagent are marked by a dark star. The light rectangles correspond to peptides present among pure E2 protein proteolysis products, but absent after the formation of a complex with the antibody. Amino acids associated with the crosslinking reagent in the case of pure E2 protein proteolysis are marked by a light star. The amino acid sequence of the E2 protein of the analyzed region is shown along the horizontal axis.

Figure 7:
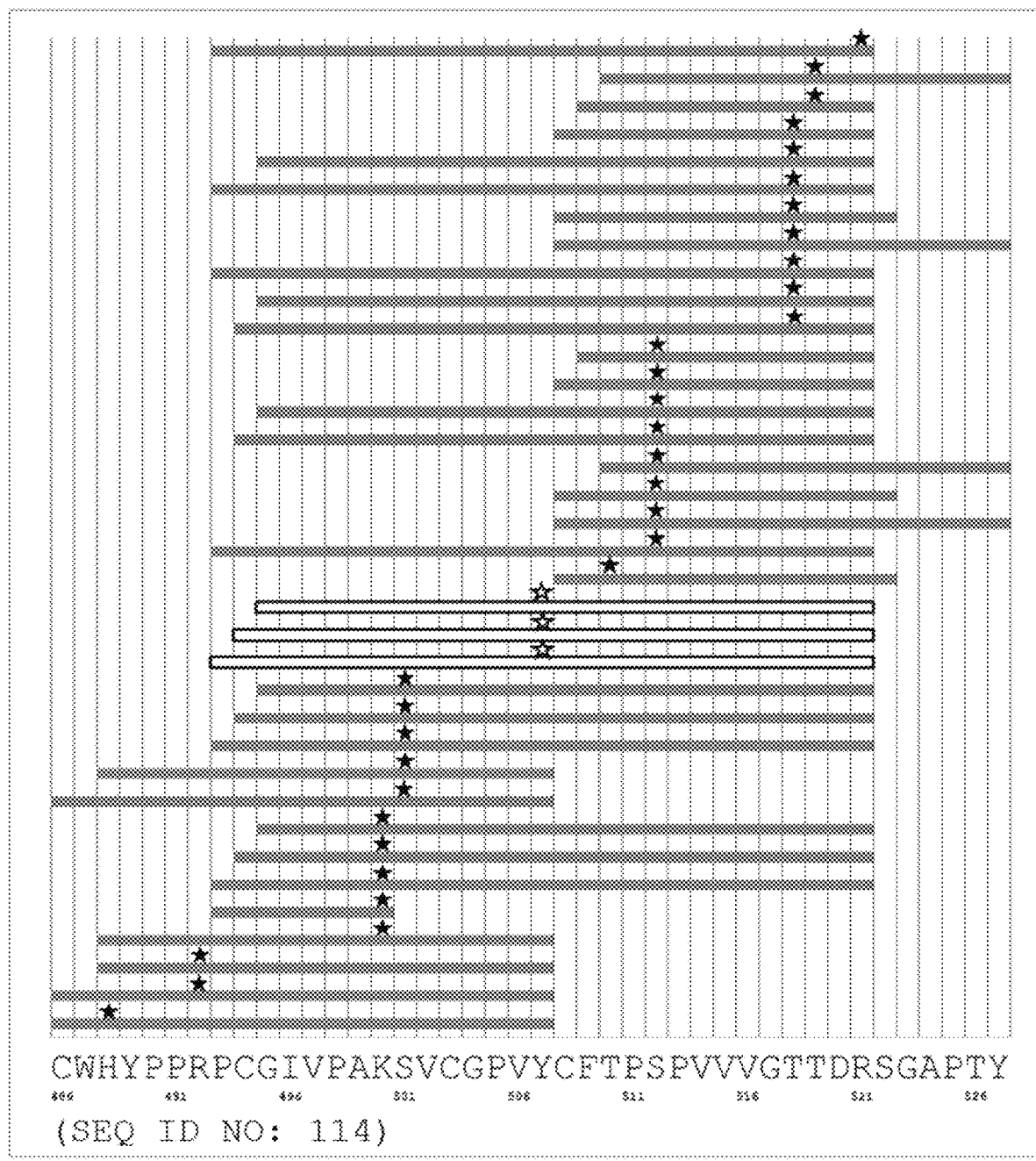

FIG. 7 shows the arrangement of the cross-linking reagent molecules on the peptide products of the E2 protein proteolysis in the vicinity of the epitope for antibody RYB2 before and after the formation of complexes with the antibody. The dark rectangles correspond to peptides present among the proteolysis products of both pure E2 protein and its complexes with antibody RYB2. The amino acids associated with the crosslinking reagent are denoted by a dark star. The light rectangles correspond to peptides present among the proteolysis products of pure E2 protein, but absent after the formation of a complex with the antibody. The amino acids associated with the crosslinking reagent in the case of proteolysis of pure E2 protein are denoted by a light star. The amino acid sequence of the E2 protein of the analyzed region is shown along the horizontal axis.

Figure 8:
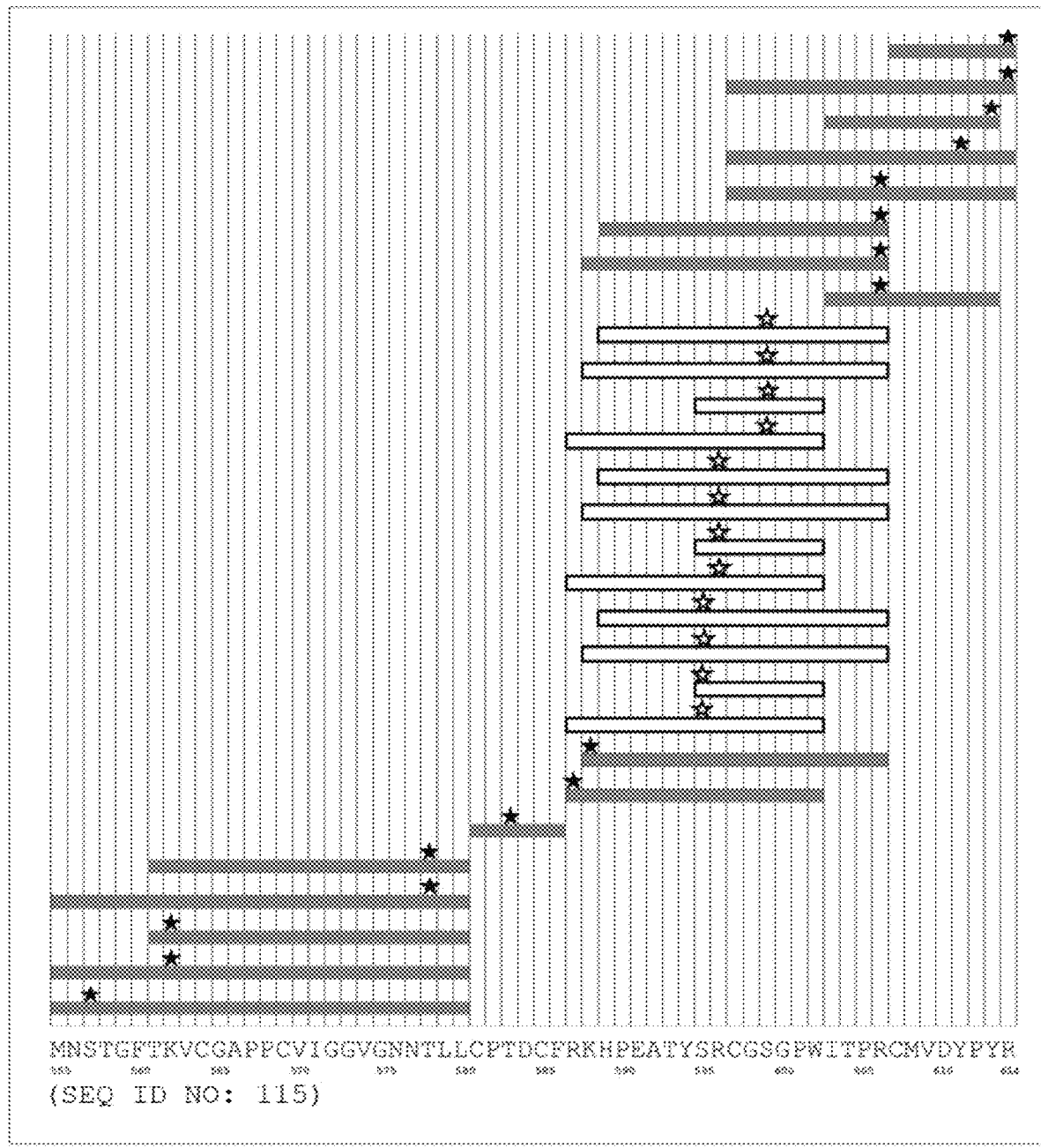

FIG. 8 shows the arrangement of the cross-linking reagent molecules on the peptide products of the E2 protein proteolysis in the vicinity of the epitope for antibody RYB3 before and after the formation of complexes with the antibody. The dark rectangles correspond to peptides present among the proteolysis products of both pure E2 protein and its complexes with antibody RYB3. The amino acids associated with the crosslinking reagent are denoted by a dark star. The light rectangles correspond to peptides present among the proteolysis products of pure E2 protein, but absent after the formation of a complex with the antibody. The amino acids associated with the crosslinking reagent in the case of proteolysis of pure E2 protein are denoted by a light star. The amino acid sequence of the E2 protein of the analyzed region is shown along the horizontal axis.

Figure 9:
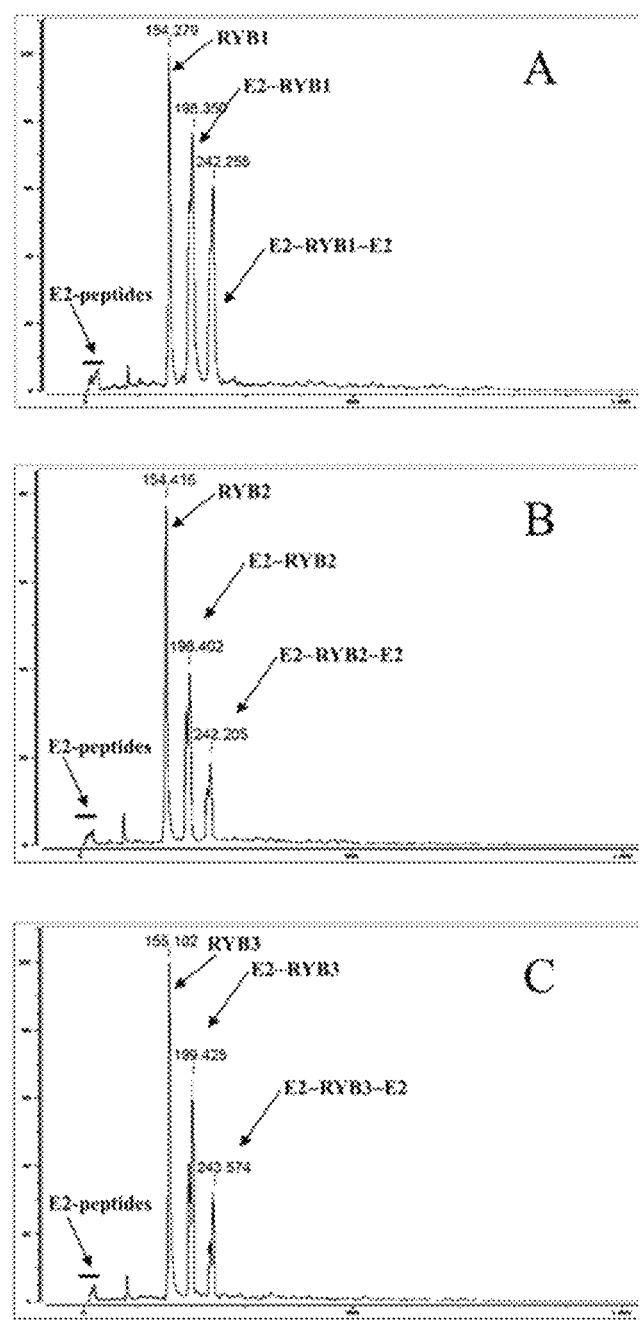

FIG. 9 shows the mass spectra of complexes of recombinant E2 protein with antibodies RYB1, RYB2 and RYB3 in the presence of an excess of E2 protein proteolysis peptide products.

The following examples are to illustrate the essence and industrial applicability of the claims of this invention.

EXAMPLE 1

Producing Hybrid Cell Clones (Hybridomas)

In order to create hybridoma cells producing natural fully human monoclonal antibodies against proteins of the hepatitis C viral envelope, clinical materials from seven patients who died from hepatitis C were used. In all these patients, the initial diagnosis was made based on the presence of antibodies against HCV antigens. The antibodies were detected by the commercially available enzyme-linked immunosorbent assay (ELISA) method. No exclusion criteria related to age, race or stage of the disease at the time of death were applied. Concomitant infections such as HIV, herpes simplex, human papilloma virus and sexually transmitted diseases were allowed. A history of drug addiction as well as the presence of a malignant neoplasm of the liver and other diseases were also allowed. The only exclusion criteria were septic shock and any autoimmune disease, including lupus, diabetes, etc. All data which could identify the patient who died were removed; and the clinical information only included information regarding age, gender and disease history.

The spleen was removed and placed in a 100 mm Petri dish with sterile medium RPMI 1640, supplemented with 4 mM L-glutamine, nonessential amino acids (from a 100-fold concentrate), vitamins (from a 100-fold concentrate), 1 mM sodium pyruvate and 50 µg/ml gentamicin. Pieces of spleen were disrupted using forceps and scissors. The disrupted tissue was passed through a metal sieve (50 mesh cells) using glass pestle. 10 ml of the resulting suspension was transferred to sterile conical 15 ml test tubes, containing 5 ml of Histopaque 1077 lymphocyte separation medium (Sigma-Aldrich, USA) and centrifuged for 20 min at 400 g. An opaque ring of mononuclear cells, which is formed on the border between layers, was collected using a Pasteur pipette and diluted to 10 times with the standard serum-free medium RPMI 1640. The cells were centrifuged at 300 g for 10 minutes and washed twice with the medium.

BIONA-X cells, which are a specialized hybrid (mouse/human) myeloma cell line created by BionA Pharma Ltd. for the production of human hybridomas, were grown in an RPMI 1640 medium without antibiotics and supplemented with 10% fetal bovine serum (Hyclone), 4 mM L-glutamine, 1 mM sodium pyruvate, nonessential amino acids and vitamins (complete medium). Prior to fusion the cells were cultured in the presence of 20 µg/ml of 8-azaguanine (Sigma-Aldrich, USA) to prevent HAT-sensitive cells from reverting to wild type cells. Cells in an exponential growth phase were adjusted to a density of 10% of a monolayer.

Cells from the BIONA-X line and mononuclear spleen cells were washed three times in the serum-free medium RPMI 1640 by centrifugation for 5 min at 300 g, these were mixed together in a ratio of 1:5 (BIONA-X: spleen cells) and centrifuged for 10 minutes at 300 g. The supernatant was removed, the cell pellet was resuspended in 100-300 µl (depending on cell volume) of DMEM medium, 100-300 µl of a solution of polyethyleneglycol-1500/dimethyl sulfoxide (1:1) warmed to room temperature was added to the cell mixture and then the test tube was shaken for 3 minutes with light tapping. Subsequently, 15 ml of a mixture (1:1) of Hanks balanced salt solution and phosphate buffered saline (PBS) was added to the test tube as following: 10 ml slowly over 10 minutes, and then 5 ml over 5 minutes. After which, 10 ml complete medium was added over 5 minutes and, finally, another 5 ml complete medium was added over 1 minute. The total volume was 30 ml. Then 600 µl of a 50-fold concentrate of a HT (hypoxanthine-thymidine) solution (Cellgro, USA) and 20-30 µl dimethyl sulfoxide were added to the test tube. The cell suspension was stirred in the test tube, transferred to a Petri dish (100×15 mm) and incubated at 37° C. in a $CO_2$ incubator overnight. Thereafter, the cells were collected, centrifuged at 300 g for 10 minutes and resuspended in a complete medium to which a HAT (hypoxanthine-aminopterin-thymidine) solution of a 50-fold concentrate (Cellgro, USA) was added.

After fusion, the cells were seeded into 96-well plates in a 200 µl volume (approximately 250,000 cells per well) in RPMI 1640 growth medium without antibiotics, supplemented with 10% fetal bovine serum (Hyclone), 4 mM L-glutamine, 1 mM sodium pyruvate, nonessential amino acids and vitamins. A total of 65 plates were inoculated. Twice a week 50% of the medium was removed and replaced with fresh medium. In the first week the cell clones were cultured with the addition to the growth medium of a HAT solution, and the subsequent two weeks with the addition of a HT solution, after which, screening was carried out for the secretion of human immunoglobulins.

The hybridoma clones were tested for the secretion of human IgG immunoglobulins as following. ELISA plates were coated with polyclonal goat anti-human IgG immunoglobulins specific for Fc-fragments (Sigma-Aldrich, USA). To this end, antibodies were added to the wells of the plates in a 100 µl carbonate buffer (0.1 M sodium carbonate, pH 9.0) at 100 ng per well. The plates were covered by sealed caps and incubated overnight at 4° C. The plates were then washed twice with a PBS solution, the remaining droplets were removed, 200 µl of a blocking solution (0.4% dry non-fat milk in PBS) was added to the wells and plates were incubated for 2 hours. The wells were washed 3 times with PBS, and then 50 µl hybridoma supernatant diluted with the blocking solution in a ratio of 1:1 was added to each well.

The complete cell culture medium served as a negative control. Human serum at a dilution of 1:2000 served as a positive control.

The plates were incubated for 2 hours at room temperature, washed 4 times with PBS and horseradish peroxidase labelled goat polyclonal antibodies against human IgG immunoglobulins (Sigma-Aldrich, USA) diluted in a blocking solution in a ratio of 1:2000 were added to the wells. After 1 hour incubation at room temperature the plates were washed 4 times with PBS and a peroxidase substrate (ortho-phenylenediamine in a phosphate-citrate buffer with hydrogen peroxide) was added to each well. The color reaction was stopped by adding 20 µl of 10% hydrochloric acid. Colorimetric measurements were carried out in an Infinite F50 (Tecan, Austria) plate reader at 492 nm.

A positive test result was considered to be an optical density value of at least 3 times the optical density level in the negative control wells. 100% of 6240 primary hybridoma clones showed a positive result and, therefore, secreted IgG human immunoglobulins into the culture medium.

EXAMPLE 2

Production of HEK293 Cells, Stably Transfected by HCV E1-E2 Genes

The nucleotide sequence encoding the polyprotein of hepatitis C virus isolate H77 (genotype 1a) was obtained from the international database NCBI Nucleotide. The sequence has reference number NC_004102.1. To obtain the genetic structure encoding the genes of E1-E2 of HCV, a fragment of this sequence (nucleotides 735-2579, SEQ ID NO: 1) was used which encodes amino acids 132-746 of the polyprotein. The sequence GCAGGTACCGCCGCCGC-CATGAATTCC (SEQ ID NO: 2) was attached to the 5'-end of the fragment, contains a restriction enzyme Acc651 recognition site, a ribosome binding region and codes for amino acids Met, Asn and Ser. TAATCTAGAGCG (SEQ ID NO: 3) was attached to the 3'-end of the fragment, encodes the translation termination signal, and comprises a recognition region of restriction enzyme XbaI recognition site. As a result, a nucleotide sequence was produced which comprises a ribosome binding site and codes for amino acids Met, Asn, Ser, a fragment from 60 C-terminal amino acids of Core protein (amino acids 132-191 of the HCV polyprotein), the E1 protein (amino acids 192-383 of the polyprotein) and the E2 protein (amino acids 384-746 of the polyprotein). A double-stranded DNA fragment with the stated nucleotide sequence (SEQ ID NO: 4) was chemically synthesized, split by restriction enzyme Acc651 and XbaI and inserted into the eukaryotic expression vector pcDNA3.1-neo (Invitrogen, USA) at the sites of restriction enzymes to form the plasmid pcDNA3.1-E1E2.

In people infected by hepatitis C virus, the proteins Core, E1, and E2 are formed from the HCV polyprotein as a result of cellular signal peptidases splitting and are translocated to the endoplasmic reticulum. The correct folding of the E1 and E2 proteins and formation of a complex between them largely depends on the joint translocation and processing thereof (Cocquerel L, Meunier J C, Op de Beeck A, Bonte D, Wychowski C, Dubuisson J. J. Gen. Virology. 2001, 82(7): 1629-1635). Therefore, it can be assumed that polyprotein fragment encoded by plasmid pcDNA3.1-E1E2, containing the C-terminal part of Core, E1, and E2, would be split in plasmid-transfected cells in a similar manner. Thus, the E1 and E2 proteins can form heteromeric complexes with each other similar in structure to HCV envelope protein complexes. The transmembrane domains of the E1 and E2 proteins maintain complexes in the endoplasmic reticulum (Flint, M., and J. A. McKeating J. Gen. Virol 1999, 80 (8): 1943-1947), resulting in the need for cell permeabilization prior to fluorometric immunoassay.

Human embryonic kidney cells, HEK293, were cultured in a DMEM medium supplemented with 10% fetal bovine serum (Invitrogen, USA), 2.2 mM L-glutamine, 100 IU/ml penicillin and 100 mg/ml streptomycin, at 37° C. in a $CO_2$ incubator with 5% $CO_2$. For transfection, cells were seeded to a 24-well plate wells (50,000 cells per well). Next day, cells were transfected by pcDNA3.1-E1E2 plasmid using Lipofectamine 2000 reagent (Invitrogen, USA) at a ratio 1 μg of plasmid DNA and 1 μg of reagent per well according to the manufacturer's protocol. After 24 hours the culture medium was changed for a fresh medium and the cells were incubated for another 24 hours. Thereafter, the cells were removed from the substrate with trypsin, serial dilutions of the cell suspension were prepared and seeded to 96-well plates. Antibiotic G418 (Invitrogen, USA) was added to the culture medium to a final concentration of 1 mg/ml for a selection of transfected clones. After 2-3 weeks, the cells from the wells containing no more than one cell clone were transferred into wells of a 24-well plate, expanded, transferred into cell culture flasks and then frozen.

Cells of transfected clones were tested for expression of E1-E2 protein complexes. For this, the cells were grown in T75 flasks (Corning-Costar, USA) to the condition of a fresh monolayer (5-6 million cells). Flasks with cells were rinsed with 5 ml cold PBS, 5 ml of a cold solution of 20 mM EDTA prepared in PBS were added, and the flasks were incubated on ice for 20 minutes. Then the flasks were shaken to make sure that all cells had detached, 5 mL of PBS were added and the cell pellet was collected by centrifugation for 15 min at 200 g.

For the permeabilization of the cells, the pellet was washed twice in 10 ml PBS and resuspended in 1 ml of pre-cooled to −20° C. methanol. Another 9 mL of cold methanol was added to the suspension and cells were incubated at −20° C. for 20 minutes, with occasional vortexing. After incubation, the cells were pelleted by centrifugation at 400 g, washed with PBS, resuspended in 10 ml PBS and placed into Eppendorf tubes for testing conditioned media of hybridoma clones, $10^5$ cells per tube.

1.5 ml solution of 0.3% bovine serum albumin (BSA) in PBS was added to a suspension of permeabilized cells, incubated for 5 min, the cells were pelleted by centrifugation and resuspended in a 20 μl solution of 20 μg/ml of mouse monoclonal antibodies BD1167 against the HCV antigen E2 (Abcam, USA) prepared in PBS with 0.3% BSA. The cells were incubated for 30 min at room temperature, then washed in a 1.5 ml of a 0.3% BSA solution in PBS, incubated for 30 min at room temperature with 20 μl FITC-labelled affinity purified rabbit antibodies against mouse immunoglobulins (Becton Dickinson, USA) at a concentration of 2 μg/ml, and washed in a 1.5 ml of a 0.3% BSA solution in PBS and suspended in 400 μl of 1% formaldehyde in PBS. The fluorescence of cells was analyzed on a FACS-Calibur flow cytometer (BD Biosciences, USA). A cell clone which has shown the highest expression of the E1-E2 complex was selected for further use and was named HEK-E1E2.

EXAMPLE 3

Selection of Hybridoma Clones Producing Human Monoclonal Antibodies to HCV Envelope Proteins To select hybridomas producing human antibodies capable of recognizing E1-E2 protein complex, HEK-E1E2 cells were used, the production of which is described in Example 2. The non-transfected cells of a HEK293 parental cell line served as control. Cells were grown and permeabilized as described in Example 2.

Hybridoma conditioned media were tested as following. 1.5 ml of 0.3% BSA in PBS was added to a suspension of permeabilized HEK-E1E2 or HEK293 cells, incubated for 5 min, and the cells were pelleted by centrifugation and resuspended in a 20 µl sample of a conditioned medium. The cells were incubated for 30 min at room temperature, then washed in 1.5 ml of a 0.3% BSA solution in PBS, incubated for 30 min at room temperature with 20 µl of FITC-labelled affinity purified rabbit antibodies to human immunoglobulins (Company IMTEK, Moscow) at a concentration of 3.3 µg/ml, washed in 1.5 ml of a 0.3% BSA solution in PBS and resuspended in 400 µl of 1% formaldehyde in PBS. The fluorescence of cells was analyzed using FACS-Calibur flow cytometer (BD Biosciences, USA). The result was considered positive if the average fluorescence value of HEK-E1E2 cells was at least 3 times higher than the average fluorescence value of the HEK293 control cells incubated with the same sample of conditioned medium.

Figure 1:
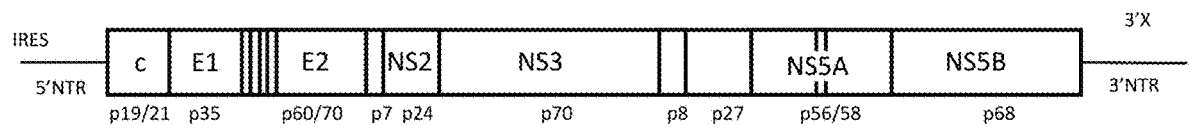
Figure 2:
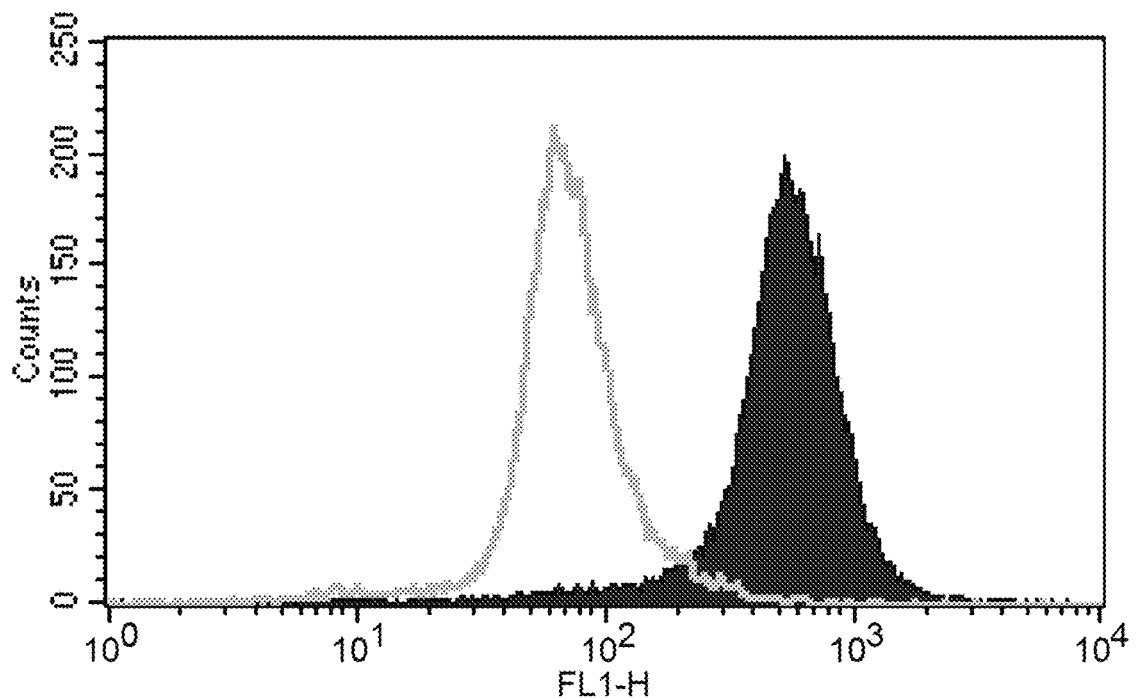
FIG. 2 shows the results of cytofluorimetric analysis of HEK-E1E2 cells (dark histogram) after incubation with a conditioned medium from one of the hybridoma clones. The grey curve is a histogram of immunofluorescence of control untransfected HEK293 cells after incubation with the same conditioned medium.

FIG. 2 shows a typical result of flow cytometric analysis, which reveals the presence in the conditioned medium of human antibodies recognizing the E1-E2 protein complex in transfected cells. Of 6240 hybridoma clones analyzed, 56 showed a positive result in the test for binding to HEK-E1E2 cells and were selected for recloning. After several rounds of cloning, most cell lines lost the ability to secrete antibodies that recognize the E1-E2 complex. Ultimately three hybridoma cell lines were obtained which stably produce human antibodies against the E1-E2 protein complex. These lines of hybridomas were designated as BIONA-RYB1, BIONA-RYB2 and BIONA-RYB3, and the antibodies they produce were called, respectively, RYB1, RYB2 and RYB3. The hybridoma cell lines BIONA-RYB1, BIONA-RYB2 and BIONA-RYB3 were deposited on 17 Jul. 2013 in the Russian National Collection of Industrial Microorganisms under the Identifiers H-142, H-143 and H-144.

EXAMPLE 4

Production of a Purified Preparation of Human Monoclonal Antibodies RYB1

Hybridoma cell line BIONA-RYB1 were cultured in 8 hollow-fiber bioreactor cartridges of the FiberCell Duet Pump type (FiberCell Systems Inc., USA) in serum-free medium HyClone SFM4MAb (HyClone, USA). For the initial load, $5.10^8$ cells per cartridge were used. The first collection of conditioned medium containing monoclonal antibodies was done 4 weeks after the initiation of cell culture. The volume collected was 50 ml from one cartridge, wherein the antibody concentration in the medium ranged from 0.01 mg/ml to 0.05 mg/ml. The conditioned medium was collected every 6 days over 3 months, so that the total volume of the collected medium was 6.0 liters. The batches of medium were frozen and stored at −20° C.

In order to chromatographically purify the antibodies, the conditioned medium was thawed and concentrated by an Amicon Filtering System using a 100 kDa MWCO membrane (Millipore, USA). Prior to concentration, the System and membrane were washed with sterile pyrogen-free water to eliminate endotoxins. 800 ml of concentrate containing 90 mg human antibodies was obtained from the 6 liters of medium. The concentrate was diluted with an equal volume of binding buffer and loaded onto a column with 2 mL of protein A/G plus agarose resin (Pierce, USA) for 3 hours. The column was washed with 20 ml binding buffer, the antibodies were eluted with 10 ml of elution buffer and 0.5 ml fractions were collected into test tubes with a neutralizing buffer (100 µl 1 M Tris-HCl, pH 8.0). Fractions containing proteins were combined and dialyzed against PBS.

Figure 3:
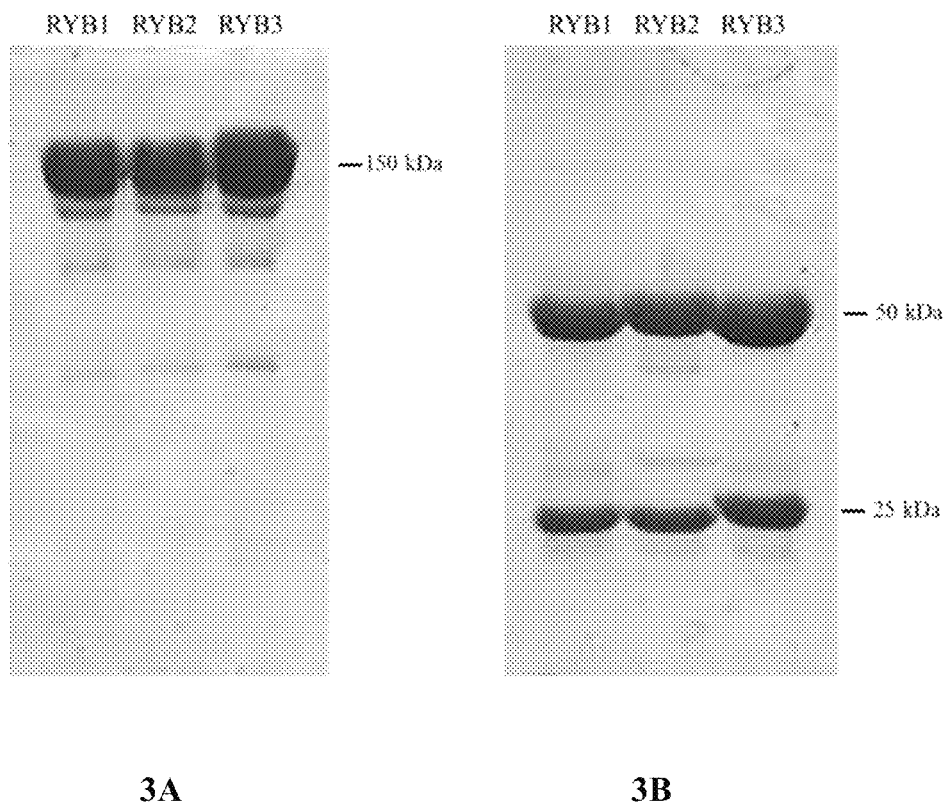
FIG. 3 shows an electrophoregram of samples of purified antibodies RYB1, RYB2 and RYB3 (7.5 μg per lane) separated in 7.5% polyacrylamide gel without mercaptoethanol (3A) or in a 10% polyacrylamide gel with mercaptoethanol (3B) in the presence of sodium dodecyl sulphate and stained with Coomassie Brilliant Blue R-250.

The preparation of purified RYB1 antibodies (76 mg) was analyzed using electrophoresis in polyacrylamide gel in the presence of sodium dodecyl sulphate. Analysis showed (FIG. 3) that there were virtually no foreign protein contaminants in the obtained preparation.

EXAMPLE 5

Production of a Purified Preparation of Human Monoclonal Antibodies RYB2

RYB2 monoclonal antibodies were prepared according to the technique in example 4 using hybridoma BIONA-RYB2. The total volume of the collected medium for hybridoma BIONA-RYB2 was 5.8 l, the yield of purified antibodies RYB2 was 81 mg. Analysis showed (FIG. 3) that virtually no foreign protein contaminants in the obtained preparation.

EXAMPLE 6

Preparation of a Purified Preparation of Human Monoclonal Antibodies RYB3

RYB3 monoclonal antibodies were prepared according to the technique in example 4 using hybridoma BIONA-RYB3. The total volume of the collected medium for hybridoma BIONA-RYB3 was 6.1 l, the yield of purified antibodies RYB3 was 85 mg. Analysis showed (FIG. 3) that virtually no foreign protein contaminants in the obtained preparation.

EXAMPLE 7

Determination of Subclasses of the Heavy and Light Chains of Antibodies

The subclasses of heavy chains of antibodies RYB1, RYB2 and RYB3 were determined using the kit Human IgG Subclass Profile Kit (Invitrogen, USA). Mouse monoclonal antibodies against human immunoglobulins of subclasses IgG1, IgG2, IgG3 and IgG4 were added to the wells of an immunological plate according to the manufacturer's instructions, then diluted preparations of purified antibodies RYB1, RYB2 and RYB3 were added, and incubated for 30 min. Following this, the plate wells were washed, peroxidase-labelled anti-human IgG immunoglobulins were applied, incubated for 30 min, the plates were washed again and developed using a TMB substrate. Optical density values at 450 nm were read using plate reader Infinite F50 (Tecan, Austria) after the reaction was stopped. This analysis revealed that heavy chains of all three antibodies belong to the subclass IgG1.

Light chain types were determined using the Human IgG Subclass Profile Kit, but goat polyclonal antibodies against kappa-type light chains or against Lambda-type light chains of human immunoglobulins were used as peroxidase labelled antibodies (Bethyl Laboratories, USA). The light chains of antibodies RYB1, RYB2 and RYB3 were determined as kappa type.

EXAMPLE 8

Determination of the Amino Acid Sequences of Variable Regions of Heavy and Light Chains of Antibodies RYB1, RYB2 and RYB3

In order to determine the amino acid sequences of variable regions of antibodies from hybridoma cells BIONA-RYB1, BIONA-RYB2 and BIONA-RYB3, total cellular RNA was isolated, the cDNA was generated using reverse transcriptase and cDNA fragments encoding variable domains of human immunoglobulins, were amplified. The amplified fragments were cloned, underwent sequencing and, on the basis of nucleotide sequences obtained by translation in silico, the amino acid sequences of corresponding regions of antibodies RYB1, RYB2 and RYB3 were determined. Detailed description and the results are presented below.

$5.10^7$ cells of each hybridoma were collected in the exponential growth phase. The cells were washed with PBS and lysed in 10 ml of RLT-buffer from the RNA isolation kit RNeasy Midi Kit (Qiagen, USA). To reduce the viscosity of the solution, lysates were pressed once through a 29G gauge needle, an equal volume (10 ml) of 70% ethanol was added and applied to chromatographic columns of the RNA isolation kit. The columns were washed with solutions RW1 and RPE from the kit, after which the RNA was eluted in 4 ml $H_2O$. 100 μl of 5 M NaCl and 10.5 ml of ethanol were added to the eluates and incubated overnight at −20° C. to precipitate RNA. The RNA precipitates were collected by centrifugation 30 min at 4000 rev/min, dissolved in 900 μl $H_2O$, 100 μl 10-fold buffer for DNAase (400 mM Tris-HCl, pH 7.0, 100 mM NaCl, 100 mM $MgCl_2$), 5 μl recombinant DNAase I, 10 u/μl, free from impurities of ribonucleases (Roche Applied Science, USA) were added and incubated for 2 hours at room temperature to cleave the residual cellular DNA. The reaction was stopped by adding 40 μl 0.5 M EDTA, 4 ml RLT buffer and 2.8 ml ethanol were added and applied to a column from the RNA isolation kit to carry out a second round of purification as described above. The eluted RNA, free from impurities of genomic DNA, was precipitated with ethanol, collected by centrifugation, dissolved in $H_2O$ and the concentration was adjusted to 1 mg/ml. RNA concentration was measured spectrophotometrically at a 260 nm wavelength. The absence of RNA degradation was monitored by electrophoresis in formaldehyde-agarose gel in the presence of ethidium bromide. The ratio of the intensities of the 28s and 18s ribosomal RNA bands was approximately 2:1.

The reverse transcription reaction for RNA from BIONA-RYB1, BIONA-RYB2 and BIONA-RYB3 cells took place in a volume of 10 μl using 2 μg total cellular RNA, oligo(dT)-primer and the reverse transcriptase PowerScript (Clontech, USA) for 2 hours at 42° C. according to the manufacturer's protocol. Aliquots of the obtained cDNA were amplified in the presence of primer sets specific to the 5' and 3' ends of the nucleotide sequences encoding the variable regions of heavy ($V_H$) and light ($V_L$) chains of IgG1 kappa human immunoglobulins (Antibody Engineering: Methods and Protocols, edited by Benny K. C. Lo 2004, Humana Press Inc., p. 282). The amplification products were cloned in vector pCR2.1 (Invitrogen, USA) and the resulting clones (at least 4 clones for each variable region of immunoglobulin) were sequenced. Sequencing results revealed the nucleotide and amino acid sequences of the variable regions of the $V_H$ and $V_L$ of the antibodies RYB1, RYB2 and RYB3. Regions which determine complementarity (Complementarity Determining Region, CDR) in the $V_H$ and $V_L$ sequences were identified in accordance with the numbering system IMGT (Lefranc M P, Giudicelli V, Ginestoux C, Bodmer J, Muller W, Bontrop R, Lemaitre M, Malik A, Barbie V, Chaume D. Nucleic Acids Res.1999, 27 (1): 209-212).

Thus the following amino acid sequences, which were shown in the sequence list, were determined:

the sequence of the $V_H$ region of the antibody RYB1, SEQ ID NO: 5;

the CDR1 sequence of the $V_H$ region of the antibody RYB1, SEQ ID NO: 6;

the CDR2 sequence of the $V_H$ region of the antibody RYB1, SEQ ID NO: 7;

the CDR3 sequence of the $V_H$ region of the antibody RYB1, SEQ ID NO: 8; the $V_L$ region sequence of the antibody RYB1, SEQ ID NO: 9;

the CDR1 sequence of the $V_L$ region of the antibody RYB1, SEQ ID NO: 10; the CDR2 sequence of the $V_L$ region of the antibody RYB1, SEQ ID NO: 11; the CDR3 sequence of the $V_L$ region of the antibody RYB1, SEQ ID NO: 12; the $V_H$ region sequence of the antibody RYB2, SEQ ID NO: 13;

the CDR1 sequence of the $V_H$ region of the antibody RYB2, SEQ ID NO: 14; the CDR2 sequence of the $V_H$ region of the antibody RYB2, SEQ ID NO: 15; the CDR3 sequence of the $V_H$ region of the antibody RYB2, SEQ ID NO: 16; the $V_L$ region sequence of the antibody RYB2, SEQ ID NO: 17;

the CDR1 sequence of the $V_L$ region of the antibody RYB2, SEQ ID NO: 18; the CDR2 sequence of the $V_L$ region of the antibody RYB2, SEQ ID NO: 19; the CDR3 sequence of the $V_L$ region of the antibody RYB2, SEQ ID NO: 20; the $V_H$ region sequence of the antibody RYB3, SEQ ID NO: 21;

the CDR1 sequence of the $V_H$ region of the antibody RYB3, SEQ ID NO: 22; the CDR2 sequence of the $V_H$ region of the antibody RYB3, SEQ ID NO: 23; the CDR3 sequence of the $V_H$ region of the antibody RYB3, SEQ ID NO: 24; the $V_L$ region sequence of the antibody RYB3, SEQ ID NO: 25;

the CDR1 sequence of the $V_L$ region of the antibody RYB3, SEQ ID NO: 26; the CDR2 sequence of the $V_L$ region of the antibody RYB3, SEQ ID NO: 27; and the CDR3 sequence of the $V_L$ region of the antibody RYB3, SEQ ID NO: 28.

EXAMPLE 9

Competition Study of the Antibodies

For the study of competition between the antibodies, RYB1, RYB2 and RYB3 were labelled with fluorescein isothiocyanate (FITC) using FluoroTag FITC Conjugation Kit (Sigma-Aldrich, USA) according to the manufacturer's instructions. In preliminary flow cytometric analysis of the binding of FITC-labelled antibodies at various concentrations to permeabilized HEK-E1E2 cells, the association constants $K_a$ and antibody concentrations at which the binding reaction reaches saturation were determined. To this end, the relationship between the mean fluorescence values of cells incubated with labelled antibodies and antibody concentration was measured. Table 1 shows the association constants and antibody concentrations sufficient to saturate specific binding centers which are the HCV E1-E2 protein complexes, after 2-hours incubation.

TABLE 1

The association constants and antibody concentrations
sufficient to saturate specific binding centers,
in HEK-E1E2 cells after 2-hours of incubation.

| Antibody | Ka (M$^{-1}$·c$^{-1}$) | Saturating concentration (μg/ml) |
|---|---|---|
| RYB1 | 8300 | 5.0 |
| RYB2 | 10000 | 4.2 |
| RYB3 | 20000 | 2.1 |

In the experiment studying antibody competition, mixtures of FITC-labelled and unlabeled antibodies were established in ratios of 1:0 (only a labelled antibody), 1:5 and 1:20 in all possible combinations. According to preliminary experiment data, the concentration of labelled antibodies in the mixtures was selected to be equal to 5 μg/ml for RYB1 and RYB2 and 2 μg/ml for RYB3. The fully human monoclonal antibody Adalimumab (brand name Humira), which is specific for tumor necrosis factor alpha and which belongs to the subclass IgG1, was used as the negative control. 1.5 ml of a 0.3 BSA solution in PBS was added to suspended samples of permeabilized HEK-E1E2 cells, incubated 5 min, cells were pelleted by centrifugation and resuspended in 20 μl of a mixture of labelled and unlabeled antibodies. Cells were incubated for 2 hours at room temperature, then washed in a 1.5 ml of a 0.3% BSA solution in PBS and suspended in 400 μl of 1% formaldehyde in PBS. Cell fluorescence was analyzed on a FACS-Calibur flow cytometer (BD Biosciences, USA) and the average fluorescence values were determined for each sample. The level of fluorescence due to the nonspecific binding of labelled antibodies to cells was determined in a similar manner by using untransfected HEK293 cells instead of HEK-E1E2.

The experimental results are shown in FIG. 4. They show that antibodies RYB1, RYB2 and RYB3 effectively compete with each other for binding to the E1-E2 protein complex. The degrees of antibody competition in heterologous pairs are virtually indistinguishable from competition in homologous pairs. Thus, the human antibody Adalimumab does not compete with any of the antibodies studied.

It appears that the epitopes of these antibodies overlap each other or are located close to one other in the spatial structure of the protein E2, such that binding an antibody to one of the epitopes prevents the interaction of another epitope with its antibody, indicating the correct use of the proposed set of epitopes for affecting the hepatitis C virus using the obtained antibodies.

EXAMPLE 10

Formation of Complexes of Antibodies with Recombinant Protein E2

The amino acid sequence (SEQ ID NO: 29), which corresponds to the sequence of the E2 protein of the hepatitis C virus of isolate H77 (genotype 1a), was obtained from the international database NCBI Protein. The sequence has a reference number NP_751921.1 and contains 363 amino acid residues with coordinates 384-746 of the HCV polyprotein sequence of the same isolate (reference number NP_671491.1). The E2 protein amino acid sequence was subject to reverse translation in silico to produce the nucleotide sequence which encodes the E2 protein and which is codon optimized for expression in the bacteria *E. coli*. On the basis of this sequence, the E2 protein gene was constructed by chemical synthesis and inserted into the prokaryotic expression vector pET100/D-TOPO (Invitrogen, USA) to produce the plasmid pET100-E2. During insertion, the regions which code Xpress-epitope and 6×His-tag were removed from the vector.

The plasmid PET100-E2 transformed *E. coli* cells of the strain BL21 (DE3), clones of bacterial transformants were grown at 37° C. in the shaker incubator Innova 43R (New Brunswick Scientific, USA) in glass flasks of 2 l to an optical density of OD$_{600}$=0.5, the recombinant product expression was induced by adding IPTG up to 1 mM and then bacteria were grown for another 150 minutes. The recombinant protein E2 was removed from the bacteria lysate using standard chromatographic procedures.

Attempts to demonstrate the binding of antibodies RYB1, RYB2, and RYB3 to recombinant E2 protein by the traditional method of Western-analysis in which electrophoresis is carried out in a polyacrylamide gel in the presence of sodium dodecyl sulphate (SDS) did not yield positive results. Apparently a change in the conformation of the E2 protein under the effect of SDS violates the structure of epitopes recognized by the antibodies. Therefore, an alternative approach to monitoring complexes was used which is based on mass spectrometry.

For the formation of complexes with antibodies, 5 μl purified E2 protein solution with a concentration of 4 μM in PBS was mixed with 5 μl of a solution of one of the antibodies RYB1, RYB2 and RYB3 with a concentration of 2 μM. 1 μl of stabilizing reagent K200 from K200 MALDI MS analysis kit (CovalX, Switzerland) was added to 9 μl of the produced mixture and incubated for 3 hours at room temperature. Processing using a stabilizing reagent causes covalent crosslinking of the complex components (Bich C, Maedler S, Chiesa K, DeGiacomo F, Bogliotti N, Zenobi Anal Chem 2010 82 (1): 172-179). Thus the molecular mass of the complex increased by about 4-5% due to the addition of stabilizing agent molecules.

The samples for mass spectrometric analysis by matrix-assisted laser desorption/ionization (MALDI) were prepared in the following manner. After incubation, 1 μl matrix, which consists of recrystallized sinapic acid (10 mg/ml) in an acetonitrile-water solution (1:1, v/v) additionally containing 0.1% trifluoroacetic acid, was added to 1 μl of a mixture comprising crosslinked complexes. 1 μl of the resulting mixture was applied to the MALDI-plate MTP AnchorChip 384 TF (Bruker Daltonik, Germany), where the sample was crystallized at room temperature.

Immediately after crystallization, the plate with samples is placed in a receiver device of the time-of-flight mass analyzer Ultraflex III MALDI TOF TOF (Bruker Daltonik, Germany) equipped with the detector HM3 High-Mass system (CovalX, Switzerland), which makes it possible to register microaggregates with a molecular mass of up to 2 MDa with sensitivity in the nanomolar range. Mass spectrometric analysis was performed using a standard nitrogen laser in a linear positive range at the following configurable parameters: Ion Source 1:20 kV, Ion Source 2:17 kV, Lens: 12 kV, Pulse Ion Extraction: 400 ns, HM3 Gain Voltage: 3.14 kV, HM3 Acceleration Voltage: 20 kV. The spectra were averaged over 300 events of laser detection. Clusters of insulin, bovine serum albumin and immunoglobulin G were used to calibrate the instrument. The data were processed using the program Complex Tracker analysis, version 2.0 (CovalX, Switzerland). All measurements were repeated three times.

Analysis of pure E2 protein, as well as preparations of antibodies taken separately, showed (FIG. 5, A-D) that neither the E2 protein nor antibodies form complexes or aggregates by themselves. It should be noted that due to treatment using a stabilizing reagent, the observed molecular weight of the recombinant E2 protein, which according to calculations is 40048 Da, grows on average to 44215 Da. An additional peak with a molecular weight of about 60 kDa, which is present in the spectra of antibody samples, corresponds, most likely, to an associated protein. After mixing the E2 protein with preparations of antibodies, peaks appear in the spectrum of the samples (FIG. 5 E-G), which correspond in weight to molecular complexes comprising one antibody molecule and one or two molecules of the E2 protein (Table. 2). The stoichiometric structure of the complexes fully corresponds to the bivalent nature of monoclonal IgG antibodies. Thus, the ability of RYB1, RYB2 and RYB3 antibodies to form complexes with recombinant E2 protein in a solution is confirmed.

TABLE 2

The molecular weights of complexes of the E2 protein with antibodies RYB1, RYB2 and RYB3.

| Sample composition | Observed molecular weight | Molecular structure |
| --- | --- | --- |
| E2 | 44,215 Da | E2 |
| RYB1 | 154,158 Da | RYB1 |
| RYB2 | 154,258 Da | RYB2 |
| RYB3 | 155,145 Da | RYB3 |
| E2 + RYB1 (2:1) | 44,187 Da | E2 |
| | 154,215 Da | RYB1 |
| | 198,214 Da | E2-RYB1 |
| | 242,102 Da | E2-RYB1-E2 |
| E2 + RYB2 (2:1) | 44,213 Da | E2 |
| | 154,345 Da | RYB2 |
| | 198,321 Da | E2-RYB2 |
| | 242,127 Da | E2-RYB2-E2 |
| E2 + RYB3 (2:1) | 44,225 Da | E2 |
| | 155,084 Da | RYB3 |
| | 199,402 Da | E2-RYB3 |
| | 243,547 Da | E2-RYB3-E2 |

EXAMPLE 11

Determination of Antibody Epitopes

In order to determine the epitope specificity of the RYB1, RYB2 and RYB3 antibodies with a high resolution, antigen-antibody complexes were treated with a crosslinking reagent labelled with deuterium, and were then subjected to multi-enzyme proteolysis. The obtained peptides were analyzed and identified using nano-liquid chromatography followed by mass spectrometry. The epitopes were determined by the disappearance of a series of tagged peptides from the spectrum of antigen proteolysis products in the case of the formation of a complex with an antibody. Below is a detailed description of each of the steps of the procedure.

In the first step antigen-antibody complexes were formed in a stoichiometric ratio of 2:1 under the following conditions: 5 µl of recombinant E2 protein solution (see example 10) with a concentration of 4 µM were mixed with 5 µl of a solution of one of the antibodies RYB1, RYB2 or RYB3 with concentration of 2 µM and incubated for 180 minutes at 37° C. 10 µl of a solution of E2 protein with a concentration of 2 µM was used as a pure antigen sample. The pure antigen sample was also incubated for 180 minutes at 37° C.

In the second step 1 µl of a pre-prepared mixture (1:1) of the crosslinking reagents disuccinimidyl suberate DSS-d0 and disuccinimidyl suberate DSS-d12 labelled with 12 deuterium atoms (CovalX, Switzerland) with a total concentration 2 mg/ml in dimethylformamide were added to the antigen-antibody complex samples and pure antigen sample. The samples were incubated for 180 min at room temperature in order to form crosslinks.

In the third step disulphide bonds are reduced and alkylation is carried out on the samples to facilitate subsequent proteolysis. 20 µl 25 mM ammonium bicarbonate, pH 8.3, and 2.5 µl 500 mM dithiothreitol were added to samples after the crosslinking reaction, incubated for 60 min at 55° C., after which 2.5 µl 1M iodoacetamide was added and incubated for another 60 minutes at room temperature in a place without light.

In the fourth step the samples were subjected to proteolysis using trypsin or α-chymotrypsin. For the treatment with trypsin, 120 µl proteolysis buffer (100 mM Tris-HCl, pH 7.8, 10 mM $CaCl_2$) and a 2 µl trypsin solution (1 mg/ml) were added to the samples and incubated overnight at 37° C. For the treatment with α-chymotrypsin, 120 µl of the same proteolysis buffer and a 2 µl α-chymotrypsin solution (200 µM) were added to the samples and incubated overnight at 30° C.

In the fifth step the proteolysis products were separated on the nano-liquid chromatograph Ultimate 3000 (Dionex, Germany) with the aid of a preliminary column 300-µm ID×5-mm C4 PepMap and main column 75-µm ID×5-cm C4 PepMap in a gradient (95% $H_2O$, 5% acetonitrile, 0.1% HCOOH)-(20% $H_2O$, 80% acetonitrile, 0.1% HCOOH).

In the sixth step the material of the chromatographic peaks undergoes mass spectrometric analysis on the instrument LTQ Orbitrap XL (Thermo Scientific, USA) connected by hardware to a chromatographic system. Since the crosslinking reagent used for processing complexes is a mixture of deuterium-labelled and unlabeled molecules in a 1:1 ratio, each peptide, which carries one molecule of crosslinking reagent, is shown in the mass spectrum by two signals of the same intensity, differing from each other by exactly 12 atomic units—the number of deuterium atoms in the molecule DSS-d12 (in the case of singly ionized peptides). This fact makes it possible to produce a primary set of signals corresponding to the peptides with a single molecule of the crosslinking reagent. These peptides were further identified with the determination of their amino acid sequence on the basis of data from mass spectrometry using the software XQuest, version 2.0, and databases CovalX_110823_01.fasta of the company CovalX (Switzerland), using an amino acid sequence of recombinant protein E2 (SEQ ID NO: 29). In addition, for each peptide the position of the amino acid covalently linked to the crosslinking reagent molecule was also established.

The seventh step involves a comparison of the spectra of pure E2 protein proteolysis products and E2 protein stoichiometric complexes with antibodies. The absence of a specific peptide among the products of proteolysis of the complex indicates close contact between some amino acids of the peptide with an antibody, i.e. overlapping of the peptide sequence with the desired epitope for this antibody. It should be noted that the interaction between the antigen and the antibody itself does not change the spectrum of proteolysis products as the proteolytic reaction is preceded by the reduction of disulphide bonds and alkylation of the samples, leading to the destruction of the antigen-antibody complexes. Furthermore, the formation of the antigen-antibody complex may prevent a chemical reaction binding crosslinking reagent molecules with the antigen amino acids which are in close proximity to the antibody. As a result, peptides comprising these amino acids are free of crosslinking reagent, do not pass primary selection and drop out of observation.

Table. 3 shows the sequences of pure E2 protein proteolysis products carrying one molecule of crosslinking reagent. Tables 4-6 show the peptides from Table. 3 which are not present among the proteolysis of the E2 protein complexes with antibodies RYB1, RYB2 and RYB3.

TABLE 3

E2 protein proteolysis products carrying one molecule of crosslinking reagent. The coordinates of the first and last amino acids of the peptide are stated, as well as the coordinates of the amino acid covalently bonded to the crosslinking reagent.

| Peptide sequence | First amino acid | Last amino acid | Proteolysis enzyme | Amino acid bound to the crosslinking reagent | |
|---|---|---|---|---|---|
| ETHVTGGSAGRTTAGLVGLL (SEQ ID NO: 61) | 384 | 403 | chymotrypsin | His | 386 |
| ETHVTGGSAGRTTAGLVGLL (SEQ ID NO: 61) | 384 | 403 | chymotrypsin | Ser | 391 |
| ETHVTGGSAGRTTAGLVGLL (SEQ ID NO: 61) | 384 | 403 | chymotrypsin | Arg | 394 |
| ETHVTGGSAGRTTAGLVGLL (SEQ ID NO: 61) | 384 | 403 | chymotrypsin | Thr | 396 |
| TPGAKQNIQLINTNGSW (SEQ ID NO: 62) | 404 | 420 | chymotrypsin | Lys | 408 |
| TPGAKQNIQLINTNGSW (SEQ ID NO: 62) | 404 | 420 | chymotrypsin | Ser | 419 |
| INTNGSW (SEQ ID NO: 63) | 414 | 420 | chymotrypsin | Ser | 419 |
| NCNESLNTGWL (SEQ ID NO: 64) | 428 | 438 | chymotrypsin | Ser | 432 |
| NCNESLNTGWL (SEQ ID NO: 64) | 428 | 438 | chymotrypsin | Thr | 435 |
| AQGWGPISY (SEQ ID NO: 65) | 466 | 474 | chymotrypsin | Ser | 473 |
| GPISYANGSGLDERPY (SEQ ID NO: 66) | 470 | 485 | chymotrypsin | Ser | 473 |
| AQGWGPISY (SEQ ID NO: 65) | 466 | 474 | chymotrypsin | Tyr | 474 |
| GPISYANGSGLDERPY (SEQ ID NO: 66) | 470 | 485 | chymotrypsin | Ser | 478 |
| ANGSGLDERPY (SEQ ID NO: 67) | 475 | 485 | chymotrypsin | Ser | 478 |
| ANGSGLDERPYCW (SEQ ID NO: 68) | 475 | 487 | chymotrypsin | Ser | 478 |
| GPISYANGSGLDERPY (SEQ ID NO: 66) | 470 | 485 | chymotrypsin | Arg | 483 |
| ANGSGLDERPY (SEQ ID NO: 67) | 475 | 485 | chymotrypsin | Arg | 483 |
| ANGSGLDERPYCW (SEQ ID NO: 68) | 475 | 487 | chymotrypsin | Arg | 483 |
| CWHYPPRPCGIVPAKSVCGPVY (SEQ ID NO: 69) | 486 | 507 | chymotrypsin | His | 488 |
| CWHYPPRPCGIVPAKSVCGPVY (SEQ ID NO: 69) | 486 | 507 | chymotrypsin | Arg | 492 |
| HYPPRPCGIVPAKSVCGPVY (SEQ ID NO: 70) | 488 | 507 | chymotrypsin | Arg | 492 |

TABLE 3-continued E2 protein proteolysis products carrying one molecule of crosslinking reagent. The coordinates of the first and last amino acids of the peptide are stated, as well as the coordinates of the amino acid covalently bonded to the crosslinking reagent.

| Peptide sequence | First amino acid | Last amino acid | Proteolysis enzyme | Amino acid bound to the crosslinking reagent | |
|---|---|---|---|---|---|
| HYPPRPCGIVPAKSVCGPVY (SEQ ID NO: 70) | 488 | 507 | chymotrypsin | Lys | 500 |
| PCGIVPAK (SEQ ID NO: 72) | 493 | 500 | trypsin | Lys | 500 |
| PCGIVPAKSVCGPVYCFTPSPVVVGTTDR (SEQ ID NO: 72) | 493 | 521 | trypsin | Lys | 500 |
| CGIVPAKSVCGPVYCFTPSPVWGTTDR (SEQ ID NO: 73) | 494 | 521 | trypsin | Lys | 500 |
| GIVPAKSVCGPVYCFTPSPVVVGTTDR (SEQ ID NO: 74) | 495 | 521 | trypsin | Lys | 500 |
| CWHYPPRPCGIVPAKSVCGPVY (SEQ ID NO: 69) | 486 | 507 | chymotrypsin | Ser | 501 |
| HYPPRPCGIVPAKSVCGPVY (SEQ ID NO: 70) | 488 | 507 | chymotrypsin | Ser | 501 |
| PCGIVPAKSVCGPVYCFTPSPVVVGTTDR (SEQ ID NO: 72) | 493 | 521 | trypsin | Ser | 501 |
| CGIVPAKSVCGPVYCFTPSPVVVGTTDR (SEQ ID NO: 73) | 494 | 521 | trypsin | Ser | 501 |
| GIVPAKSVCGPVYCFTPSPVVVGTTDR (SEQ ID NO: 74) | 495 | 521 | trypsin | Ser | 501 |
| PCGIVPAKSVCGPVYCFTPSPVVVGTTDR (SEQ ID NO: 72) | 493 | 521 | trypsin | Tyr | 507 |
| CGIVPAKSVCGPWCFTPSPVVVGTTDR (SEQ ID NO: 73) | 494 | 521 | trypsin | Tyr | 507 |
| GIVPAKSVCGPVYCFTPSPVVVGTTDR (SEQ ID NO: 74) | 495 | 521 | trypsin | Tyr | 510 |
| CFTPSPVVVGTTDRS (SEQ ID NO: 75) | 508 | 522 | chymotrypsin | Thr | 512 |
| PCGIVPAKSVCGPVYCFTPSPVVVGTTDR (SEQ ID NO: 72) | 493 | 521 | trypsin | Ser | 512 |
| CFTPSPVVVGTTDRSGAPTY (SEQ ID NO: 76) | 508 | 527 | chymotrypsin | Ser | 512 |
| CFTPSPVVVGTTDRS (SEQ ID NO: 75) | 508 | 522 | chymotrypsin | Ser | 512 |
| TPSPVWGTTDRSGAPTY (SEQ ID NO: 77) | 510 | 527 | chymotrypsin | Ser | 512 |
| CGIVPAKSVCGPVYCFTPSPVVVGTTDR (SEQ ID NO: 73) | 494 | 521 | trypsin | Ser | 512 |
| GIVPAKSVCGPVYCFTPSPVVVGTTDR (SEQ ID NO: 74) | 495 | 521 | trypsin | Ser | 512 |
| CFTPSPVVVGTTDR (SEQ ID NO: 78) | 508 | 521 | trypsin | Ser | 512 |
| FTPSPVVVGTTDR (SEQ ID NO: 79) | 509 | 521 | trypsin | Ser | 512 |
| CGIVPAKSVCGPVYCFPSPVVVGTTDR (SEQ ID NO: 73) | 494 | 521 | trypsin | Thr | 518 |

TABLE 3-continued

E2 protein proteolysis products carrying one molecule of crosslinking reagent. The coordinates of the first and last amino acids of the peptide are stated, as well as the coordinates of the amino acid covalently bonded to the crosslinking reagent.

| Peptide sequence | First amino acid | Last amino acid | Proteolysis enzyme | Amino acid bound to the crosslinking reagent | |
|---|---|---|---|---|---|
| GIVPAKSVCGPVYCFTPSPVVVGTTDR (SEQ ID NO: 74) | 495 | 521 | trypsin | Thr | 518 |
| PCGIVPAKSVCGPVYCFTPSPVVVGTTDR (SEQ ID NO: 72) | 493 | 521 | trypsin | Thr | 518 |
| CFTPSPVVVGTTDRSGAPTY (SEQ ID NO: 76) | 508 | 527 | chymotrypsin | Thr | 518 |
| CFTPSPVVVGTTDRS (SEQ ID NO: 75) | 508 | 522 | chymotrypsin | Thr | 518 |
| PCGIVPAKSVCGPVYCFTPSPVVVGTTDR (SEQ ID NO: 72) | 493 | 521 | trypsin | Thr | 518 |
| GIVPAKSVCGPVYCFTPSPVVVGTTDR (SEQ ID NO: 74) | 495 | 521 | trypsin | Thr | 518 |
| CFTPSPVVVGTTDR (SEQ ID NO: 78) | 508 | 521 | trypsin | Thr | 518 |
| FTPSPVVVGTTDR (SEQ ID NO: 79) | 509 | 521 | trypsin | Thr | 519 |
| TPSPVVVGTTDRSGAPTY (SEQ ID NO: 77) | 510 | 527 | chymotrypsin | Thr | 519 |
| PCGIVPAKSVCGPVYCFTPSPVVVGTTDR (SEQ ID NO: 74) | 493 | 521 | trypsin | Arg | 521 |
| CFTPSPVVVGTTDR (SEQ ID NO: 78) | 508 | 521 | trypsin | Arg | 521 |
| FTPSPVVVGTTDR (SEQ ID NO: 79) | 509 | 521 | trypsin | Arg | 521 |
| CFTPSPVVVGTTDRSGAPTY (SEQ ID NO: 76) | 508 | 527 | chymotrypsin | Ser | 522 |
| CFTPSPVVVGTTDRS (SEQ ID NO: 75) | 508 | 522 | chymotrypsin | Ser | 522 |
| TPSPVVVGTTDRSGAPTY (SEQ ID NO: 77) | 510 | 527 | chymotrypsin | Ser | 522 |
| MNSTGFTKVCGAPPCVIGGVGNNTLL (SEQ ID NO: 80) | 555 | 580 | chymotrypsin | Ser | 557 |
| MNSTGFTKVCGAPPCVIGGVGNNTLL (SEQ ID NO: 80) | 555 | 580 | chymotrypsin | Lys | 562 |
| TKVCGAPPCVIGGVGNNTLL (SEQ ID NO: 81) | 561 | 580 | chymotrypsin | Lys | 562 |
| MNSTGFTKVCGAPPCVIGGVGNNTLL (SEQ ID NO: 80) | 555 | 580 | chymotrypsin | Thr | 578 |
| TKVCGAPPCVIGGVGNNTLL (SEQ ID NO: 81) | 561 | 580 | chymotrypsin | Thr | 578 |
| CPTDCF (SEQ ID NO: 82) | 581 | 586 | chymotrypsin | Thr | 583 |
| RKHPEATYSRCGSGPW (SEQ ID NO: 83) | 587 | 602 | chymotrypsin | Arg | 587 |
| KHPEATYSRCGSGPWITPR (SEQ ID NO: 84) | 588 | 606 | trypsin | Lys | 588 |

TABLE 3-continued

E2 protein proteolysis products carrying one molecule of crosslinking reagent. The coordinates of the first and last amino acids of the peptide are stated, as well as the coordinates of the amino acid covalently bonded to the crosslinking reagent.

| Peptide sequence | First amino acid | Last amino acid | Proteolysis enzyme | Amino acid bound to the crosslinking reagent | |
|---|---|---|---|---|---|
| RKHPEATYSRCGSGPW (SEQ ID NO: 83) | 587 | 602 | chymotrypsin | Ser | 595 |
| SRCGSGPW (SEQ ID NO: 85) | 595 | 602 | chymotrypsin | Ser | 595 |
| KHPEATYSRCGSGPWITPR (SEQ ID NO: 84) | 588 | 606 | trypsin | Ser | 595 |
| HPEATYSRCGSGPWITPR (SEQ ID NO: 86) | 589 | 606 | trypsin | Ser | 595 |
| RKHPEATYSRCGSGPW (SEQ ID NO: 83) | 587 | 602 | chymotrypsin | Arg | 596 |
| SRCGSGPW (SEQ ID NO: 85) | 595 | 602 | chymotrypsin | Arg | 596 |
| KHPEATYSRCGSGPWITPR (SEQ ID NO: 84) | 588 | 606 | trypsin | Arg | 596 |
| HPEATYSRCGSGPWITPR (SEQ ID NO: 86) | 589 | 606 | trypsin | Arg | 596 |
| RKHPEATYSRCGSGPW (SEQ ID NO: 83) | 587 | 602 | chymotrypsin | Ser | 599 |
| SRCGSGPW (SEQ ID NO: 85) | 595 | 602 | chymotrypsin | Ser | 599 |
| KHPEATYSRCGSGPWITPR (SEQ ID NO: 84) | 588 | 606 | trypsin | Ser | 599 |
| HPEATYSRCGSGPWITPR (SEQ ID NO: 86) | 589 | 606 | trypsin | Ser | 599 |
| ITPRCMVDYPY (SEQ ID NO: 87) | 603 | 613 | chymotrypsin | Arg | 606 |
| KHPEATYSRCGSGPWITPR (SEQ ID NO: 88) | 588 | 603 | trypsin | Arg | 606 |
| HPEATYSRCGSGPWITPR (SEQ ID NO: 89) | 589 | 603 | trypsin | Arg | 606 |
| CGSGPWITPRCMVDYPYR (SEQ ID NO: 90) | 597 | 614 | trypsin | Arg | 606 |
| CGSGPWITPRCMVDYPYR (SEQ ID NO: 90) | 597 | 614 | trypsin | Tyr | 611 |
| ITPRCMVDYPY (SEQ ID NO: 87) | 603 | 613 | chymotrypsin | Tyr | 613 |
| CGSGPWITPRCMVDYPYR (SEQ ID NO: 90) | 597 | 614 | trypsin | Arg | 614 |
| CMVDYPYR (SEQ ID NO: 91) | 607 | 614 | trypsin | Arg | 614 |
| MYVGGVEHR (SEQ ID NO: 92) | 631 | 639 | trypsin | Tyr | 632 |
| VGGVEHRLEAACNW (SEQ ID NO: 93) | 633 | 646 | chymotrypsin | His | 638 |
| VGGVEHRL (SEQ ID NO: 94) | 633 | 640 | chymotrypsin | Arg | 639 |

TABLE 3-continued

E2 protein proteolysis products carrying one molecule of crosslinking reagent. The coordinates of the first and last amino acids of the peptide are stated, as well as the coordinates of the amino acid covalently bonded to the crosslinking reagent.

| Peptide sequence | First amino acid | Last amino acid | Proteolysis enzyme | Amino acid bound to the crosslinking reagent | |
|---|---|---|---|---|---|
| MYVGGVEHR (SEQ ID NO: 92) | 631 | 639 | trypsin | Arg | 639 |
| LEAACNWTR (SEQ ID NO: 95) | 640 | 648 | trypsin | Arg | 648 |
| GERCDLEDR (SEQ ID NO: 96) | 649 | 657 | trypsin | Arg | 651 |
| GERCDLEDR (SEQ ID NO: 96) | 649 | 657 | trypsin | Arg | 657 |
| LLSTTQW (SEQ ID NO: 97) | 666 | 672 | chymotrypsin | Ser | 668 |
| LLSTTQW (SEQ ID NO: 97) | 666 | 672 | chymotrypsin | Thr | 670 |
| HQNIVDVQY (SEQ ID NO: 98) | 693 | 701 | chymotrypsin | Tyr | 701 |
| LYGVGSSIASW (SEQ ID NO: 99) | 702 | 712 | chymotrypsin | Ser | 707 |
| YGVGSSIASW (SEQ ID NO: 100) | 703 | 712 | chymotrypsin | Ser | 707 |
| LYGVGSSIASW (SEQ ID NO: 99) | 702 | 712 | chymotrypsin | Ser | 708 |
| YGVGSSIASW (SEQ ID NO: 100) | 703 | 712 | chymotrypsin | Ser | 708 |
| LYGVGSSIASW (SEQ ID NO: 99) | 702 | 712 | chymotrypsin | Ser | 711 |
| YGVGSSIASW (SEQ ID NO: 100) | 703 | 712 | chymotrypsin | Ser | 711 |
| LADARVCSCLW (SEQ ID NO: 101) | 726 | 736 | chymotrypsin | Arg | 730 |
| ADARVCSCL (SEQ ID NO: 102) | 727 | 735 | chymotrypsin | Arg | 730 |
| ADARVCSCLW (SEQ ID NO: 103) | 727 | 736 | chymotrypsin | Arg | 730 |
| LADARVCSCLW (SEQ ID NO: 101) | 726 | 736 | chymotrypsin | Ser | 733 |
| ADARVCSCL (SEQ ID NO: 102) | 727 | 735 | chymotrypsin | Ser | 733 |
| ADARVCSCLW (SEQ ID NO: 103) | 727 | 736 | chymotrypsin | Ser | 733 |

TABLE 4

The peptides from Table 3 which are not present among the proteolysis products of the E2 protein complexes with antibody RYB1, which carry one crosslinking reagent molecule.

| Peptide sequence | First amino acid | Last amino acid | Proteolysis enzyme | Amino acid bound to the crosslinking reagent | |
|---|---|---|---|---|---|
| RKHPEATYSRCGSGPW (SEQ ID NO: 83) | 587 | 602 | chymotrypsin | Ser | 595 |
| SRCGSGPW (SEQ ID NO: 85) | 595 | 602 | chymotrypsin | Ser | 595 |
| KHPEATYSRCGSGPWITPR (SEQ ID NO: 84) | 588 | 606 | trypsin | Ser | 595 |
| HPEATYSRCGSGPWITPR (SEQ ID NO: 86) | 589 | 606 | trypsin | Ser | 595 |
| RKHPEATYSRCGSGPW (SEQ ID NO: 83) | 587 | 602 | chymotrypsin | Arg | 596 |
| SRCGSGPW (SEQ ID NO: 85) | 595 | 602 | chymotrypsin | Arg | 596 |
| KHPEATYSRCGSGPWITPR (SEQ ID NO: 84) | 588 | 606 | trypsin | Arg | 596 |
| HPEATYSRCGSGPWITPR (SEQ ID NO: 86) | 589 | 606 | trypsin | Arg | 596 |

TABLE 5

The peptides from Table 3 which are not present among the proteolysis products of the E2 protein complexes with antibody RYB2, which carry one crosslinking reagent molecule.

| Peptide sequence | First amino acid | Last amino acid | Proteolysis enzyme | Amino acid bound to the crosslinking reagent | |
|---|---|---|---|---|---|
| PCGQVPAKSVCGPVYCFTPSPVVVGTTDR (SEQ ID NO: 72) | 493 | 521 | trypsin | Tyr | 507 |
| CGIVPAKSVCGPVYCFTPSPVVVGTTDR (SEQ ID NO: 73) | 494 | 521 | trypsin | Tyr | 507 |
| GIVPAKSVCGPVYCFTPSPVVVGTTDR (SEQ ID NO: 74) | 495 | 521 | trypsin | Tyr | 507 |

TABLE 6

The peptides from Table 3 which are not present among the proteolysis products of the E2 protein complexes with antibody RYB3, which carry one crosslinking reagent molecule.

| Peptide sequence | First amino acid | Last amino acid | Proteolysis enzyme | Amino acid bound to the crosslinking reagent | |
|---|---|---|---|---|---|
| RKHPEATYSRCGSGPW (SEQ ID NO: 83) | 587 | 602 | chymotrypsin | Ser | 595 |
| SRCGSGPW (SEQ ID NO: 85) | 595 | 602 | chymotrypsin | Ser | 595 |
| KHPEATYSRCGSGPWITPR (SEQ ID NO: 84) | 588 | 606 | trypsin | Ser | 595 |
| HPEATYSRCGSGPWITPR (SEQ ID NO: 86) | 589 | 606 | trypsin | Ser | 595 |
| RKHPEATYSRCGSGPW (SEQ ID NO: 83) | 587 | 602 | chymotrypsin | Arg | 596 |

TABLE 6-continued

The peptides from Table 3 which are not present among the proteolysis products of the E2 protein complexes with antibody RYB3, which carry one crosslinking reagent molecule.

| Peptide sequence | First amino acid | Last amino acid | Proteolysis enzyme | Amino acid bound to the crosslinking reagent | |
|---|---|---|---|---|---|
| SRCGSGPW (SEQ ID NO: 85) | 595 | 602 | chymotrypsin | Arg | 596 |
| KHPEATYSRCGSGPWITPR (SEQ ID NO: 84) | 588 | 606 | trypsin | Arg | 596 |
| HPEATYSRCGSGPWITPR (SEQ ID NO: 86) | 589 | 606 | trypsin | Arg | 596 |
| RKHPEATYSRCGSGPW (SEQ ID NO: 83) | 587 | 602 | chymotrypsin | Ser | 599 |
| SRCGSGPW (SEQ ID NO: 85) | 595 | 602 | chymotrypsin | Ser | 599 |
| KHPEATYSRCGSGPWITPR (SEQ ID NO: 84) | 588 | 606 | trypsin | Ser | 599 |
| HPEATYSRCGSGPWITPR (SEQ ID NO: 86) | 589 | 606 | trypsin | Ser | 599 |

Analysis of the arrangement of the crosslinking reagent molecules on the peptide products of the E2 protein proteolysis before and after the formation of complexes with an antibody makes it possible to very accurately locate the regions of E2 which come into contact with the antibody. Thus, in the case of the antibody RYB1, the amino acids of the E2 protein on the regions from the N-terminus to lysine Lys588, inclusive, and beginning from serine Ser599 to the C-terminus, retain the ability to bind with the crosslinking reagent independently of the formation of a complex with the antibody (FIG. 6). In addition, the amino acids serine Ser595 and arginine Arg596 lose the ability to bind with the crosslinking reagent after the complex has been formed. On the basis of these data, it can be concluded that the E2 protein epitope for the antibody RYB1 (epitope Ep1) is a continuous amino acid sequence comprising the amino acids Ser595 and Arg596 and enclosed within the region HPEATYSRCG (589-598) (SEQ ID NO: 30). It is most likely that the epitope is the central fragment of this region of 6 amino acids: EATYSR (591-596) (SEQ ID NO: 31). This epitope is not described in the literature.

In the case of the antibody RYB2, the amino acids of the E2 protein on the regions from the N-terminus to serine Ser501, inclusive, and beginning from threonine Thr510 to the C-terminus, retain the ability to bind with the crosslinking reagent independently of the formation of a complex with the antibody (FIG. 7). In addition, the amino acid tyrosine Tyr507 loses the ability to bind with the crosslinking reagent after the complex has been formed. On the basis of these data, it can be concluded that the E2 protein epitope for the antibody RYB2 (epitope Ep2) is a continuous amino acid sequence comprising the amino acid Tyr507 and enclosed within the region VCGPVYCF (502-509) (SEQ ID NO: 32). It is most likely that the epitope is the central fragment of this region of 6 amino acids: CGPVYC (503-508) (SEQ ID NO: 33). This epitope is not described in the literature.

In the case of the antibody RYB3, the amino acids of the E2 protein on the regions from the N-terminus to lysine Lys588, inclusive, and beginning from arginine Arg606 to the C-terminus, retain the ability to bind with the crosslinking reagent independently of the formation of a complex with the antibody (FIG. 8). In addition, the amino acids serine Ser595, arginine Arg596 and serine Ser599 lose the ability to bind with the crosslinking reagent after the complex has been formed. On the basis of these data, it can be concluded that the E2 protein epitope for the antibody RYB3 (epitope Ep3) is a continuous amino acid sequence comprising the amino acids Ser595, Arg596 and Ser599 and enclosed within the region HPEATYSRCGSGPWITP (589-605) (SEQ ID NO: 34). It is most likely that the epitope is the inner fragment of this region of 6 amino acids: YSRCGS (594-599) (SEQ ID NO: 35) or SRCGSG (595-600) (SEQ ID NO: 36). This epitope is not described in the literature.

It should be noted that the epitopes Ep1 and Ep3 have the amino acids Ser595 and Arg596 arginine in common and therefore overlap, which is consistent with experimental data on the mutual competition of antibodies (Example 9). Analysis of the obtained sequences of epitopes shows (tab. 7) that epitope Ep2 is absolutely conserved for all genotypes. Epitopes Ep1 and Ep3 contain both conservative and variable amino acids.

TABLE 7

Homology of the sequences of the epitopes and surrounding regions of the E2 protein of HCV of different genotypes. The most likely sequences of epitopes are indicated in bold. The amino acid sequences of the E2 protein of various genotypes were taken from the work of Sabo et al. (Sabo MC, Luca VC, Prentoe J, Hopcraft SE, Blight KJ, Yi M, Lemon SM, Ball JK, Bukh J, Evans MJ, Fremont DH, Diamond MS J Virol 2011, 85 (14): 7005-7019).

| Virus Genotype | Virus isolate | Epitope Ep1 | Epitope Ep2 | Epitope Ep3 |
|---|---|---|---|---|
| 1 | H77 | HPEATYSRCG (SEQ ID NO: 30) | VCGPVYCF (SEQ ID NO: 32) | HPEATYSRCGSGPWITP (SEQ ID NO: 34) |
| 2 | J6 | HPDTTYLKCG (SEQ ID NO: 104) | VCGPVYCF (SEQ ID NO: 32) | HPDTTYLKCGSGPWLTP (SEQ ID NO: 105) |
| 3 | UKN 3a | HPEATYSRCG (SEQ ID NO: 30) | VCGPVYCF (SEQ ID NO: 32) | HPEATYSRCGSGPWLTP (SEQ ID NO: 106) |
| 4 | UKN 4a | HPETTYAKCG (SEQ ID NO: 107) | VCGPVYCF (SEQ ID NO: 32) | HPETTYAKCGSGPWITP (SEQ ID NO: 108) |
| 5 | SA13 | HPDATYTKCG (SEQ ID NO: 109) | VCGPVYCF (SEQ ID NO: 32) | HPDATYTKCGSGPWLTP (SEQ ID NO: 110) |
| 6 | UKN 6 | HPEATYQRCG (SEQ ID NO: 111) | VCGPVYCF (SEQ ID NO: 32) | HPEATYQRCGSGPWLTP (SEQ ID NO: 112) |

EXAMPLE 12

Determination of the Conformational Nature of the Epitopes

The fact that it was not possible to observe the reaction of antibodies RYB1, RYB2 and RYB3 with the E2 protein by Western-analysis suggests that the epitopes for these antibodies, which were established in Example 11, are conformational in nature. To verify this assumption, a series of experiments were made to determine the ability of short peptides containing epitopes to compete with full-length recombinant protein E2 for binding to antibodies. Since short peptides do not retain the conformation of the starting protein, a positive result of the experiments regarding competition would indicate that the recognition of epitopes by antibodies does not depend on the conformational structure of epitopes and is only determined by the amino acid sequences thereof (linear nature of the epitopes). Conversely, a negative result would indicate the importance of the conformational structure for interacting with these antibodies (conformational nature of the epitopes).

A set of peptides was obtained by proteolysis of recombinant E2 protein using immobilized pepsin in the following conditions. 5 µl of a suspension of agarose carrier with immobilized pepsin (Thermo Scientific, USA) was added to a 25 µl solution of E2 protein (see example 10) in PBS with a concentration of 13 mM, and incubated for 30 minutes at room temperature. After incubation the samples were centrifuged and the supernatant containing the proteolytic products was transferred to other test tubes. The reaction conditions were optimized to obtain most of the peptide products in the range of 1000-3500 Da (8-30 amino acid residues). Pepsin has little specificity regarding hydrolyzable peptide bonds, so it is expected that the representativeness of any short sequences of a starting protein, in particular epitopes for antibodies RYB1, RYB2 and RYB3, among proteolysis products is about the same, and corresponds to the molar concentration of the starting protein.

Competition binding experiments were carried out under the following conditions. 5 µl of a preparation of one of the antibodies RYB1, RYB2 or RYB3 with a concentration of 4 µM was added to 5 µl of a peptide mixture sample with a concentration of 13 µM (according to staring protein E2) and incubated for 6 hours at 37° C. The concentration of peptides in the sample provided a clear excess of epitope sequences relative to the concentration of antibody binding centers (1625:1). Then, 10 µl of a solution of recombinant E2 protein with a concentration of 4 µM was added to the reaction mixture and treatment was carried out using stabilizing agent K200 as described in Example 10. The samples then underwent mass spectrometric analysis using MALDI technology with the aid of the time-of-flight mass analyzer Ultraflex III MALDI TOF TOF as described in the same example.

The results of the experiments showed (FIG. 9) that short peptides comprising epitopes do not inhibit the binding of a full length E2 protein to antibodies. Protein complexes are formed in the presence of an excess quantity of peptides, which have an identical molecular structure to that of the E2 protein complexes with antibodies, which are characterized in Example 6. Based on these data it can be concluded that binding antibodies RYB1, RYB2 and RYB3 to epitopes thereof is only possible with certain conformations of epitopes in the spatial structure of a molecule of protein E2. Thus, the epitopes of these antibodies are conformational in nature.

EXAMPLE 13

Investigation of the Neutralizing Activity of the Antibodies

The neutralizing activity of the antibodies, i.e. the ability of antibodies RYB1, RYB2 and RYB3 to prevent cells from becoming infected with the virus, was studied on the model of a human hepatocellular carcinoma cell culture, Huh-7 with the use of pseudo-viral particles HCVpp. HCVpp particles are pseudolentiviral particles carried as E1-E2 envelope protein complexes of the hepatitis C virus (Bartosch B, Dubuisson J, Cosset F L. J Exp Med 2003, 197 (5): 633-642).

The pseudo-viral particles HCVpp were prepared as described below. HEK293-TN cells (System Biosciences, USA), which express the large T antigen of the SV40 virus, were grown in T225 flasks (Corning, USA) in a DMEM medium with high quantity of glucose, which additionally contains 10% inactivated fetal bovine serum (Invitrogen, USA) and 2 mM glutamine, to a density of up to 70% of a monolayer. Immediately before transfection, the medium in the vials was changed for a fresh DMEM medium containing 2% fetal bovine serum. Transfection of cells was carried out with a mixture of plasmids pCMVdeltaR8.2, pSIH-CMV-CopGFP-H1 (MonA Ltd., Moscow) and pcDNA3.1-E1E2 (see. Example 3) using the reagent Lipofectamine 2000 (Invitrogen, USA). 225 µl of the reagent Lipofectamine 2000 was added to 1.5 ml serum-free DMEM medium, mixed by pipetting and added dropwise to a pre-prepared solution of a mixture of plasmids (54 µg pCMVdeltaR8.2, 18 µg pSIH-CMV-CopGFPHI and 18 µg pcDNA3.1-E1E2 in 1.5 mL serum-free DMEM medium). The resultant solution was stirred and incubated for 15 min and poured into a flask with the HEK293-TN cells. The cells were incubated for 24 hours at 37° C. in a $CO_2$ incubator in an atmosphere of 5% $CO_2$, after which the culture medium was replaced with fresh medium and the cells were incubated for 48 hours. After incubation, the culture medium containing the HCVpp particles was collected and filtered through cellulose acetate membrane filters with a pore size of 0.22 µm (Corning, USA). Portions of the medium were frozen and stored at −80° C.

The plasmid pCMVdeltaR8.2 contains the genes gag-pol and rev of the human immunodeficiency virus (HIV), the expression products of which are necessary for packaging pseudolentiviral particles and incorporating the viral genome into the genomic DNA of the infected host cell. The plasmid pSIH-CMV-CopGFP-H1 encodes the genomic RNA of the lentiviral vector based on HIV and carries in its structure the gene of green fluorescent protein CopGFP of the copepod Pontellina plumata under the control of a highly effective promotor of cytomegalovirus early genes. The plasmid pcDNA3.1-E1E2 encodes proteins E1 and E2 of the HCV envelope. During the simultaneous expression of genes of the above three plasmids in transfected cells, the cells produce the pseudoviral particles HCVpp in the culture medium, the interior of which is lentivector genomic RNA in a complex with the products of the genes gag-pol and rev, and the HCV protein complex E1-E2 serves as an envelope. Such particles can infect Huh-7 cells by a mechanism similar to the mechanism for infecting liver cells with the HCV virus. Thus the CopGFP gene, in the structure of the lentivector genome, integrates into the DNA of the infected cell and is expressed to form a fluorescent product, which makes it possible to detect infection by means of the fluorometric method.

An experiment to measure the neutralizing activity of the antibodies was performed as follows. Solutions of the antibodies RYB1, RYB2 and RYB3 were prepared with a concentration of 1 mg/ml. A composition of antibodies RYB1:RYB2:RYB3=1:1:1 was prepared by mixing 200 µl of an RYB1 solution, 200 µl of an RYB2 solution and 200 µl of an RYB3 solution. A composition of antibodies RYB1:RYB2:RYB3=20:40:40 was prepared by mixing 100 µl of an RYB1 solution, 200 µl of an RYB2 solution and 200 µl of an RYB3 solution. A composition of antibodies RYB1:RYB2: RYB3=40:20:40 was prepared by mixing 200 µl of an RYB1 solution, 100 µl of an RYB2 solution and 200 µl of an RYB3 solution. Lastly, a composition of antibodies RYB1:RYB2: RYB3=40:40:20 was prepared by mixing 200 µl of an RYB1 solution, 200 µl of an RYB2 solution and 100 µl of an RYB3 solution.

100 µl of solution of antibodies RYB1, RYB2 and RYB3 at a concentration of 1 mg/ml or 100 µl of one of the prepared compositions were added to 1.9 ml of cultured medium comprising the pseudoviral particles HCVpp, and incubated for 1 hour at 37° C. The total antibody concentration in all of the samples of the incubation mixture was 50 µg/ml. The human monoclonal antibody Adalimumab was used as a negative control, which was also added to a final concentration of 50 µg/ml. Huh-7 cells were grown in wells of 6 well culture plates (Corning, USA) in a DMEM medium additionally containing 10% inactivated fetal bovine serum (Invitrogen, USA) and 2 mM glutamine to a state of a density of 30% of a monolayer. In order to infect the cells, the culture medium in the plate wells was replaced with preincubated mixtures of HCVpp particles with antibodies, or compositions thereof, and incubated for 3 hours at 37° C. in a $CO_2$ incubator. After incubation the medium in the plates was replaced with a fresh medium, the cells were cultured for a further 4 days and were subjected to fluorometric analysis on the FACS-Calibur flow cytometer (BD Biosciences, USA). Infection effectiveness was determined as a percentage of fluorescent cells in the sample. The analysis results are shown in Table. 16. As can be seen, the antibodies RYB1, RYB2 and RYB3 exhibit significant neutralizing activity (inhibition of infection in 22-36 times), which opens up the possibility of their wide use in clinical practice. Furthermore, the highest neutralization result is shown by the composition of the three antibodies in a ratio of 1:1:1 (infection inhibition in 53.6 times), and a reduction the content of any antibody in the composition to 20% causes a reduction of neutralizing activity.

TABLE 8

Measuring the neutralizing activity of the antibodies.

| Antibody or composition of antibodies | Infection effectiveness (percentage of fluorescent cells) | Degree of inhibition (times) |
| --- | --- | --- |
| — | 63.3 | 1 |
| Adalimumab | 58.1 | 1.09 |
| RYB1 | 1.93 | 32.8 |
| RYB2 | 2.87 | 22.1 |
| RYB3 | 1.73 | 36.6 |
| RYB1:RYB2:RYB3 = 1:1:1 | 1.18 | 53.6 |
| RYB1:RYB2:RYB3 = 20:40:40 | 1.41 | 44.9 |
| RYB1:RYB2:RYB3 = 40:20:40 | 1.34 | 47.2 |
| RYB1:RYB2:RYB3 = 40:40:20 | 1.67 | 37.9 |

Thus, experiments studying the neutralizing activity of the antibodies in a model system of human hepatocellular carcinoma cells, Huh-7 demonstrated the ability of the antibodies and compositions thereof to effectively inhibit cell infection using pseudoviral particles HCVpp. The degree of inhibition with the optimal selection of composition reaches about 53 times, which indicates the potential usefulness of these antibodies and compositions thereof for clinical use in the prevention and treatment of hepatitis C.

The invention claimed is:

1. A fully human monoclonal antibody RYB1 with an amino acid sequence of the variable region of a heavy chain (V$_H$) SEQ ID NO: 5 and an amino acid sequence of the variable region of a light chain (V$_L$) SEQ ID NO: 9, which has immunologic specificity for the epitope Ep1 of the E2 protein of hepatitis C virus isolate H77, wherein said epitope consists of a conformation of the continuous amino acid sequence HPEATYSRCG (SEQ ID NO: 30), and said antibody being secreted by cells of the hybrid (mouse/human) cell line BIONA-RYB1, deposited in the Russian National Collection of Industrial Microorganisms under number H-142.

2. A fully human monoclonal antibody RYB2 with an amino acid sequence of the variable region of a heavy chain (V$_H$) SEQ ID NO: 13 and an amino acid sequence of the variable region of a light chain (V$_L$) SEQ ID NO: 17, which has immunologic specificity for the epitope Ep2 of the E2 protein of hepatitis C virus isolate H77, wherein said epitope consists of a conformation of the continuous amino acid sequence VCGPVYCF (SEQ ID NO: 32), and said antibody being secreted by cells of the hybrid (mouse/human) cell line BIONA-RYB2, deposited in the Russian National Collection of Industrial Microorganisms under number H-143.

3. A fully human monoclonal antibody RYB3 with an amino acid sequence of the variable region of a heavy chain (V$_H$) SEQ ID NO: 21 and an amino acid sequence of the variable region of a light chain (V$_L$) SEQ ID NO: 25, which has immunologic specificity for the epitope Ep3 of the E2 protein of hepatitis C virus isolate H77, wherein said epitope consists of a conformation of the continuous amino acid sequence HPEATYSRCGSGPWITP (SEQ ID NO: 34), and said antibody being secreted by cells of the hybrid (mouse/human) cell line BIONA-RYB3, deposited in the Russian National Collection of Industrial Microorganisms under number H-144.

4. A composition based on antibodies having immunological specificity for epitopes Ep1, Ep2 and Ep3 of the E2 protein, which is characterized in that it contains the fully human monoclonal antibodies RYB1, RYB2 and RYB3 as antibodies and in the mass ratio 20-40:20-40:20-40.

5. The composition according to claim 4, which is characterized in that the ratio of antibodies RYB1, RYB2 and RYB3 in the composition is 1:1:1.

6. The hybrid mouse/human cell line BIONA-RYB1, deposited in the Russian National Collection of Industrial Microorganisms under number H-142, which produces fully human monoclonal antibodies to epitope Ep1 of the E2 protein of hepatitis C virus isolate H77.

7. The hybrid mouse/human cell line BIONA-RYB2, deposited in the Russian National Collection of Industrial Microorganisms under number H-143, which produces fully human monoclonal antibodies to epitope Ep2 of the E2 protein of hepatitis C virus isolate H77.

8. The hybrid mouse/human cell line BIONA-RYB3, deposited in the Russian National Collection of Industrial Microorganisms under number H-144, which produces fully human monoclonal antibodies to epitope Ep3 of the E2 protein of hepatitis C virus isolate H77.

9. A method for neutralizing the hepatitis C virus, wherein the method comprises administering to a patient a fully human monoclonal antibody which binds to an epitope of E2 protein of the hepatitis C viral envelope, wherein the fully human monoclonal antibody is a composition based on antibodies having immunological specificity for epitopes Ep1, Ep2 and Ep3 of the E2 protein, which is characterized in that it contains the fully human monoclonal antibodies RYB1, RYB2 and RYB3 as antibodies and in the mass ratio 20-40:20-40:20-40.

10. The method of claim 9, wherein the composition is characterized in that the ratio of antibodies RYB1, RYB2 and RYB3 in the composition is 1:1:1.

11. A method for neutralizing the hepatitis C virus, wherein the method comprises: administering to a patient the fully human monoclonal antibody of claim 1.

12. A method for neutralizing the hepatitis C virus, wherein the method comprises: administering to a patient the fully human monoclonal antibody of claim 2.

13. A method for neutralizing the hepatitis C virus, wherein the method comprises: administering to a patient the fully human monoclonal antibody of claim 3.

14. A method for neutralizing the hepatitis C virus, wherein the method comprises: administering to a patient a fully human monoclonal antibody which binds to an epitope of E2 protein of the hepatitis C viral envelope, wherein the fully human monoclonal antibody is produced by the hybrid mouse/human cell line of claim 6.

15. A method for neutralizing the hepatitis C virus, wherein the method comprises: administering to a patient a fully human monoclonal antibody which binds to an epitope of E2 protein of the hepatitis C viral envelope, wherein the fully human monoclonal antibody is produced by the hybrid mouse/human cell line of claim 7.

16. A method for neutralizing the hepatitis C virus, wherein the method comprises: administering to a patient a fully human monoclonal antibody which binds to an epitope of E2 protein of the hepatitis C viral envelope, wherein the fully human monoclonal antibody is produced by the hybrid mouse/human cell line of claim 8.

* * * * *

SEQUENCE LISTING

<160> NUMBER OF SEQ ID NOS: 115

<210> SEQ ID NO 1
<211> LENGTH: 1845
<212> TYPE: DNA
<213> ORGANISM: Hepatitis C Virus, H77 isolate
<300> PUBLICATION INFORMATION:
<308> DATABASE ACCESSION NUMBER: NCBI Nucleotide / NC_004102.1
<309> DATABASE ENTRY DATE: 2009-06-18
<313> RELEVANT RESIDUES IN SEQ ID NO: (735)..(2579)

<400> SEQUENCE: 1

| | | | | | | |
|---|---|---|---|---|---|---|
| gacctcatgg | ggtacatacc | gctcgtcggc | gcccctcttg | gaggcgctgc | cagggccctg | 60 |
| gcgcatggcg | tccgggttct | ggaagacggc | gtgaactatg | caacagggaa | ccttcctggt | 120 |
| tgctctttct | ctatcttcct | tctggccctg | ctctcttgcc | tgactgtgcc | cgcttcagcc | 180 |
| taccaagtgc | gcaattcctc | ggggctttac | catgtcacca | atgattgccc | taactcgagt | 240 |
| attgtgtacg | aggcggccga | tgccatcctg | cacactccgg | ggtgtgtccc | ttgcgttcgc | 300 |
| gagggtaacg | cctcgaggtg | ttgggtggcg | gtgaccccca | cggtggccac | cagggacggc | 360 |
| aaactcccca | caacgcagct | tcgacgtcat | atcgatctgc | ttgtcgggag | cgccaccctc | 420 |
| tgctcggccc | tctacgtggg | ggacctgtgc | gggtctgtct | tcttgttgg | tcaactgttt | 480 |
| accttctctc | ccaggcgcca | ctggacgacg | caagactgca | attgttctat | ctatcccggc | 540 |
| catataacgg | gtcatcgcat | ggcatgggat | atgatgatga | actggtcccc | tacggcagcg | 600 |
| ttggtggtag | ctcagctgct | ccggatccca | caagccatca | tggacatgat | cgctggtgct | 660 |
| cactggggag | tcctggcggg | catagcgtat | ttctccatgg | tggggaactg | ggcgaaggtc | 720 |
| ctggtagtgc | tgctgctatt | tgccggcgtc | gacgcggaaa | cccacgtcac | cggggggaagt | 780 |
| gccggccgca | ccacggctgg | gcttgttggt | ctccttacac | caggcgccaa | gcagaacatc | 840 |
| caactgatca | acaccaacgg | cagttggcac | atcaatagca | cggccttgaa | ctgcaatgaa | 900 |
| agccttaaca | ccggctggtt | agcagggctc | ttctatcagc | acaaattcaa | ctcttcaggc | 960 |
| tgtcctgaga | ggttggccag | ctgccgacgc | cttaccgatt | tgcccagggg | ctggggtcct | 1020 |
| atcagttatg | ccaacggaag | cggcctcgac | gaacgcccct | actgctggca | ctaccctcca | 1080 |
| agaccttgtg | gcattgtgcc | cgcaaagagc | gtgtgtggcc | cggtatattg | cttcactccc | 1140 |
| agccccgtgg | tggtgggaac | gaccgacagg | tcgggcgcgc | ctacctacag | ctggggtgca | 1200 |
| aatgatacgg | atgtcttcgt | ccttaacaac | accaggccac | cgctgggcaa | ttggttcggt | 1260 |
| tgtacctgga | tgaactcaac | tggattcacc | aaagtgtgcg | gagcgccccc | ttgtgtcatc | 1320 |
| ggagggggtgg | gcaacaacac | cttgctctgc | cccactgatt | gtttccgcaa | gcatccggaa | 1380 |
| gccacatact | ctcggtgcgg | ctccggtccc | tggattacac | ccaggtgcat | ggtcgactac | 1440 |
| ccgtataggc | tttggcacta | tccttgtacc | atcaattaca | ccatattcaa | agtcaggatg | 1500 |
| tacgtgggag | gggtcgagca | caggctgaa | gcggcctgca | actggacgcg | gggcgaacgc | 1560 |
| tgtgatctgg | aagacaggga | caggtccgag | ctcagcccat | tgctgctgtc | caccacacag | 1620 |
| tggcaggtcc | ttccgtgttc | tttcacgacc | ctgccagcct | tgtccaccgg | cctcatccac | 1680 |
| ctccaccaga | acattgtgga | cgtgcagtac | ttgtacgggg | tagggtcaag | catcgcgtcc | 1740 |
| tgggccatta | agtgggagta | cgtcgttctc | ctgttcctcc | tgcttgcaga | cgcgcgcgtc | 1800 |
| tgctcctgct | tgtggatgat | gttactcata | tcccaagcgg | aggcg | | 1845 |

<210> SEQ ID NO 2
<211> LENGTH: 27

```
<212> TYPE: DNA
<213> ORGANISM: Artificial Sequence
<220> FEATURE:
<223> OTHER INFORMATION: A linker synthesized in the laboratory,
      contains Acc65I restriction site, ribosomal binding site, and
      encoding amino acids Met, Asn, Ser

<400> SEQUENCE: 2
gcaggtaccg ccgccgccat gaattcc                                         27

<210> SEQ ID NO 3
<211> LENGTH: 12
<212> TYPE: DNA
<213> ORGANISM: Artificial Sequence
<220> FEATURE:
<223> OTHER INFORMATION: A linker synthesized in the laboratory,
      contains termination translation signal and XbaI restriction site

<400> SEQUENCE: 3
taatctagag cg                                                         12

<210> SEQ ID NO 4
<211> LENGTH: 1884
<212> TYPE: DNA
<213> ORGANISM: Artificial Sequence
<220> FEATURE:
<223> OTHER INFORMATION: Recombinant DNA encoding amino acids Met, Asn,
      Ser, 60 Q-terminal amino acids of the Core protein (HCV
      polyprotein amino acids 132-191), protein E1 (HCV polyprotein
      amino acids 192-383), and protein E2 (HCV polyprotein amino acids
      384-746)

<400> SEQUENCE: 4
gcaggtaccg ccgccgccat gaattccgac ctcatggggt acataccgct cgtcggcgcc      60
cctcttggag gcgctgccag ggccctggcg catggcgtcc gggttctgga agacggcgtg     120
aactatgcaa cagggaacct tcctggttgc tcttctctca tcttccttct ggccctgctc     180
tcttgcctga ctgtgcccgc ttcagcctac caagtgcgca attcctcggg gctttaccat     240
gtcaccaatg attgccctaa ctcgagtatt gtgtacgagg cggccgatgc catcctgcac     300
actccggggt gtgtcccttg cgttcgcgag ggtaacgcct cgaggtgttg ggtggcggtg     360
acccccacgg tggccaccag ggacggcaaa ctccccacaa cgcagcttcg acgtcatatc     420
gatctgcttg tcgggagcgc caccctctgc tcggccctct acgtggggga cctgtgcggg     480
tctgtctttc ttgttggtca actgtttacc ttctctccca ggcgccactg gacgacgcaa     540
gactgcaatt gttctatcta tcccggccat ataacgggtc atcgcatggc atgggatatg     600
atgatgaact ggtcccctac ggcagcgttg gtggtagctc agctgctccg gatcccacaa     660
gccatcatgg acatgatcgc tggtgctcac tggggagtcc tggcgggcat agcgtatttc     720
tccatggtgg ggaactgggc gaaggtcctg gtagtgctgc tgctatttgc cggcgtcgac     780
gcggaaaccc acgtcaccgg gggaagtgcc ggccgcacca cggctgggct tgttggtctc     840
cttacaccag gcgccaagca gaacatccaa ctgatcaaca ccaacggcag ttggcacatc     900
aatagcacgg ccttgaactg caatgaaagc cttaacaccg gctggttagc agggctcttc     960
tatcagcaca aattcaactc ttcaggctgt cctgagaggt tggccagctg ccgacgcctt    1020
accgattttg cccagggctg ggtcctatc agttatgcca acggaagcgg cctcgacgaa     1080 cgccccctact gctggcacta ccctccaaga ccttgtggca ttgtgccgc aaagagcgtg    1140 tgtggcccgt atattgctt cactcccagc ccgtggtgg tgggaacgac cgacaggtcg     1200
ggcgcgccta cctacagctg gggtgcaaat gatacggatg tcttcgtcct aaacaacacc    1260
```

-continued

```
aggccaccgc tgggcaattg gttcggttgt acctggatga actcaactgg attcaccaaa    1320
gtgtgcggag cgccccctgt gtcatcgga ggggtgggca acaacacctt gctctgcccc    1380
actgattgtt tccgcaagca tccggaagcc acatactctc ggtgcggctc cggtccctgg    1440
attacaccca ggtgcatggt cgactacccg tataggcttt ggcactatcc ttgtaccatc    1500
aattacacca tattcaaagt caggatgtac gtgggagggg tcgagcacag gctggaagcg    1560
gcctgcaact ggacgcgggg cgaacgctgt gatctggaag acaggacag gtccgagctc    1620 agcccattgc tgctgtccac cacacagtgg caggtcctcc cgtgttcttt cacgaccctg    1680
ccagccttgt ccaccggcct catccacctc caccagaaca ttgtggacgt gcagtacttg    1740
tacggggtag ggtcaagcat cgcgtcctgg gccattaagt gggagtacgt cgttctcctg    1800
ttcctcctgc ttgcagacgc gcgcgtctgc tcctgcttgt ggatgatgtt actcatatcc    1860
caagcggagg cgtaatctag agcg                                            1884
```

<210> SEQ ID NO 5
<211> LENGTH: 128
<212> TYPE: PRT
<213> ORGANISM: Homo sapiens
<220> FEATURE:
<221> NAME/KEY: DOMAIN
<222> LOCATION: (1)..(128)
<223> OTHER INFORMATION: RYB1 VH region

<400> SEQUENCE: 5

```
Leu Leu Gln Leu Gln Glu Ser Gly Ser Gly Leu Val Lys Thr Ser Gln
1               5                   10                  15

Thr Leu Ser Leu Thr Cys Thr Val Ser Gly Asp Pro Ile Thr Ser Gly
                20                  25                  30

Ala Ala Ser Thr Ala Ala Tyr Ser Trp Ser Trp Ile Arg Gln Thr Pro
            35                  40                  45

Gly Lys Gly Pro Glu Trp Ile Gly Tyr Ile Phe Gln Ser Gly Ser Thr
        50                  55                  60

Tyr Phe Asn Pro Ala Leu Gln Ser Arg Ala Ser Ile Ser Ile Asp Ala
65                  70                  75                  80

Ser Asn Asn His Phe Ser Leu Lys Leu Ser Ser Leu Thr Ala Ala Asp
                85                  90                  95

Thr Ala Met Tyr Tyr Cys Ala Arg Gly Val Thr Val Phe Gly Val Val
                100                 105                 110

Thr His Phe Asp His Trp Gly Gln Gly Thr Leu Val Thr Val Ser Ser
            115                 120                 125
```

<210> SEQ ID NO 6
<211> LENGTH: 13
<212> TYPE: PRT
<213> ORGANISM: Homo sapiens
<220> FEATURE:
<221> NAME/KEY: BINDING
<222> LOCATION: (1)..(13)
<223> OTHER INFORMATION: RYB1 VH CDR1

<400> SEQUENCE: 6

```
Gly Asp Pro Ile Thr Ser Gly Ala Ala Ser Thr Ala Ala
1               5                   10
```

<210> SEQ ID NO 7
<211> LENGTH: 7
<212> TYPE: PRT
<213> ORGANISM: Homo sapiens

```
<220> FEATURE:
<221> NAME/KEY: BINDING
<222> LOCATION: (1)..(7)
<223> OTHER INFORMATION: RYB1 VH CDR2

<400> SEQUENCE: 7

Ile Phe Gln Ser Gly Ser Thr
1               5

<210> SEQ ID NO 8
<211> LENGTH: 15
<212> TYPE: PRT
<213> ORGANISM: Homo sapiens
<220> FEATURE:
<221> NAME/KEY: BINDING
<222> LOCATION: (1)..(15)
<223> OTHER INFORMATION: RYB1 VH CDR3

<400> SEQUENCE: 8

Ala Arg Gly Val Thr Val Phe Gly Val Val Thr His Phe Asp His
1               5                   10                  15

<210> SEQ ID NO 9
<211> LENGTH: 108
<212> TYPE: PRT
<213> ORGANISM: Homo sapiens
<220> FEATURE:
<221> NAME/KEY: DOMAIN
<222> LOCATION: (1)..(108)
<223> OTHER INFORMATION: RYB1 VL region

<400> SEQUENCE: 9

Asp Ile Gln Met Thr Gln Phe Pro Ser Ser Val Ser Ala Ser Val Gly
1               5                   10                  15

Asp Arg Val Thr Ile Thr Cys Arg Ala Ser Arg Asn Ile Asn Ser Trp
            20                  25                  30

Leu Ala Trp Tyr Gln Gln Arg Pro Gly Lys Ala Pro Asn Leu Leu Ile
        35                  40                  45

Tyr Ala Ala Asn Ser Leu Tyr Ser Gly Val Pro Ser Arg Phe Ser Gly
    50                  55                  60

Ser Gly Ser Gly Thr Glu Phe Thr Leu Thr Ile Thr Ser Leu Gln Pro
65                  70                  75                  80

Asp Asp Phe Ala Thr Tyr Tyr Cys Gln Gln Ala Lys Thr Phe Pro Phe
                85                  90                  95

His Phe Gly Gly Gly Thr Arg Val Asp Leu Lys Arg
            100                 105

<210> SEQ ID NO 10
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: RYB1 VL CDR1

<400> SEQUENCE: 10

Arg Asn Ile Asn Ser Trp
1               5

<210> SEQ ID NO 11
<211> LENGTH: 4
<212> TYPE: PRT
<213> ORGANISM: Homo sapiens
<220> FEATURE:
```

<221> NAME/KEY: BINDING
<222> LOCATION: (1)..(4)
<223> OTHER INFORMATION: RYB1 VL CDR2

<400> SEQUENCE: 11

Ala Ala Asn Ser
1

<210> SEQ ID NO 12
<211> LENGTH: 9
<212> TYPE: PRT
<213> ORGANISM: Homo sapiens
<220> FEATURE:
<221> NAME/KEY: BINDING
<222> LOCATION: (1)..(9)
<223> OTHER INFORMATION: RYB1 VL CDR3

<400> SEQUENCE: 12

Gln Gln Ala Lys Thr Phe Pro Phe His
1               5

<210> SEQ ID NO 13
<211> LENGTH: 130
<212> TYPE: PRT
<213> ORGANISM: Homo sapiens
<220> FEATURE:
<221> NAME/KEY: DOMAIN
<222> LOCATION: (1)..(130)
<223> OTHER INFORMATION: RYB2 VH region

<400> SEQUENCE: 13

Gln Val Gln Leu Val Gln Ser Gly Thr Glu Val Lys Lys Pro Gly Ser
1               5                   10                  15

Ser Val Lys Val Ser Cys Lys Ala Ser Gly Gly Ala Phe Ser Ser Phe
            20                  25                  30

Gly Leu Ser Trp Val Arg Gln Ala Pro Gly Gln Gly Leu Glu Trp Met
        35                  40                  45

Gly Gly Ile Leu Pro Val Phe Asp Lys Ala Asn Thr Ala Gln Lys Phe
    50                  55                  60

Gln Ala Arg Val Thr Ile Thr Ala Asp Lys Ser Thr Ser Thr Ala Phe
65                  70                  75                  80

Met Glu Leu Ser Ser Leu Arg Ser Asp Asp Thr Gly Val Tyr Tyr Cys
                85                  90                  95

Ala Ile Thr Asp Leu Ser Ala Pro Gly Ala Ala Phe Arg Tyr Ser Asp
            100                 105                 110

Trp Ile Leu Arg Phe Asp Phe Trp Gly Gln Gly Thr Leu Val Thr Val
        115                 120                 125

Ser Ser
    130

<210> SEQ ID NO 14
<211> LENGTH: 8
<212> TYPE: PRT
<213> ORGANISM: Homo sapiens
<220> FEATURE:
<221> NAME/KEY: BINDING
<222> LOCATION: (1)..(8)
<223> OTHER INFORMATION: RYB2 VH CDR1

<400> SEQUENCE: 14

Gly Gly Ala Phe Ser Ser Phe Gly
1               5

```
<210> SEQ ID NO 15
<211> LENGTH: 8
<212> TYPE: PRT
<213> ORGANISM: Homo sapiens
<220> FEATURE:
<221> NAME/KEY: BINDING
<222> LOCATION: (1)..(8)
<223> OTHER INFORMATION: RYB2 VH CDR2

<400> SEQUENCE: 15

Ile Leu Pro Val Phe Asp Lys Ala
1               5

<210> SEQ ID NO 16
<211> LENGTH: 23
<212> TYPE: PRT
<213> ORGANISM: Homo sapiens
<220> FEATURE:
<221> NAME/KEY: BINDING
<222> LOCATION: (1)..(23)
<223> OTHER INFORMATION: RYB2 VH CDR3

<400> SEQUENCE: 16

Ala Ile Thr Asp Leu Ser Ala Pro Gly Ala Ala Phe Arg Tyr Ser Asp
1               5                   10                  15

Trp Ile Leu Arg Phe Asp Phe
            20

<210> SEQ ID NO 17
<211> LENGTH: 109
<212> TYPE: PRT
<213> ORGANISM: Homo sapiens
<220> FEATURE:
<221> NAME/KEY: DOMAIN
<222> LOCATION: (1)..(109)
<223> OTHER INFORMATION: RYB2 VL region

<400> SEQUENCE: 17

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Arg Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Gly
    50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg
            100                 105

<210> SEQ ID NO 18
<211> LENGTH: 7
<212> TYPE: PRT
<213> ORGANISM: Homo sapiens
<220> FEATURE:
<221> NAME/KEY: BINDING
<222> LOCATION: (1)..(7)
<223> OTHER INFORMATION: RYB2 VL CDR1

<400> SEQUENCE: 18

Gln Ser Val Arg Ser Thr Tyr
1               5
```

```
<210> SEQ ID NO 19
<211> LENGTH: 4
<212> TYPE: PRT
<213> ORGANISM: Homo sapiens
<220> FEATURE:
<221> NAME/KEY: BINDING
<222> LOCATION: (1)..(4)
<223> OTHER INFORMATION: RYB2 VL CDR2

<400> SEQUENCE: 19

Gly Ala Ser Arg
1

<210> SEQ ID NO 20
<211> LENGTH: 9
<212> TYPE: PRT
<213> ORGANISM: Homo sapiens
<220> FEATURE:
<221> NAME/KEY: BINDING
<222> LOCATION: (1)..(9)
<223> OTHER INFORMATION: RYB2 VL CDR3

<400> SEQUENCE: 20

Gln Gln Tyr Gly Ser Ser Pro Tyr Thr
1               5

<210> SEQ ID NO 21
<211> LENGTH: 125
<212> TYPE: PRT
<213> ORGANISM: Homo sapiens
<220> FEATURE:
<221> NAME/KEY: DOMAIN
<222> LOCATION: (1)..(125)
<223> OTHER INFORMATION: RYB3 VH region

<400> SEQUENCE: 21

Gln Val His Leu Gln Glu Ser Gly Pro Gly Leu Val Lys Pro Ser Gly
1               5                   10                  15

Thr Leu Ser Leu Thr Cys Ala Val Ser Gly Gly Ser Ile Arg Ser Asp
            20                  25                  30

Asn Trp Trp Ser Trp Val Arg Gln Thr Pro Gly Lys Gly Leu Glu Trp
        35                  40                  45

Ile Gly Asp Met Phe Gln Ser Gly Ile Thr Tyr Asn Pro Ser Leu
    50                  55                  60

Lys Gly Arg Val Thr Ile Ser Ile Asp Lys Ser Asn Asn Gln Phe Ser
65                  70                  75                  80

Leu Arg Leu Thr Ser Val Thr Ala Ala Asp Thr Ala Leu Tyr Tyr Cys
                85                  90                  95

Ala Arg Arg Thr Met Thr Val Met Val Thr Leu Val Leu Gly Ala Phe
            100                 105                 110

Asp Ile Trp Gly Gln Gly Thr Met Val Thr Val Ser Ser
        115                 120                 125

<210> SEQ ID NO 22
<211> LENGTH: 9
<212> TYPE: PRT
<213> ORGANISM: Homo sapiens
<220> FEATURE:
<221> NAME/KEY: BINDING
<222> LOCATION: (1)..(9)
<223> OTHER INFORMATION: RYB3 VH CDR1

<400> SEQUENCE: 22
```

Gly Gly Ser Ile Arg Ser Asp Asn Trp
1               5

<210> SEQ ID NO 23
<211> LENGTH: 7
<212> TYPE: PRT
<213> ORGANISM: Homo sapiens
<220> FEATURE:
<221> NAME/KEY: BINDING
<222> LOCATION: (1)..(7)
<223> OTHER INFORMATION: RYB3 VH CDR2

<400> SEQUENCE: 23

Met Phe Gln Ser Gly Ile Thr
1               5

<210> SEQ ID NO 24
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: RYB3 VH CDR3

<400> SEQUENCE: 24

Ala Arg Arg Thr Met Thr Val Met Val Thr Leu Val Leu Gly Ala Phe
1               5                   10                  15

Asp Ile

<210> SEQ ID NO 25
<211> LENGTH: 114
<212> TYPE: PRT
<213> ORGANISM: Homo sapiens
<220> FEATURE:
<221> NAME/KEY: DOMAIN
<222> LOCATION: (1)..(114)
<223> OTHER INFORMATION: RYB3 VL region

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Phe Tyr Ser
                20                  25                  30

Ser Ile Asn Lys Tyr Phe Leu Ser Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Ser Leu Thr
65                  70                  75                  80

Ile Ser Ser Leu Gln Ala Asp Val Ala Val Tyr Tyr Cys Gln Gln
                85                  90                  95

Tyr Tyr Ser Ser Pro Pro Thr Phe Gly Gln Gly Thr Lys Leu Glu Val
                100                 105                 110

Lys Arg

<210> SEQ ID NO 26
<211> LENGTH: 12
<212> TYPE: PRT
<213> ORGANISM: Homo sapiens
<220> FEATURE:
<221> NAME/KEY: BINDING
<222> LOCATION: (1)..(12)
<223> OTHER INFORMATION: RYB3 VL CDR1

<400> SEQUENCE: 26

Gln Thr Val Phe Tyr Ser Ser Ile Asn Lys Tyr Phe
1               5                   10

<210> SEQ ID NO 27
<211> LENGTH: 4
<212> TYPE: PRT
<213> ORGANISM: Homo sapiens
<220> FEATURE:
<221> NAME/KEY: BINDING
<222> LOCATION: (1)..(4)
<223> OTHER INFORMATION: RYB3 VL CDR2

<400> SEQUENCE: 27

Trp Ala Ser Thr
1

<210> SEQ ID NO 28
<211> LENGTH: 9
<212> TYPE: PRT
<213> ORGANISM: Homo sapiens
<220> FEATURE:
<221> NAME/KEY: BINDING
<222> LOCATION: (1)..(9)
<223> OTHER INFORMATION: RYB3 VL CDR3

<400> SEQUENCE: 28

Gln Gln Tyr Tyr Ser Ser Pro Pro Thr
1               5

<210> SEQ ID NO 29
<211> LENGTH: 363
<212> TYPE: PRT
<213> ORGANISM: Hepatitis C Virus, H77 isolate
<220> FEATURE:
<221> NAME/KEY: mat_peptide
<222> LOCATION: (1)..(363)
<223> OTHER INFORMATION: E2 protein
<300> PUBLICATION INFORMATION:
<308> DATABASE ACCESSION NUMBER: NCBI Protein / NP_751921.1
<309> DATABASE ENTRY DATE: 1997-06-19
<313> RELEVANT RESIDUES IN SEQ ID NO: (1)..(363)

<400> SEQUENCE: 29

Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
                20                  25                  30

Thr Asn Gly Ser Trp His Ile Asn Ser Thr Ala Leu Asn Cys Asn Glu
            35                  40                  45

Ser Leu Asn Thr Gly Trp Leu Ala Gly Leu Phe Tyr Gln His Lys Phe
        50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

```
Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
            340                 345                 350

Trp Met Met Leu Leu Ile Ser Gln Ala Glu Ala
        355                 360

<210> SEQ ID NO 30
<211> LENGTH: 10
<212> TYPE: PRT
<213> ORGANISM: Hepatitis C Virus, H77 isolate

<400> SEQUENCE: 30

His Pro Glu Ala Thr Tyr Ser Arg Cys Gly
1               5                   10

<210> SEQ ID NO 31
<211> LENGTH: 6
<212> TYPE: PRT
<213> ORGANISM: Hepatitis C Virus, H77 isolate

<400> SEQUENCE: 31

Glu Ala Thr Tyr Ser Arg
1               5

<210> SEQ ID NO 32
<211> LENGTH: 8
<212> TYPE: PRT
<213> ORGANISM: Hepatitis C Virus, H77 isolate

<400> SEQUENCE: 32

Val Cys Gly Pro Val Tyr Cys Phe
1               5

<210> SEQ ID NO 33
<211> LENGTH: 6
<212> TYPE: PRT
```

```
<213> ORGANISM: Hepatitis C Virus, H77 isolate

<400> SEQUENCE: 33

Cys Gly Pro Val Tyr Cys
1               5

<210> SEQ ID NO 34
<211> LENGTH: 17
<212> TYPE: PRT
<213> ORGANISM: Hepatitis C Virus, H77 isolate

<400> SEQUENCE: 34

His Pro Glu Ala Thr Tyr Ser Arg Cys Gly Ser Gly Pro Trp Ile Thr
1               5                   10                  15

Pro

<210> SEQ ID NO 35
<211> LENGTH: 6
<212> TYPE: PRT
<213> ORGANISM: Hepatitis C Virus, H77 isolate

<400> SEQUENCE: 35

Tyr Ser Arg Cys Gly Ser
1               5

<210> SEQ ID NO 36
<211> LENGTH: 6
<212> TYPE: PRT
<213> ORGANISM: Hepatitis C Virus, H77 isolate

<400> SEQUENCE: 36

Ser Arg Cys Gly Ser Gly
1               5

<210> SEQ ID NO 37
<211> LENGTH: 8
<212> TYPE: PRT
<213> ORGANISM: Artificial Sequence
<220> FEATURE:
<223> OTHER INFORMATION: HC-11 Heavy Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 37

Gly Ala Thr Phe Ser Ser Phe Ile
1               5

<210> SEQ ID NO 38
<211> LENGTH: 8
<212> TYPE: PRT
<213> ORGANISM: Artificial Sequence
<220> FEATURE:
<223> OTHER INFORMATION: HC-11 Heavy Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 38

Ile Ile Pro Met Phe Gly Thr Ala
1               5
```

```
<210> SEQ ID NO 39
<211> LENGTH: 19
<212> TYPE: PRT
<213> ORGANISM: Artificial Sequence
<220> FEATURE:
<223> OTHER INFORMATION: HC-11 Heavy Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(19)

<400> SEQUENCE: 39

Ala Met Glu Val Pro Gly Phe Cys Arg Gly Gly Ser Cys Ser Gly Tyr
1               5                   10                  15

Met Asp Val

<210> SEQ ID NO 40
<211> LENGTH: 7
<212> TYPE: PRT
<213> ORGANISM: Artificial Sequence
<220> FEATURE:
<223> OTHER INFORMATION: HC-11 Light Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(7)

<400> SEQUENCE: 40

His Ser Val Ser Ser Ser Asn
1               5

<210> SEQ ID NO 41
<211> LENGTH: 4
<212> TYPE: PRT
<213> ORGANISM: Artificial Sequence
<220> FEATURE:
<223> OTHER INFORMATION: HC-11 Light Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(4)

<400> SEQUENCE: 41

Gly Ala Ser Ala
1

<210> SEQ ID NO 42
<211> LENGTH: 9
<212> TYPE: PRT
<213> ORGANISM: Artificial Sequence
<220> FEATURE:
<223> OTHER INFORMATION: HC-11 Light Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(9)

<400> SEQUENCE: 42

Gln Gln Tyr Gly Ser Ser Pro Ile Thr
1               5

<210> SEQ ID NO 43
<211> LENGTH: 8
<212> TYPE: PRT
<213> ORGANISM: Artificial Sequence
<220> FEATURE:
```

<223> OTHER INFORMATION: HC-1 Heavy Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 43

Gly Gly Thr Tyr Asn Ser Glu Val
1               5

<210> SEQ ID NO 44
<211> LENGTH: 8
<212> TYPE: PRT
<213> ORGANISM: Artificial Sequence
<220> FEATURE:
<223> OTHER INFORMATION: HC-1 Heavy Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 44

Phe Ile Pro Met Phe Gly Thr Ala
1               5

<210> SEQ ID NO 45
<211> LENGTH: 15
<212> TYPE: PRT
<213> ORGANISM: Artificial Sequence
<220> FEATURE:
<223> OTHER INFORMATION: HC-1 Heavy Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(15)

<400> SEQUENCE: 45

Ala Lys Val Leu Gln Val Gly Gly Asn Leu Val Val Arg Pro Leu
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: HC-1 Light Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(7)

<400> SEQUENCE: 46

Gln Thr Ile Ser Ser Thr His
1               5

<210> SEQ ID NO 47
<211> LENGTH: 4
<212> TYPE: PRT
<213> ORGANISM: Artificial Sequence
<220> FEATURE:
<223> OTHER INFORMATION: HC-1 Light Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(4)

```
<400> SEQUENCE: 47

Gly Val Ser Ala
1

<210> SEQ ID NO 48
<211> LENGTH: 9
<212> TYPE: PRT
<213> ORGANISM: Artificial Sequence
<220> FEATURE:
<223> OTHER INFORMATION: HC-1 Light Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(9)

<400> SEQUENCE: 48

His Gln Tyr Gly Asn Ser Pro Gln Thr
1               5

<210> SEQ ID NO 49
<211> LENGTH: 10
<212> TYPE: PRT
<213> ORGANISM: Artificial Sequence
<220> FEATURE:
<223> OTHER INFORMATION: HC-3 Heavy Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(10)

<400> SEQUENCE: 49

Gly Phe Ser Leu Ser Thr Thr Gly Val Gly
1               5                   10

<210> SEQ ID NO 50
<211> LENGTH: 7
<212> TYPE: PRT
<213> ORGANISM: Artificial Sequence
<220> FEATURE:
<223> OTHER INFORMATION: HC-3 Heavy Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(7)

<400> SEQUENCE: 50

Ile Tyr Trp Asp Asp Asp Lys
1               5

<210> SEQ ID NO 51
<211> LENGTH: 23
<212> TYPE: PRT
<213> ORGANISM: Artificial Sequence
<220> FEATURE:
<223> OTHER INFORMATION: HC-3 Heavy Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(23)

<400> SEQUENCE: 51

Ala Leu Asn Ser Tyr Arg Ser Gly Thr Ile Leu Tyr Arg Glu Leu Glu
1               5                   10                  15

Leu Arg Gly Leu Phe Tyr Ile
            20
```

<210> SEQ ID NO 52
<211> LENGTH: 6
<212> TYPE: PRT
<213> ORGANISM: Artificial Sequence
<220> FEATURE:
<223> OTHER INFORMATION: HC-3 Light Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(6)

<400> SEQUENCE: 52

Gln Ser Ile Ser Ser Trp
1               5

<210> SEQ ID NO 53
<211> LENGTH: 4
<212> TYPE: PRT
<213> ORGANISM: Artificial Sequence
<220> FEATURE:
<223> OTHER INFORMATION: HC-3 Light Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(4)

<400> SEQUENCE: 53

Glu Ser Ser Ala
1

<210> SEQ ID NO 54
<211> LENGTH: 9
<212> TYPE: PRT
<213> ORGANISM: Artificial Sequence
<220> FEATURE:
<223> OTHER INFORMATION: HC-3 Light Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(9)

<400> SEQUENCE: 54

Gln Gln Tyr Glu Ser Ser Ser Trp Thr
1               5

<210> SEQ ID NO 55
<211> LENGTH: 8
<212> TYPE: PRT
<213> ORGANISM: Artificial Sequence
<220> FEATURE:
<223> OTHER INFORMATION: CBH-23 Heavy Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 55

Gly Gly Thr Phe Ser Ser Tyr Ala
1               5

<210> SEQ ID NO 56
<211> LENGTH: 8
<212> TYPE: PRT
<213> ORGANISM: Artificial Sequence
<220> FEATURE:

<223> OTHER INFORMATION: CBH-23 Heavy Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(8)

<400> SEQUENCE: 56

Ile Val Pro Met Phe Gly Thr Glu
1               5

<210> SEQ ID NO 57
<211> LENGTH: 13
<212> TYPE: PRT
<213> ORGANISM: Artificial Sequence
<220> FEATURE:
<223> OTHER INFORMATION: CBH-23 Heavy Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(13)

<400> SEQUENCE: 57

Ala Arg His Glu Asn Ile Tyr Gly Thr Pro Phe Asp Tyr
1               5                   10

<210> SEQ ID NO 58
<211> LENGTH: 6
<212> TYPE: PRT
<213> ORGANISM: Artificial Sequence
<220> FEATURE:
<223> OTHER INFORMATION: CBH-23 Light Chain CDR1
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(6)

<400> SEQUENCE: 58

His Ser Ile Thr Arg Tyr
1               5

<210> SEQ ID NO 59
<211> LENGTH: 4
<212> TYPE: PRT
<213> ORGANISM: Artificial Sequence
<220> FEATURE:
<223> OTHER INFORMATION: CBH-23 Light Chain CDR2
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(4)

<400> SEQUENCE: 59

Ala Ala Ser Ala
1

<210> SEQ ID NO 60
<211> LENGTH: 9
<212> TYPE: PRT
<213> ORGANISM: Artificial Sequence
<220> FEATURE:
<223> OTHER INFORMATION: CBH-23 Light Chain CDR3
<300> PUBLICATION INFORMATION:
<302> TITLE: Hepatitis C antibodies and uses thereof
<310> PATENT DOCUMENT NUMBER: US 20120039846 A1
<311> PATENT FILING DATE: 2008-10-05
<313> RELEVANT RESIDUES IN SEQ ID NO: (1)..(9)

```
<400> SEQUENCE: 60

Gln Gln Ser Tyr Ser Thr Leu Leu Thr
1               5

<210> SEQ ID NO 61
<211> LENGTH: 20
<212> TYPE: PRT
<213> ORGANISM: Hepatitis C Virus, H77 isolate

<400> SEQUENCE: 61

Glu Thr His Val Thr Gly Gly Ser Ala Gly Arg Thr Thr Ala Gly Leu
1               5                   10                  15

Val Gly Leu Leu
            20

<210> SEQ ID NO 62
<211> LENGTH: 17
<212> TYPE: PRT
<213> ORGANISM: Hepatitis C Virus, H77 isolate

<400> SEQUENCE: 62

Thr Pro Gly Ala Lys Gln Asn Ile Gln Leu Ile Asn Thr Asn Gly Ser
1               5                   10                  15

Trp

<210> SEQ ID NO 63
<211> LENGTH: 7
<212> TYPE: PRT
<213> ORGANISM: Hepatitis C Virus, H77 isolate

<400> SEQUENCE: 63

Ile Asn Thr Asn Gly Ser Trp
1               5

<210> SEQ ID NO 64
<211> LENGTH: 11
<212> TYPE: PRT
<213> ORGANISM: Hepatitis C Virus, H77 isolate

<400> SEQUENCE: 64

Asn Cys Asn Glu Ser Leu Asn Thr Gly Trp Leu
1               5                   10

<210> SEQ ID NO 65
<211> LENGTH: 9
<212> TYPE: PRT
<213> ORGANISM: Hepatitis C Virus, H77 isolate

<400> SEQUENCE: 65

Ala Gln Gly Trp Gly Pro Ile Ser Tyr
1               5

<210> SEQ ID NO 66
<211> LENGTH: 16
<212> TYPE: PRT
<213> ORGANISM: Hepatitis C Virus, H77 isolate

<400> SEQUENCE: 66

Gly Pro Ile Ser Tyr Ala Asn Gly Ser Gly Leu Asp Glu Arg Pro Tyr
1               5                   10                  15

<210> SEQ ID NO 67
<211> LENGTH: 11
```

<212> TYPE: PRT
<213> ORGANISM: Hepatitis C Virus, H77 isolate

<400> SEQUENCE: 67

Ala Asn Gly Ser Gly Leu Asp Glu Arg Pro Tyr
1               5                   10

<210> SEQ ID NO 68
<211> LENGTH: 13
<212> TYPE: PRT
<213> ORGANISM: Hepatitis C Virus, H77 isolate

<400> SEQUENCE: 68

Ala Asn Gly Ser Gly Leu Asp Glu Arg Pro Tyr Cys Trp
1               5                   10

<210> SEQ ID NO 69
<211> LENGTH: 22
<212> TYPE: PRT
<213> ORGANISM: Hepatitis C virus, H77 genotype

<400> SEQUENCE: 69

Cys Trp His Tyr Pro Pro Arg Pro Cys Gly Ile Val Pro Ala Lys Ser
1               5                   10                  15

Val Cys Gly Pro Val Tyr
            20

<210> SEQ ID NO 70
<211> LENGTH: 20
<212> TYPE: PRT
<213> ORGANISM: Hepatitis C virus, H77 genotype

<400> SEQUENCE: 70

His Tyr Pro Pro Arg Pro Cys Gly Ile Val Pro Ala Lys Ser Val Cys
1               5                   10                  15

Gly Pro Val Tyr
            20

<210> SEQ ID NO 71
<211> LENGTH: 8
<212> TYPE: PRT
<213> ORGANISM: Hepatitis C Virus, H77 isolate

<400> SEQUENCE: 71

Pro Cys Gly Ile Val Pro Ala Lys
1               5

<210> SEQ ID NO 72
<211> LENGTH: 29
<212> TYPE: PRT
<213> ORGANISM: Hepatitis C Virus, H77 isolate

<400> SEQUENCE: 72

Pro Cys Gly Ile Val Pro Ala Lys Ser Val Cys Gly Pro Val Tyr Cys
1               5                   10                  15

Phe Thr Pro Ser Pro Val Val Val Gly Thr Thr Asp Arg
            20                  25

<210> SEQ ID NO 73
<211> LENGTH: 27
<212> TYPE: PRT
<213> ORGANISM: Hepatitis C Virus, H77 isolate

<400> SEQUENCE: 73

Cys Gly Ile Val Pro Ala Lys Ser Val Cys Gly Pro Val Tyr Cys Phe
1               5                   10                  15

Thr Pro Ser Pro Val Trp Gly Thr Thr Asp Arg
            20                  25

<210> SEQ ID NO 74
<211> LENGTH: 27
<212> TYPE: PRT
<213> ORGANISM: Hepatitis C Virus, H77 isolate

<400> SEQUENCE: 74

Gly Ile Val Pro Ala Lys Ser Val Cys Gly Pro Val Tyr Cys Phe Thr
1               5                   10                  15

Pro Ser Pro Val Val Gly Thr Thr Asp Arg
            20                  25

<210> SEQ ID NO 75
<211> LENGTH: 15
<212> TYPE: PRT
<213> ORGANISM: Hepatitis C Virus, H77 isolate

<400> SEQUENCE: 75

Cys Phe Thr Pro Ser Pro Val Val Gly Thr Thr Asp Arg Ser
1               5                   10                  15

<210> SEQ ID NO 76
<211> LENGTH: 20
<212> TYPE: PRT
<213> ORGANISM: Hepatitis C Virus, H77 isolate

<400> SEQUENCE: 76

Cys Phe Thr Pro Ser Pro Val Val Val Gly Thr Thr Asp Arg Ser Gly
1               5                   10                  15

Ala Pro Thr Tyr
            20

<210> SEQ ID NO 77
<211> LENGTH: 18
<212> TYPE: PRT
<213> ORGANISM: Hepatitis C Virus, H77 isolate

<400> SEQUENCE: 77

Thr Pro Ser Pro Val Val Val Gly Thr Thr Asp Arg Ser Gly Ala Pro
1               5                   10                  15

Thr Tyr

<210> SEQ ID NO 78
<211> LENGTH: 14
<212> TYPE: PRT
<213> ORGANISM: Hepatitis C Virus, H77 isolate

<400> SEQUENCE: 78

Cys Phe Thr Pro Ser Pro Val Val Val Gly Thr Thr Asp Arg
1               5                   10

<210> SEQ ID NO 79
<211> LENGTH: 13
<212> TYPE: PRT
<213> ORGANISM: Hepatitis C Virus, H77 isolate

<400> SEQUENCE: 79

Phe Thr Pro Ser Pro Val Val Val Gly Thr Thr Asp Arg

<210> SEQ ID NO 80
<211> LENGTH: 26
<212> TYPE: PRT
<213> ORGANISM: Hepatitis C Virus, H77 isolate

<400> SEQUENCE: 80

Met Asn Ser Thr Gly Phe Thr Lys Val Cys Gly Ala Pro Pro Cys Val
1               5                   10                  15

Ile Gly Gly Val Gly Asn Asn Thr Leu Leu
            20                  25

<210> SEQ ID NO 81
<211> LENGTH: 20
<212> TYPE: PRT
<213> ORGANISM: Hepatitis C Virus, H77 isolate

<400> SEQUENCE: 81

Thr Lys Val Cys Gly Ala Pro Pro Cys Val Ile Gly Gly Val Gly Asn
1               5                   10                  15

Asn Thr Leu Leu
            20

<210> SEQ ID NO 82
<211> LENGTH: 6
<212> TYPE: PRT
<213> ORGANISM: Hepatitis C Virus, H77 isolate

<400> SEQUENCE: 82

Cys Pro Thr Asp Cys Phe
1               5

<210> SEQ ID NO 83
<211> LENGTH: 16
<212> TYPE: PRT
<213> ORGANISM: Hepatitis C Virus, H77 isolate

<400> SEQUENCE: 83

Arg Lys His Pro Glu Ala Thr Tyr Ser Arg Cys Gly Ser Gly Pro Trp
1               5                   10                  15

<210> SEQ ID NO 84
<211> LENGTH: 19
<212> TYPE: PRT
<213> ORGANISM: Hepatitis C Virus, H77 isolate

<400> SEQUENCE: 84

Lys His Pro Glu Ala Thr Tyr Ser Arg Cys Gly Ser Gly Pro Trp Ile
1               5                   10                  15

Thr Pro Arg

<210> SEQ ID NO 85
<211> LENGTH: 8
<212> TYPE: PRT
<213> ORGANISM: Hepatitis C Virus, H77 isolate

<400> SEQUENCE: 85

Ser Arg Cys Gly Ser Gly Pro Trp
1               5

<210> SEQ ID NO 86
<211> LENGTH: 18

```
<212> TYPE: PRT
<213> ORGANISM: Hepatitis C Virus, H77 isolate

<400> SEQUENCE: 86

His Pro Glu Ala Thr Tyr Ser Arg Cys Gly Ser Gly Pro Trp Ile Thr
1               5                   10                  15

Pro Arg

<210> SEQ ID NO 87
<211> LENGTH: 11
<212> TYPE: PRT
<213> ORGANISM: Hepatitis C Virus, H77 isolate

<400> SEQUENCE: 87

Ile Thr Pro Arg Cys Met Val Asp Tyr Pro Tyr
1               5                   10

<210> SEQ ID NO 88
<211> LENGTH: 19
<212> TYPE: PRT
<213> ORGANISM: Hepatitis C Virus, H77 isolate

<400> SEQUENCE: 88

Lys His Pro Glu Ala Thr Tyr Ser Arg Cys Gly Ser Gly Pro Trp Ile
1               5                   10                  15

Thr Pro Arg

<210> SEQ ID NO 89
<211> LENGTH: 18
<212> TYPE: PRT
<213> ORGANISM: Hepatitis C Virus, H77 isolate

<400> SEQUENCE: 89

His Pro Glu Ala Thr Tyr Ser Arg Cys Gly Ser Gly Pro Trp Ile Thr
1               5                   10                  15

Pro Arg

<210> SEQ ID NO 90
<211> LENGTH: 18
<212> TYPE: PRT
<213> ORGANISM: Hepatitis C Virus, H77 isolate

<400> SEQUENCE: 90

Cys Gly Ser Gly Pro Trp Ile Thr Pro Arg Cys Met Val Asp Tyr Pro
1               5                   10                  15

Tyr Arg

<210> SEQ ID NO 91
<211> LENGTH: 8
<212> TYPE: PRT
<213> ORGANISM: Hepatitis C Virus, H77 isolate

<400> SEQUENCE: 91

Cys Met Val Asp Tyr Pro Tyr Arg
1               5

<210> SEQ ID NO 92
<211> LENGTH: 9
<212> TYPE: PRT
<213> ORGANISM: Hepatitis C Virus, H77 isolate

<400> SEQUENCE: 92
```

```
Met Tyr Val Gly Gly Val Glu His Arg
1               5

<210> SEQ ID NO 93
<211> LENGTH: 14
<212> TYPE: PRT
<213> ORGANISM: Hepatitis C Virus, H77 isolate

<400> SEQUENCE: 93

Val Gly Gly Val Glu His Arg Leu Glu Ala Ala Cys Asn Trp
1               5                   10

<210> SEQ ID NO 94
<211> LENGTH: 8
<212> TYPE: PRT
<213> ORGANISM: Hepatitis C Virus, H77 isolate

<400> SEQUENCE: 94

Val Gly Gly Val Glu His Arg Leu
1               5

<210> SEQ ID NO 95
<211> LENGTH: 9
<212> TYPE: PRT
<213> ORGANISM: Hepatitis C Virus, H77 isolate

<400> SEQUENCE: 95

Leu Glu Ala Ala Cys Asn Trp Thr Arg
1               5

<210> SEQ ID NO 96
<211> LENGTH: 9
<212> TYPE: PRT
<213> ORGANISM: Hepatitis C Virus, H77 isolate

<400> SEQUENCE: 96

Gly Glu Arg Cys Asp Leu Glu Asp Arg
1               5

<210> SEQ ID NO 97
<211> LENGTH: 7
<212> TYPE: PRT
<213> ORGANISM: Hepatitis C Virus, H77 isolate

<400> SEQUENCE: 97

Leu Leu Ser Thr Thr Gln Trp
1               5

<210> SEQ ID NO 98
<211> LENGTH: 9
<212> TYPE: PRT
<213> ORGANISM: Hepatitis C Virus, H77 isolate

<400> SEQUENCE: 98

His Gln Asn Ile Val Asp Val Gln Tyr
1               5

<210> SEQ ID NO 99
<211> LENGTH: 11
<212> TYPE: PRT
<213> ORGANISM: Hepatitis C Virus, H77 isolate

<400> SEQUENCE: 99

Leu Tyr Gly Val Gly Ser Ser Ile Ala Ser Trp
1               5                   10
```

```
<210> SEQ ID NO 100
<211> LENGTH: 10
<212> TYPE: PRT
<213> ORGANISM: Hepatitis C Virus, H77 isolate

<400> SEQUENCE: 100

Tyr Gly Val Gly Ser Ser Ile Ala Ser Trp
1               5                   10

<210> SEQ ID NO 101
<211> LENGTH: 11
<212> TYPE: PRT
<213> ORGANISM: Hepatitis C Virus, H77 isolate

<400> SEQUENCE: 101

Leu Ala Asp Ala Arg Val Cys Ser Cys Leu Trp
1               5                   10

<210> SEQ ID NO 102
<211> LENGTH: 9
<212> TYPE: PRT
<213> ORGANISM: Hepatitis C Virus, H77 isolate

<400> SEQUENCE: 102

Ala Asp Ala Arg Val Cys Ser Cys Leu
1               5

<210> SEQ ID NO 103
<211> LENGTH: 10
<212> TYPE: PRT
<213> ORGANISM: Hepatitis C virus, H77 genotype

<400> SEQUENCE: 103

Ala Asp Ala Arg Val Cys Ser Cys Leu Trp
1               5                   10

<210> SEQ ID NO 104
<211> LENGTH: 10
<212> TYPE: PRT
<213> ORGANISM: Hepatitis C virus

<400> SEQUENCE: 104

His Pro Asp Thr Thr Tyr Leu Lys Cys Gly
1               5                   10

<210> SEQ ID NO 105
<211> LENGTH: 17
<212> TYPE: PRT
<213> ORGANISM: Hepatitis C virus

<400> SEQUENCE: 105

His Pro Asp Thr Thr Tyr Leu Lys Cys Gly Ser Gly Pro Trp Leu Thr
1               5                   10                  15

Pro

<210> SEQ ID NO 106
<211> LENGTH: 17
<212> TYPE: PRT
<213> ORGANISM: Hepatitis C virus

<400> SEQUENCE: 106

His Pro Glu Ala Thr Tyr Ser Arg Cys Gly Ser Gly Pro Trp Leu Thr
1               5                   10                  15
```

Pro

<210> SEQ ID NO 107
<211> LENGTH: 10
<212> TYPE: PRT
<213> ORGANISM: Hepatitis C virus

<400> SEQUENCE: 107

His Pro Glu Thr Thr Tyr Ala Lys Cys Gly
1               5                   10

<210> SEQ ID NO 108
<211> LENGTH: 17
<212> TYPE: PRT
<213> ORGANISM: Hepatitis C virus

<400> SEQUENCE: 108

His Pro Glu Thr Thr Tyr Ala Lys Cys Gly Ser Gly Pro Trp Ile Thr
1               5                   10                  15

Pro

<210> SEQ ID NO 109
<211> LENGTH: 10
<212> TYPE: PRT
<213> ORGANISM: Hepatitis C virus

<400> SEQUENCE: 109

His Pro Asp Ala Thr Tyr Thr Lys Cys Gly
1               5                   10

<210> SEQ ID NO 110
<211> LENGTH: 17
<212> TYPE: PRT
<213> ORGANISM: Hepatitis C virus

<400> SEQUENCE: 110

His Pro Asp Ala Thr Tyr Thr Lys Cys Gly Ser Gly Pro Trp Leu Thr
1               5                   10                  15

Pro

<210> SEQ ID NO 111
<211> LENGTH: 10
<212> TYPE: PRT
<213> ORGANISM: Hepatitis C virus

<400> SEQUENCE: 111

His Pro Glu Ala Thr Tyr Gln Arg Cys Gly
1               5                   10

<210> SEQ ID NO 112
<211> LENGTH: 17
<212> TYPE: PRT
<213> ORGANISM: Hepatitis C virus

<400> SEQUENCE: 112

His Pro Glu Ala Thr Tyr Gln Arg Cys Gly Ser Gly Pro Trp Leu Thr
1               5                   10                  15

Pro

<210> SEQ ID NO 113
<211> LENGTH: 34
<212> TYPE: PRT

```
<213> ORGANISM: Hepatitis C Virus, H77 isolate

<400> SEQUENCE: 113

Cys Pro Thr Asp Cys Phe Arg Lys His Pro Glu Ala Thr Tyr Ser Arg
1               5                   10                  15

Cys Gly Ser Gly Pro Trp Ile Thr Pro Arg Cys Met Val Asp Tyr Pro
                20                  25                  30

Tyr Arg

<210> SEQ ID NO 114
<211> LENGTH: 42
<212> TYPE: PRT
<213> ORGANISM: Hepatitis C Virus, H77 isolate

<400> SEQUENCE: 114

Cys Trp His Tyr Pro Pro Arg Pro Cys Gly Ile Val Pro Ala Lys Ser
1               5                   10                  15

Val Cys Gly Pro Val Tyr Cys Phe Thr Pro Ser Pro Val Val Val Gly
                20                  25                  30

Thr Thr Asp Arg Ser Gly Ala Pro Thr Tyr
            35                  40

<210> SEQ ID NO 115
<211> LENGTH: 60
<212> TYPE: PRT
<213> ORGANISM: Hepatitis C Virus, H77 isolate

<400> SEQUENCE: 115

Met Asn Ser Thr Gly Phe Thr Lys Val Cys Gly Ala Pro Pro Cys Val
1               5                   10                  15

Ile Gly Gly Val Gly Asn Asn Thr Leu Leu Cys Pro Thr Asp Cys Phe
                20                  25                  30

Arg Lys His Pro Glu Ala Thr Tyr Ser Arg Cys Gly Ser Gly Pro Trp
            35                  40                  45

Ile Thr Pro Arg Cys Met Val Asp Tyr Pro Tyr Arg
    50                  55                  60
```